(12) United States Patent
Cowden et al.

(10) Patent No.: US 6,878,690 B2
(45) Date of Patent: Apr. 12, 2005

(54) COMPOUNDS AND METHODS

(75) Inventors: William Butler Cowden, Kambah (AU); Bart Michael Eschler, Giralang (AU); Darren Ray March, Banks (AU); Douglas John Francis, Garran (AU); Sendaba Gerba, Kaleen (AU); Gavin James Bartell, Conder (AU); Brett Charlton, Fraser (AU)

(73) Assignee: PharmAxis Pty Ltd., Canberra (AU)

( * ) Notice: Subject to any disclaimer, the term of this patent is extended or adjusted under 35 U.S.C. 154(b) by 0 days.

(21) Appl. No.: 10/338,679

(22) Filed: Jan. 9, 2003

(65) Prior Publication Data

US 2003/0176363 A1 Sep. 18, 2003

Related U.S. Application Data

(63) Continuation-in-part of application No. PCT/AU01/00831, filed on Jul. 11, 2001.

(30) Foreign Application Priority Data

Jul. 11, 2000 (AU) .............................................. PQ8723

(51) Int. Cl.[7] ...................... A61K 31/7024; C07H 5/06
(52) U.S. Cl. ........................... 514/23; 514/42; 536/18.7
(58) Field of Search .................... 514/23, 42; 536/18.7, 536/1.11, 4.1

(56) References Cited

U.S. PATENT DOCUMENTS

| 5,506,210 A | 4/1996 | Parish et al. .................. 514/23 |
| 6,294,521 B1 | 9/2001 | Cowden ...................... 514/23 |

FOREIGN PATENT DOCUMENTS

| WO | WO 97/05883 A | 2/1997 |

OTHER PUBLICATIONS

Woeckenhaus et al "Simple Methods of Preparing Nicotinamide Mononucleotide andRelatedAnalogs", Methods in Enzymology 1980, 66, 62–70.*

Lemmen et al "FLEXS: A Method for Fast Flexible Ligand Superposition", Journal of Medicinal Chemistry, 1998, 41, 4502–4520.*

Flanigan, I.L. et al., Magn. Reson. Chem (1995), 33(3), 231–2. "Assignment of the 1H NMR resonances of D–glycerol–D–ido– and D–glycerol–D–alto–octulose mono– and biphosphates", Structure 6.

Luengo, J.I. et al., Tetrahedron Lett. (1992), 33(46), 6911–14. "Synthesis of C–fucopyranosyl analogs of GDP–L–fucose as inhibitors of fucosyltransferases", Compound 15.

Detheux, M. et al., Eur. J. Biochem. (1991), 200(2), 553–61, "Effectors of the regulatory protein acting on liver glucokinase: a kinetic investigation", Figure 7.

Flanigan, I.L. et al., Magn. Reson. Chem (1995), 33(3), 231–2. "Assignment of the 1H NMR resonaces of D–glycerol–D–ido– and D–glycerol–D–alto–octulose mono– and biphosphates", Structure 6.

Luengo, J.I. et al., Tetrahedron Lett. (1992), 33(46), 6911–14. "Synthesis of C–fucopyranosyl analogs of GDP–L–fucose as inhibitiors of fucosyltransferases", Compound 15.

Detheux, M. et al., Eur. J. Biochem. (1991), 200(2), 553–61, "Effectors of the regulatory protein acting on liver glucokinase: a kinetic investigation", Figure 7.

William J. Ray, Jr. et al., "Reaction of the Isosteric Methylenephosphonate Analog of α–D–Glucose 1–Phosphate with Phosphoglucomutase. Induced–Fit Specificity Revisited", BIOCHEMISTRY (1993), 32(1), 38–47, XP002258518.

* cited by examiner

Primary Examiner—James O. Wilson
Assistant Examiner—Ganapathy Krishnan
(74) Attorney, Agent, or Firm—Bacon & Thomas PLLC

(57) ABSTRACT

The present invention provides phosphotetrahydropyran compounds and the use thereof in treating diseases or conditions that are dependent on T-lymphocyte migration, as well as compositions containing said compounds.

18 Claims, 2 Drawing Sheets

COMPOUNDS AND METHODS

This application is a continuation-in-part of copending international application No. PCT/AU01/00831, filed Jul. 11, 2001.

FIELD OF THE INVENTION

The present invention relates generally to novel phosphotetrahydropyran compounds and the use thereof in treating diseases that are dependent upon T lymphocyte migration. In particular, the present invention relates to the use of these compounds in the treatment of T lymphocyte mediated inflammatory diseases in animals and man and compositions containing said compounds.

BACKGROUND OF THE INVENTION

For convenience, the adaptive immune response to infection in mammals, is often divided into antibody (or humoral) responses and cell-mediated responses. These two arms of the immune response are initiated by different cell types. Thus, antibody immune responses are generated by the antibody producing lymphoid cells referred to as B lymphocytes or B cells, while the adaptive cell-mediated immune response is the direct result of antigen recognition by T lymphocytes or T cells in the context of the major histocompatibility complex (MHC) antigen. The processes involved in these responses and the roles played by these lymphoid cells in infection are now well understood and published works outlining the nature and functioning of these cells are readily available including inter alia: Immunology 5$^{th}$ Edition; I. M. Roitt Ed, Blackwell Scientific Publications, Boston, 1998 and Immunobiology: the Immune System in Health and Disease 4$^{th}$ Edition, C. A. Janeway, P. Travers, M. Walport and J. D. Capra Eds, Elsevier Science/Garland Publishing, New York, 1999; incorporated herein by reference.

T cells perform the role of immunological surveillance by constantly recirculating throughout the body. Most of the recirculation takes place in the movement of T cells from the lymph nodes into the blood stream via the lymphatic ducts and then re-entering the nodes via the nodal post capillary venules. The remaining recirculation takes place when T cells leave the blood stream via capillaries in various tissues of the body, migrate through these tissues into draining lymphatics and thus into the local draining lymph node. If the T cell encounters a specific antigen to which it is capable of responding when recirculating through the tissues it will initiate a cell-mediated immune response. Thus, in the case of an infectious agent the T cell will in most cases respond in a manner that will ultimately result in clearance of the pathogen. In some cases, however, this response may be excessive and result in damage to normal host tissue in the vicinity of the infectious agent. In other cases T cells can initiate an inappropriate immune response. This can happen, for example, when the T cell responds to one of the body's own tissue components. When this happens in a clinically apparent manner, the resulting disorder is termed an autoimmune disease. Descriptions of this process can be found in many scientific and medical publications including The Pathogenesis of Infectious Disease, C. A. Mims Ed; Academic Press, New York, 1982, incorporated herein by reference.

There are many pathological disorders of human beings that are the direct result of autoreactive T lymphocyte mediated inflammation, included among these immunopathological maladies are the autoimmune diseases such as multiple sclerosis (MS), rheumatoid arthritis, acute disseminated encephalomyelitis (ADE) and Type I diabetes (Klein, J. and Horejsi, Vaclav 1997. Autoimmunity and autoimmune diseases, pp 656–657. In: Immunology (Second Edition), Blackwell Science Ltd., Oxford. Psoriasis, although previously believed to be a disorder of keratinocytes, is now known to be a T cell mediated inflammatory disease of the skin; the immunological basis of psoriasis has been reviewed by Bos and De Rie (Bos J. D. and De Rie M. A., (1999). The pathogenesis of psoriasis: immunological facts and speculations. Immunology Today, vol. 20, 40–46; incorporated herein by reference).

It has now been found that compounds of the present invention, which are phosphotetrahydropyrans of Formula (I), may be effective at inhibiting the migration of T lymphocytes from the blood stream into tissues and thus may have utility in the treatment of diseases or conditions mediated by T lymphocyte migration.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Accordingly, in a first aspect, the present invention provides a phosphotetrahydropyran of formula (I), or a salt, derivative or prodrug thereof, in the configuration depicted (2RS):

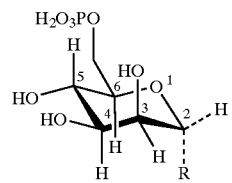

wherein R is axial or equitorial and is selected from the group consisting of:

alkyl, alkenyl, alkynyl, aryl, heteroaryl, aralkyl, heteroaralkyl, cyano, hydroxy-tetrahydro-pyranyloxyalkyl, —(CH$_2$)$_n$CH$_2$OR", —(CH$_2$)$_n$CONHR", —(CH$_2$)$_n$CH$_2$NHR" and (CH$_2$)$_n$COX, wherein n represents an integer from 0 to 20 inclusive;

R" is selected from the group consisting of H, alkyl, aryl and acyl; and

X is selected from the group consisting of Y, OY' and NY"Y'"

wherein Y is selected from the group consisting of H, alkyl, alkenyl, alkynyl, aryl, heteroaryl, aralkyl, heteroaralkyl and carbohydrate; Y' is selected from the group consisting of H, alkyl, alkenyl, alkynyl, aryl, heteroaryl, aralkyl, heteroaralkyl and carbohydrate; and Y" and Y'" are independently selected from the group consisting of H, alkyl, alkenyl, alkynyl, aryl, heteroaryl, aralkyl, heteroaralkyl and acyl;

wherein each of alkyl, alkenyl, alkynyl, aryl, heteroaryl, aralkyl, heteroaralkyl and acyl may be optionally substituted, provided that R is not methyl.

In a preferred embodiment, n is 0–12 such as 0–6 or 1–6.

Still a further aspect of the invention provides a method of treating an inflammatory disease or condition in a subject in need thereof, comprising administering to said subject a treatment effective amount of a phosphotetrahydropyran of formula (I) (wherein R has the meaning above and can also be H or $CH_3$) or pharmaceutically acceptable salt, derivative or prodrug thereof.

In still yet another aspect of the invention, there is provided a composition comprising a phosphotetrahydropyran of formula (I) (wherein R has the meaning above and can also be H or $CH_3$) together with a pharmaceutically acceptable carrier, diluent or excipient.

The invention also provides for the use of a phosphotetrahydropyran of formula (I) (wherein R has the meaning above and can also be H or $CH_3$) in the manufacture of a medicament for the treatment of an inflammatory disease or condition.

DETAILED DESCRIPTION OF THE INVENTION

Figure 1:
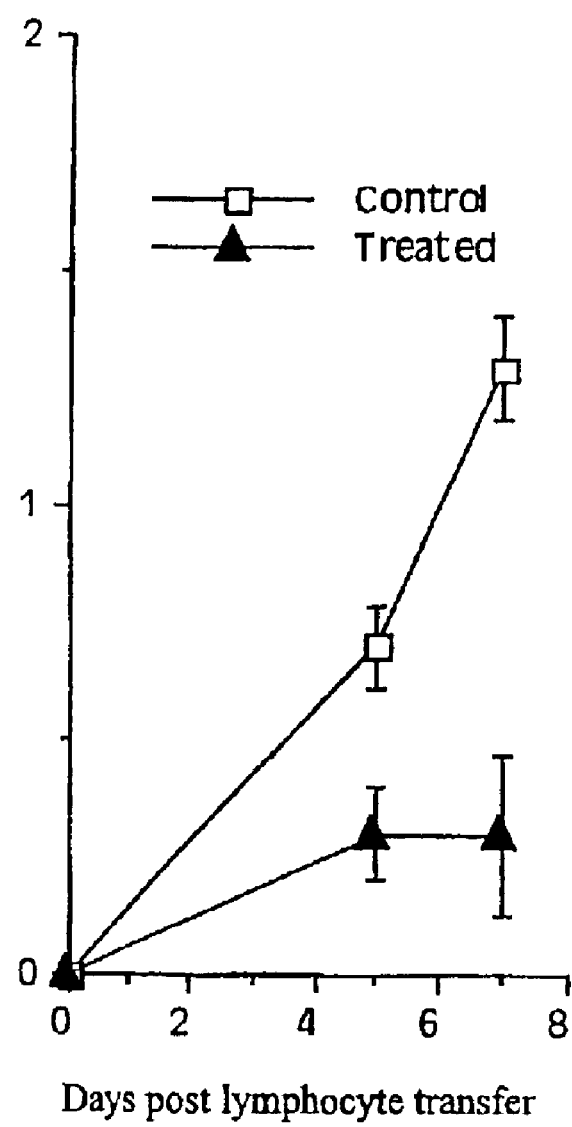
FIG. 1 graphically depicts the effect of phosphoric acid mono-(6-propyl 3,4,5-trihydroxy-tetrahydropyran-2-ylmethyl)ester delivered at a dose of 25 mg/kg/day on passively transferred adjuvant induced arthritis.

As used herein the term "alkyl", denotes straight chain, branched or cyclic fully saturated hydrocarbon residues. Unless the number of carbon atoms is specified the term preferably refers to $C_{1-20}$ alkyl. When "alkyl" groups are used in a generic sense, eg, "propyl," "butyl", "pentyl" and "hexyl" etc, it will be understood that each term may include all isomeric forms (straight, branched or cyclic) thereof. Preferred alkyl are $C_{1-18}$ alkyl, more preferably, $C_{1-6}$ alkyl. Examples of straight chain and branched $C_{1-6}$ alkyl include methyl, ethyl, n-propyl, isopropyl, n-butyl, sec-butyl, tert-butyl, n-pentyl, iso-pentyl, 1,2-dimethylpropyl, 1,1-dimethylpropyl, n-hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl. Other alkyl groups include heptanyl, octanyl, nonanyl, decanyl, undecanyl, dodecanyl, tridecanyl, tetradecanyl, pentadecanyl, hexadecanyl, heptadecanyl, octadecanyl, nonadecanyl and icosanyl. Examples of cyclic alkyl include cyclopropyl, cyclobutyl, cyclopentyl, cyclohexyl, cycloheptyl.

Optionally, the alkyl group can be further substituted by one or more substituents and thus, "alkyl" as used herein is intended to refer to optionally substituted alkyl groups. Suitable substituents may include: alkyl itself (so as to form further lengthened or branched chains) halo (fluoro, chloro, bromo or iodo); haloalkyl, eg trifluoromethyl, trichloromethyl; hydroxy; mercapto; phenyl; benzyl; amino; alkylamino; dialkylamino; arylamino; heteroarylamino; alkoxy, eg, methoxy, ethoxy, butoxy, propoxy; aryloxy, eg phenoxy; benzyloxy; thio; alkylthio eg methyl thio, ethyl thio; acyl, eg acetyl; acyloxy, eg acetoxy; carboxy ($CO_2H$); $CO_2$alkyl; carboxyamide, eg CONHalkyl CON(alkyl)$_2$, CONHaryl, CON(aryl)$_2$; cyano, $OPO_3H_2$, OC(O)alkyl, NHC(O)alkyl, O-carbohydrate or keto (where a $CH_2$ group of an alkyl chain or ring is replaced by C=O). "Alkyl" when used as part of a substituent term, eg $CO_2$alkyl, may also be further substituted as described herein, as may aryl, aralkyl, phenyl and benzyl.

The terms "alkoxy" and "acyloxy" refer to alkyl and acyl groups respectively when linked by oxygen.

As used herein the term "alkenyl" denotes groups formed from straight chain, branched or cyclic hydrocarbon residues containing at least one carbon-carbon double bond including ethylenically mono-, di- or poly-unsaturated alkyl or cycloalkyl groups as previously defined. Unless the number of carbon atoms is specified the term preferably refers to $C_{2-20}$ alkenyl. Examples of alkenyl include ethenyl, propenyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1–4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. Particularly preferred alkenyl are $C_{2-10}$alkenyl, more preferably $C_{2-6}$ alkenyl. Preferred alkenyl are straight chain or branched alkenyl. Alkenyl may optionally be substituted by the optional substituents described above for alkyl, and therefore, "alkenyl" is also intended to refer to optionally substituted alkenyl.

As used herein the term "alkynyl" denotes groups formed from straight chain, branched or cyclic hydrocarbon residues containing at least one carbon-carbon triple bond including ethynically mono-, di- or poly- unsaturated alkyl or cycloalkyl groups as previously defined. Unless the number of carbon atoms is specified the term preferably refers to $C_{2-20}$ alkynyl. Examples include ethynyl, 1-propynyl, 2-propynyl, and butynyl isomers, and pentynyl isomers. Particularly preferred alynyl are $C_{2-10}$ alkynyl, more preferably $C_{2-6}$ alkynyl. Preferred alkynyl are straight chain or branched alkynyl. Alkynyl may optionally be substituted by the optional substituents described above for alkyl. Alkynyl may optionally be substituted by the optional substituents described above for alkyl, and therefore, "alkynyl" is also intended to refer to optionally substituted alkynyl.

The term "acyl" denotes straight chain or branched alkanoyl (C(O)alkyl), alkenoyl (C(O)alkenyl) alkynoyl (C(O)alkynyl) or aroyl (C(O)aryl) and may include groups such as ethanoyl (acetyl), propanoyl, n-butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, propenoyl, butenoyl, pentenoyl, palmitoyl, oleoyl, lineoyl and benzoyl. The hydrocarbon chains of acyl may be further substituted by one or more substituents as described above and therefore, "acyl" is also intended to refer to optionally substituted acyl.

The term "aryl" denotes single, polynuclear, conjugated or fused residues of aromatic hydrocarbon ring systems. Examples of aryl include phenyl, biphenyl and naphthyl. An aryl group may be optionally substituted by one or more optional substituents as herein defined. Accordingly, "aryl" as used herein is taken to refer to aryl that may be optionally substituted.

The term "heteroaryl" denotes single, polynuclear, conjugated or fused aromatic heterocyclic ring systems, wherein one or more carbon atoms of a cyclic hydrocarbon residue is substituted with a heteroatom to provide an aromatic residue. Where two or more carbon atoms are replaced, this may be by two or more of the same heteroatom or by different heteroatoms. Suitable heteroatoms include O, N, S and Se. Examples of heteroaryl include pyridyl, 4-phenylpyridyl, 3-phenylpyridyl, thienyl, furyl, pyrrolyl, indolyl, imidazolyl, oxazolyl, oxadiazolyl, tetrazolyl, pyridazinyl, pyrazolyl, pyrazinyl, thiazolyl, pyimidinyl, quinolinyl, isoquinolinyl, benzofuranyl, benzothienyl, purinyl, quinazolinyl, phenazinyl, acridinyl, benoxazolyl, benzothiazolyl and the like. A heteroaryl group may be optionally substituted by an optional substituent as hereinbefore defined.

As used herein the term "carbohydrate" denotes simple saccharides, including mono-, di- and tri-saccharides, with the point of attachment being through the reducing terminus, ie through a glycosidic linkage, examples of such carbohydrates include 1-glucosyl, 1-mannosyl, 1-galactosyl, 1-maltosyl, 1-lactosyl, 1-isomaltosyl, 1-cellobiosyl, 1-maltotrisoyl, 1-isomaltotriosyl and 1-cellotriosyl.

The term "aralkyl" denoted an alkyl chain substituted (preferably terminally) by an aryl group eg $(CH_2)_n$phenyl wherein n is 1, 2, 3, 4, 5 or 6.

The term heteroaralkyl denotes an alkyl chain substituted (preferably terminally) by a heteroaryl group eg $(CH_2)_n$heteroaryl, wherein n is 1,2,3,4,5 or 6.

The present invention provides compounds having the phosphotetrahydropyran moiety depicted in Formula (I) wherein R may be any of CN, H or C-linked organic residue and may include compounds containing two of the phosphotetrahydropyran moieties depicted in Formula (I) linked by an organic residue. A C-linked organic residue includes a moiety containing at least C, H and optionally one or more of halogen, N, O, P or S.

In one embodiment of the invention, R is H, alkyl, alkenyl, alkynyl, aryl, heteroaryl, aralkyl, heteroaralkyl, cyano or $(CH_2)_n$COX, wherein n represents an integer from 0 to 20 inclusive and X is independently selected from Y, OY' and NY"Y''' wherein Y is independently selected from H, alkyl, alkenyl, alkynyl aryl, heteroaryl, and Y' is independently selected from H, alkyl, akenyl, alkynyl aryl, heteroaryl and carbohydrate, Y" and Y''' are independently selected from alkyl, alkenyl, alkynyl, aryl, heteroaryl or acyl wherein each of alkyl, alkenyl, alkynyl, aryl, heteroaryl, aralkyl, heteroaralkyl and acyl may be optionally substituted.

In one preferred embodiment, R is selected from cyano or the group consisting of —$(CH_2)_nCO_2R'$, —$(CH_2)_n$CHO, —$(CH_2)_nCH_2OR''$, —$(CH_2)_n$CONHR'', —$(CH_2)_nCH_2NHR''$, and —$(CH_2)_n$CONR"R''' wherein n is selected from 0–20, R' is H, alkyl or aryl, R" is H, alkyl, aryl or acyl and R''' is H, alkyl, aryl or acyl. Preferably, n is from 0–12, more preferably 1–6. In another embodiment, R is an alkyl chain (eg $(CH_2)_n$ where n is as above) substituted by OC(O)alkyl, NHC(O)alkyl, $OPO_3H_2$, alkoxy or O-carbohydrate wherein "alkyl" may be substituted as described herein.

Preferred R groups include: cyano; hydroxyalkyl (eg hydroxymethyl, hydroxyethyl, hydroxypropyl, hydroxybutyl, hydroxypentyl, hydroxyhexyl); alkoxyalkyl (eg methoxy- or ethoxy-methyl, ethyl, propyl, butyl, pentyl, hexyl etc); aryloxyalkyl (eg phenoxy-methyl or ethyl); hydroxy-tetrahydro-pyranyloxyalkyl (eg (3,4,5-trihydroxy-6-hydroxymethyl-tetrahydropyran-2-yloxy)- or (3,4-dihydroxy-6-hydroxymethyl-tetrahydropyran-2-yloxy)-methyl, ethyl or propyl); aminoalkyl (eg aminomethyl, aminoethyl, aminopropyl etc); benzyl; phenylethyl; phenyl; 2-, 3- and 4-methoxyphenyl; 2-, 3- and 4-methylphenyl; 2-, 3- and 4-pyridyl; 2-, 4- and 5-pyrimidinyl; 2- and 3-thiophenyl; 2-, 4-, and 5-(1,3)oxazolyl; 2-, 4- and 5-(1,3) thiazolyl; 2- and 4-imidazolyl; 3- and 5-symtriazolyl; —$(CH_2)_nC(O)C_{1-6}$alkyl (eg, n is 0, 1, 2, 3, 4, 5 or 6; and —$C(O)C_{1-6}$alkyl is eg, ethanoyl (acetyl), propanoyl, butanoyl, pentanoyl or hexanoyl); —$(CH_2)_nC(O)$aryl (eg, n is 0, 1, 2, 3, 4, 5 or 6; and —C(O)aryl is eg benzoyl, 2-,3- or 4-chlorobenzoyl, 2-, 3- or 4-methoxybenzoyl or 2-, 3- or 4-methylbenzoyl); —$(CH_2)_nCO_2C_{1-10}$alkyl (eg, n is 0, 1, 2, 3, 4 5, or 6; and —$CO_2C_{1-6}$ alkyl is eg methyl, ethyl, propyl, butyl, pentyl or hexyl ester); —$(CH_2)_nCO_2$aryl (eg, n is 0, 1, 2, 3, 4, 5, or 6; and —$CO_2$aryl is eg phenyl, 2-, 3- or 4-chlorophenyl, 2-, 3- or 4-methoxyphenyl or 2-, 3- or 4-methylphenyl ester); —$(CH_2)$nCONH$C_{1-10}$alkyl (eg n is 0, 1, 2, 3, 4 ,5 or 6; and —CONH$C_{1-10}$alkyl is eg methyl, ethyl, propyl, butyl, pentyl or hexyl amide); —$(CH_2)_n$CONHaryl (eg n is 0, 1, 2, 3, 4 ,5 or 6; and —CONHaryl is eg phenyl, 2-, 3- or 4-chlorophenyl, 2-, 3- or 4-methoxyphenyl or 2-, 3- or 4-methylphenyl amide); —$(CH_2)$nCON$(C_{1-10}$alkyl$)_2$ (eg n is 0, 1, 2, 3, 4 , 5 or 6; and —CON$(C_{1-10}$alkyl$)_2$ is eg dimethyl, diethyl, dipropyl, dibutyl, dipentyl or dihexyl amide).

The skilled person will recognise that a nitrile group is at the same oxidation level as a carboxylic acid or amide group and can be converted into these groups by known means, for example, by treatment with strong aqueous acid or base. Carboxylic acid groups can be esterified by known procedures, for example, treatment with an appropriate alcohol under acidic conditions or by treatment with a suitable alkyl halide. Carboxylic acids can also be reduced by one oxidation level to form aldehydes which in turn can be reduced a further oxidation level to provide alcohols. Suitable reductive procedures are known in the art and may include treatment with hydride reagents, such as $LiAlH_4$, DIBAL, or borane. Corresponding alcohols can be alkylated or acylated using standard procedures. Suitable alkylating agents may include alkyl halides, eg methyl ethyl and propyl chlorides, bromides and iodides, and dialkyl sulphates such as dimethyl sulphate and diethyl sulphate. Suitable acylating agents include carboxylic acids, chlorides and anhydrides. Carboxylic acids may be converted to amides by treatment with a suitable amine in the presence of a catalyst or coupling agent such as DCC. Amides may also be prepared by treating the acid chloride with a suitable amine. In turn, the amide (or nitrile) can be reduced with a suitable reducing agent eg, $LiAlH_4$, to provide an amine. Acylation or alkylation of the amine can be carried out as described above. Further methods for the interconversion of these groups are described in references such as *Comprehensive OrganicTransformations*, R. Larock, VCH Publishers, 1989, and *Advanced Organic Chemistry*, J. March, Third Edition, Wiley InterScience.

Compounds where R is attached to the pyran ring via a methylene group can be prepared by Wittig-type methodology on mannose itself, using an appropriate triphenylphosphorane for example classical Wittig methodology can incorporate, for groups such as alkyl, alkenyl, alkynyl etc. Example 1 illustrates the incorporation of various $CH_2CO_2$alkyl groups at the 6-position using this methodology. By using standard methodology known in the art, the length of the methylene chain can be increased to provide ethylene, propylene etc.

An alkylene chain can be lengthened by, methods known in the art, for example, Arndt-Eistert synthesis. By this means, an acid chloride can be converted to a carboxylic acid with the insertion of $CH_2$. Thus, a carboxylic acid group can be converted to its acid chloride derivative, for example by treatment with $SO_2Cl_2$. The acid chloride derivative can be reacted with diazomethane to form the diazoketone which can then be treated with $Ag_2/H_2O$ or silver benzoate and triethylamine. The process can be repeated to further increase the length of the alkylene chain. Alternatively, an aldehyde (or keto) group could be subjected to Wittig-type methodology (using eg $Ph_3P=CHCO_2Me$) to produce the $\alpha,\beta$-unsaturated ester. In this case, hydrogenation of the double bond provides the alkylene chain increased by two carbon atoms. In a similar manner, other phosphoranes could be used to generate longer (and optionally substituted, branched or unsaturated) carbon chains.

The skilled person will also recognise that chemical manipulation of the substituent at the 2-position may require protection of other potentially reactive groups, such as the hydroxy groups, within the molecule. Suitable protective groups for use under the appropriate conditions, as well as methods for their installation and removal are known in the art and are described in *Protective Groups in Organic Synthesis*, T. W. Greene and P. Wutz, John Wiley and Son, (1991). These protected derivatives provide a further aspect of the invention.

The term "salt, derivative or prodrug" includes any pharmaceutically acceptable salt, ester, solvate, hydrate or any other compound which, upon administration to the recipient is capable of providing (directly or indirectly) a compound as described herein. However, it will be appreciated that non-pharmaceutically acceptable salts also fall within the scope of the invention since these may be useful in the preparation of pharmaceutically acceptable salts.

Suitable pharmaceutically acceptable salts include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, taninic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The compounds of the invention may be in crystalline form either as the free compounds or as solvates (e.g. hydrates) and it is intended that both forms are within the scope of the present invention. Methods of solvation are generally known within the art.

Any compound that is a prodrug of a compound of formula (I) is within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate, or where a free amino group is converted into an amide. Procedures for acylating the compounds of the invention are well known in the art and may include treatment of the compound with an appropriate carboxylic acid, anhydride or chloride in the presence of a suitable catalyst or base.

T lymphocytes are known to migrate from the blood stream into tissues, including tissues that contain an antigen to which they can respond. An in vivo example of T lymphocyte migration involves the intravenous injection of radioisotopically- or fluorescently-labelled antigen-specific T cells into a mammal that has the antigen present in one or more of its tissues. An assessment of the degree to which the injected T cells have accumulated in the antigen-containing tissue can be made either by measuring the amount of radioactivity present in the tissue or analysing the tissue histologically to determine the number of infiltrated fluorescently labelled cells. To put this into practice, animals are immunised with either a 'self' protein or a foreign protein in the presence of a powerful immunological adjuvant and seven to ten days later their spleens and/or draining lymph nodes are removed and T cells isolated from these organs. These cells are then radio- or fluorescently-labelled and transferred by intravenous injection into a naïve syngeneic animal. In the case of the 'self' protein, some of the antigen-specific T cells will migrate and accumulate in the tissue in which the antigen is located. For example, in the case of a CNS antigen the cells will localise in the brain and spinal cord and the number of labelled cells that have accumulated there can then be determined. In the case of a foreign antigen, the recipient is given a foreign antigen depot (eg insoluble antigen can be injected into a tissue such as the skin) and the cells will accumulate in the site containing the foreign antigen. In practice the simplest way of doing this experiment is to use a cell-mediated type IV hypersensitivity reaction. This method is recognised and well understood by those skilled in the art and the principles of this can be found in many immunology text books for example Immunology $5^{th}$ Edition; Ivan M. Roitt Ed, Blackwell Scientific Publications, Boston, 1998. Here donor animals are sensitised to a self protein (in practice skin is the easiest tissue to use) by chemically modifying the protein(s) in this tissue thereby allowing it to be 'seen' as 'foreign' tissue by the immune system. This is done by reacting the skin with a 'hapten' which is usually an alkylating or arylating agent that reacts covalently with and thereby modifies protein(s) in the skin. Seven to ten days following sensitisation, spleens are taken from the donor animals. T lymphocytes are isolated, radio- or fluorescently-labelled and transferred into naïve recipient animals by intravenous injection. Prior to cell transfer the recipient animals have had a portion of skin, for simplicity's sale usually the ear, treated with the same hapten. Within a short time of cell transfer sensitised T cells begin to accumulate in the haptenised tissue and eight to twenty-four hours later the tissue can be removed and the cell accumulation assessed. In the case of fluorescently-labelled cells their accumulation is assessed histologically and in the case of the radio-labelled cells accumulation is assessed by counting radio active decay in a suitable device. Typically the agents of the present invention can inhibit T cell accumulation in this model by between 20 and 85%. In this model it is crucial to passage a relatively pure T lymphocyte population. The agents of the present invention do not appear to interfere with B lymphocyte migration. Similar experiments can be performed using T cell lines.

Vascular endothelial cells (VEC), when grown in culture will grow to confluence and deposit an endothelial subcellular matrix. The cells and matrix are akin to the same components found in blood vessels (Jaffe, E. A., Nachman, R. L., Becker, C. G. and Minick, C. R., 1973, Culture of human endothelial cells derived from umbilical veins. Identification by morphologic and immunologic criteria. Journal of Clinical Investigation, vol 52(11), 2745–2756; incorporated herein by reference). Activated T cells will migrate through this matrix in the same fashion as they do through tissues in the body. This migration can be studied and put into practice by growing vascular endothelial cells on special devices that contain a fenestrated barrier between two chambers through which cells can move. Thus, when VEC are cultured in the upper chamber of such a device, they will grow to confluence and deposit a subcellular matrix over the fenestrated barrier. If activated T cells are suspended above the endothelial cell layer in this chamber they will migrate through the VEC layer. Once they are below the VEC layer they will degrade the subcellular matrix and migrate through the fenestrations into the lower chamber where the number of accumulated cells can be determined. The efficacy of agents that can inhibit the ability of T cells to migrate through this in vitro vascular system can thus be determined by placing the agent in either or both chambers during the culture period when the T cells are present. Efficacy of the agent is quantified by comparing the number of T cells in the lower chambers (ie migrated cells) of the agent-treated versus the number of T cells in the lower chamber of the control experimental devices. This method is commonly used to study cell migration through vascular endothelium and is well documented in the scientific and medical literature including in the following publications which are incorporated herein by reference (Poggi, A., Costa, P., Socchi, M. R. and Moretta, L., 1997, Phenotypic and functional analysis of CD4+ NKRP1A+ human lymphocytes. Direct evidence that the NKRP1A molecule is involved in transendothelial migration. European Journal of Immunology, vol 27, 2345–2350; Hauzenberger, E., Hauzenberger, D., Hultenby, K. and Holgersson, J., 2000, Porcine endothelium supports transendothelial migration of human leukocyte subpopulations: anti-porcine vascular cell adhesion molecule antibodies as species-specific blockers of transendothelial monocyte and natural killer cell migration.

Transplantation. Vol 69(9):1837–1849; Borthwick, N. J., Akbar, A. N., MacCormac, L. P., Lowdell, M., Craigen, J. L., Hassan, I., Grundy, J. E., Salmon, M. and Yong K. L., 1997, Selective migration of highly differentiated primed T cells, defined by low expression of CD45RB, across human umbilical vein endothelial cells: effects of viral infection on transmigration. Immunology. Vol 90(2), 272–280; Mohle, R., Moore, M. A., Nachman, R. L. and Rafii, S., 1997, Transendothelial migration of CD34+ and mature hematopoietic cells: an in vitro study using a human bone marrow endothelial cell line. Blood. Vol 89(1), 72–80); Lou, J., Gasche, Y., Zheng, L., Giroud, C., Morel, P., Clements, J., Ythier, A. and Grau, G. E., 1999, Interferon-beta inhibits activated leukocyte migration through human brain microvascular endothelial cell monolayer. Laboratory Investigation vol 79(8):1015–1025.

Compounds of the present invention may inhibit, where the term "inhibit" includes its general meaning viz, stopping, preventing, restraining, minimising or slowing, T lymphocyte migration from within the blood vessels into surrounding tissues and therefore may be useful in the therapeutic treatment of cell-mediated inflammatory diseases and conditions. Examples of such inflammatory diseases or conditions which may be treated by the compounds of the present invention include rheumatoid arthritis, multiple sclerosis, acute disseminated encephalomyelitis, psoriasis, Crohn's disease, T cell-mediated dermatitis, stromal keratitis, uveitis, thyroiditis, sialitis and type I diabetes. The term inhibits therefore can also be understood to mean to reverse the progression or severity of symptoms of such diseases. As such, the present method includes both medical therapeutic and/or prophylactic administration, as appropriate.

The compounds of the invention may be used to treat humans or other mammalian subjects. The compounds of the invention are considered to be particularly suitable for the treatment of human subjects. Non-human subjects may include primates, livestock animals (eg. sheep, cows, horses, goats, pigs) domestic companion animals (eg cats, dogs) laboratory test animals (eg mice, rats, guinea pigs, rabbits) or captive wild animals.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular disease or condition being treated.

As used herein, the term "treatment effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 ng to 1 g per kg of body weight per dosage, such as is in the range of 1 mg to 1 g per kg of body weight per dosage Suitably, the dosage is in the range of 1 mg to 500 mg per kg of body weight per dosage, such as 1 mg to 200 mg per kg of body weight per dosage, or 1 mg to 100 mg per kg of body weight per dosage. Other suitable dosages may be in the range of 1 mg to 250 mg per kg of body weight, including 1 mg to 10, 20, 50 or 100 mg per kg of body weight per dosage or 10 mg to 100 mg per kg of body weight per dosage.

Suitable dosage amounts and dosing regimens can be determined by the attending physician and may depend on the particular condition being treated, the severity of the condition, as well as the general health, age and weight of the subject.

The active ingredient may be administered in a single dose or a series of doses. While it is possible for the active ingredient to be administered alone, it is preferable to present it to a subject as a composition, preferably as a pharmaceutical composition. The formulation of such compositions are well know to those skilled in the field. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include supplementary anti-inflammatory or other physiologically active agents where appropriate.

The carrier, diluent or excipient must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions for topical administration, for example, dermally, may be in the form of lotions, creams, pastes, gels, ointments and the like Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The compounds of the invention may also be presented for use in veterinary compositions. These may be prepared by any suitable means known in the art. Examples of such compositions include those adapted for:

(a) oral administration, external application (eg drenches including aqueous and non-aqueous solutions or suspensions), tablets, boluses, powders, granules, pellets for admixture with feedstuffs, pastes for application to the tongue;

(b) parenteral administration, eg subcutaneous, intramuscular or intravenous injection as a sterile solution or suspension (c) topical application eg creams, ointments, gels, lotions etc Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following non-limiting examples which are included for the purpose of illustrating the invention and are not intended to limit the generality hereinbefore described.

EXAMPLES

In the following examples temperatures were measured in degrees Celsius and thin layer chromatograms (tlc) were determined on silica gel plates and unless otherwise specified chemical reagents were purchased from Aldrich.

Example 1

Preparation of methyl, ethyl, pentyl and phenylethyl (3,4,5-trihydroxy-6-phosphonooxymethyl-tetrahydro-pyran-2-yl)-acetic acid ester (Formula I; R=$CH_2$COOY'; Y'=—$CH_3$, —$CH_2CH_3$, —$(CH_2)_4CH_3$ and —$CH_2CH_2$Ph respectively)

D-mannose (3.6 g, 20 mmol) and carboxymethylene triphenylphosphorane (6.68 g, 20 mmol) prepared by the method of von Isler et al., (von Isler, O., Gutmann, H., Montavon, M., Ruegg, R., Ryser, G. and Zeller, P., (1957).

Synthesen in der carotinoid-Reihe. Anwendung der Wittig-reaktion zur synthese von estern des bixins und crocetins. Helvetica Chimica Acta, vol 15, 1242–1249, incorporated herein by reference) was refluxed in dioxane (75 mls) for 3 hours. Afterwards the dioxane was removed under reduced pressure and diethyl ether (250 ml) was added to the oily residue, whereupon it solidified. This was stirred vigorously for 20 minutes, allowed to settle and the ether was decanted. The washing procedure was repeated with a further 250 ml of ether. The solid was then stirred vigorously with dichloromethane (100 ml) for 15 minutes and the solid filtered off and dried to give methyl 4,5,6,7,8-pentahydroxyoct-2-eneoate (3.8 g, 80%). This material (16.0 g, 67.8 mmol) was dissolved in methanol (160 ml), to this solution was added dry Dowex 1 ion exchange resin (OH⁻ form; 48 g), and the mixture allowed to stir for 4 hours at room temperature. The Dowex was filtered through a sintered glass funnel to remove the resin, which was washed with methanol (2×50 ml) and the combined filtrate and washings evaporated under reduced pressure to give methyl (3,4,5-trihydroxy-6'-hydroxymethyl)pyran-2-yl)acetate as a pale yellow syrup. A mixture of this material (417 mg, 1.77 mmol), trityl chloride (740 mg, 2.66 mmol) and pyridine (5 ml) was stirred at 60° for 8 hours. After cooling to room temperature acetic anhydride (1 ml, 10.6 mmol) was added and the mixture stirred overnight, whereupon it was added to ice cold water (25 ml) and extracted with chloroform (3×50 ml). The organic phase was dried (sodium sulfate), filtered and evaporated under reduced pressure. The residue was chromatographed on a silica gel (0.063–0.2 mm) column (2×30 cm), eluted with petroleum spirit (bp 60–80°): ethyl acetate (2:1) to give methyl (3,4,5-triacetoxy-6-trityloxymethyl-tetrahydropyran-2-yl)-acetic acid ester (786 mg). This compound (786 mg) was stirred at room temperature with anhydrous ferric chloride (257 mg) in dichloromethane (10 ml) for 2 hours, whereupon water (10 ml) was added and the mixture extracted with chloroform (3×25 ml). The organic extracts were combined and dried (sodium sulfate), filtered and the filtrate evaporated under reduced pressure. The residue was chromatographed on a silica gel (0.063–0.2 mm) column (2×30 cm), eluted with petroleum spirit (bp 60–80°): ethyl acetate (1:2) to give methyl (3,4,5-triacetoxy-6-hydroxymethyl-tetrahydro-pyran-2-yl)-acetic acid ester (463 mg). This compound (344 mg, 0.95 mmol) was dissolved in toluene (15 ml) and pyridine (86.7 mg) and the mixture cooled to 0° whereupon phosphorus oxychloride (167.8 mg, 1.094 mmol) was added dropwise with stirring under a dry nitrogen atmosphere. The mixture was allowed to come to room temperature and stirred for 2 hours. The mixture was filtered and evaporated to dryness under reduced pressure. The residue was dissolved in a 1:1 mixture of acetone and water (10 mls) and kept at 45–50° for 2 hours. After evaporation to dryness the residue was evaporated once from 15 ml of each of ethanol, methanol and finally acetone to give methyl (3,4,5-triacetoxy-6-phosphonooxymethyl-tetrahydro-pyran-2-yl)-acetic acid ester (354 mg, 81%). This compound (354 mg, 0.8 mmol) was stirred at room temperature over night in methanol (5 ml) that contained sodium methoxide (86.4 mg, 1.6 mmol). After taking to dryness under reduced pressure the residue was dissolved in water (5 ml) and treated with a strong cationic exchange resin (Dowex 50 H⁺ form) to remove sodium ions. The resulting solution was filtered, taken to dryness under reduced pressure and the residue evaporated twice from ethanol and twice from methanol to give methyl (3,4,5-trihydroxy-6-phosphonooxymethyl-tetrahydro-pyran-2-yl)-acetic acid ester (203 mg, 80%) ESMS (−ve) 315 (M−H).

In a similar manner were made the following:

Ethyl (3,4,5-trihydroxy-6-phosphonooxymethyl-tetrahydro-pyran-2-yl)-acetic acid ester (80%) ESMS (−ve) 329 (M−H).

Phenylethyl (3,4,5-trihydroxy-6-phosphonooxymethyl-tetrahydro-pyran-2-yl)-acetic acid ester (64%).

Pentyl (3,4,5-trihydroxy-6-phosphonooxymethyl-tetrahydro-pyran-2-yl)-acetic acid ester (65%), ESMS (−ve) 371 (M−H).

The monosodium salts of these esters were readily prepared by treating a concentrated ethanolic solution of the phosphate with 1.2 equivalents of anhydrous sodium acetate whereupon the desired salt precipitated, was washed with a small volume of ethanol and dried to give the following Methyl (3,4,5-trihydroxy-6-phosphonooxymethyl-tetrahydro-pyran-2-yl)-acetic acid ester sodium salt (92%)

Ethyl (3,4,5-trihydroxy-6-phosphonooxymethyl-tetrahydro-pyran-2-yl)-acetic acid ester sodium salt (80%), $^1$Hnmr (500 MHz, $D_2O$): δ 1.10 (t, J=7.5 Hz, 3H) 2.71–2.81 (m, 2H), 3.48–3.54 (m, 1H), 3.63–3.69 (m, 1H), 3.79–3.93 (m, 2H), 3.95–3.99 (m, 1H), 4.02 (q, J=7.5 Hz, 2H), 4.11–4.16 (m, 1H), 4.20–4.26 (m, 1H).

Phenylethyl (3,4,5-trihydroxy-6-phosphonooxymethyl-tetrahydro-pyran-2-yl)-acetic acid ester sodium salt (93%)

Pentyl (3,4,5-trihydroxy-6-phosphonooxymethyl-tetrahydro-pyran-2-yl)-acetic acid ester sodium salt (70%). $^1$Hnmr (500 MHz, $D_2O$): δ 1.08–1.15 (m, 3H) 2.39–2.67 (m, 8H), 3.51–4.08 (m, 9H).

Example 2

Preparation of (3,4,5-trihydroxy-6-phosphonooxymethyl-tetrahydro-pyran-2-yl)-acetic acid (Formula I; R=—$CH_2COOH$) disodium salt Ethyl (3,4,5-trihydroxy-6-phosphonooxymethyl-tetrahydro-pyran-2-yl)-acetic acid ester sodium salt (prepared in Example 1) (352 mg, 1.0 mmol) was dissolved in water (5 ml) and treated with sodium hydroxide (80 mg, 2 mmol) dissolved in water (1 ml). After stirring at room temperature overnight the mixture was treated with Amberlite IR 120 cation exchange resin (H⁺ form) to remove sodium ions, the solution was filtered and evaporated to dryness under reduced pressure to give (3,4,5-trihydroxy-6-phosphonooxymethyl-tetrahydro-pyran-2-yl)-acetic acid (220 mg, 73%). This was dissolved in water (1 ml) and sodium methoxide (79 mg, 1.46 mmol) in methanol (1 ml) was added and the mixture was stirred briefly and added dropwise with stirring to ethanol (50 ml). The resulting suspension was centrifuged and the overlying liquid decanted. The pelleted material at the bottom of the centrifuge tube was resuspended in fresh ethanol 25 ml and centrifuged. After decanting the overlying liquid the pellet was dried under vacuum to give (3,4,5-trihydroxy-6-phosphonooxymethyl-tetrahydro-pyran-2-yl)-acetic acid disodium salt (200 mg, 79%).

This compound can also be prepared in the following manner. (3,4,5-Triacetoxy-6-acetoxymethyl-tetrahydro-pyran-2-yl)-acetic acid (from Example 10) (8.02 g, 20.6 mmol) was dissolved in dry methanol (60 ml) and sodium methoxide (1.6 g) was added. The reaction was followed by thin layer chromatography and after 2.5 hour Dowex 50W X8 H⁺ form ion exchange resin was added and after a further 30 min the reaction mixture was filtered and the solvent removed. To this impure material (4.95 mg, 12.5 mmol) in pyridine (70 ml) was added trityl chloride (~2.5 eq, 17.8 g)

and the mixture stirred at 50° overnight. After cooling to room temperature acetic anhydride (~10 eq, 24 ml) was added and the mixture stirred for 2.5 hours, whereupon it was added to ice cold water (200 ml) and extracted with dichloromethane (3×200 ml). The organic phase was dried (sodium sulfate), filtered and evaporated under reduced pressure. The residue was adsorbed on ~30 g silica gel, placed on a column (70×140 mm) of silica gel (50 g), and eluted under vacuum with 5% ethyl acetate/light petroleum (800 ml, f1), 25% ethyl acetate/light petroleum (800 ml, f2 [400 ml], f3 [400 ml]), 100% ethyl acetate (400 ml, f4) and 25% methanol/dichloromethane (400 ml, f5). The product acetic acid 7-acetoxy-2-oxo-5-trityloxymethyl-hexahydro-furo[3,2-b]pyran-6-yl ester was found in f4 (5.87 g, 54%). This material (5.87 g, 11.1 mmol) was stirred at room temperature with anhydrous ferric chloride (3.67 g) in dichloromethane (100 ml) for 1.5 hours, whereupon water (100 ml) was added and the mixture extracted with dichloromethane (2×100 ml). The organic extracts were combined and dried (sodium sulfate), filtered and the filtrate evaporated under reduced pressure. The residue was adsorbed on ~15 g silica gel, placed on a column (40×90 mm) of silica gel (20 g) and eluted under vacuum with 50% ethyl acetate/light petroleum (400 ml, f1), 10% methanol/dichloromethane (400 ml, f2) and 100% methanol (200 ml, f3). The product acetic acid 7-acetoxy-5-hydroxymethyl-2-oxo-hexahydro-furo[3,2-b]pyran-6-yl ester was found in f2 (2.29 g, 72%). This compound (2.11 g, 7.33 mmol) was dissolved in dichloromethane (40 ml) and pyridine (0.70 g) and the mixture cooled to 0° whereupon phosphorus oxychloride (1.1 eq, 1.4 g) was added dropwise with stirring under a dry nitrogen atmosphere. The mixture was allowed to warm to room temperature and stirred for 6 hours. The mixture was filtered and evaporated to dryness under reduced pressure. The residue was dissolved in a 1:1 mixture of acetone and water (50 ml) and kept at 45–50° for 2 hours. After evaporation to dryness the residue was evaporated from 50 ml of ethanol. This material was stirred at room temperature over night in water (50 ml) that contained sodium methoxide (~5 eq, 2.0 g), after which it was treated with a strong cationic exchange resin (Dowex 50W H$^+$ form) to remove sodium ions. The ion exchange resin was filtered off and the filtrate taken to dryness under reduced pressure and the residue evaporated from ethanol (50 ml). This material was then dissolved in a minimum of water and added dropwise to a solution of sodium acetate (0.9 g) in ethanol (300 ml). The resulting precipitate was pelleted by centrifugation and the ethanol decanted off, the solid was washed with diethyl ether (2×100 ml) and dried to give (3,4,5-trihydroxy-6-phosphonooxymethyl-tetrahydro-pyran-2-yl)-acetic acid monosodium salt (2.26 g, 95%). $^1$Hnmr (500 MHz, D$_2$O): δ 2.48–2.62 (m, 2H), 2.88 (dd, J=4.0, 17.5 Hz, 1H), 3.41–3.46 (m, 1H), 3.50–3.60 (m, 2H), 3.95–4.04 (m, 1H); ESMS (−ve) 301 (M−H).

Example 3

Preparation of phosphoric acid mono-(6-allyl-3,4,5-trihydroxy-tetrahydro-pyran-2-ylmethyl) ester (Formula I; R=—CH$_2$CH=CH$_2$) and phosphoric acid mono-(6-propyl-3,4,5-trihydroxy-tetrahydro-pyran-2-ylmethyl)ester (Formula I; R=—(CH$_2$)$_2$CH$_3$)

2-Allyl-6-hydroxymethyl-tetrahydropyran-3,4,5-triol (962 mg, 4.72 mmol) prepared by the method of Giannis and Sandhoff (*Tetrahedron Letters*, 1985, 26, 1479–1482; incorporated herein by reference) was dissolved in pyridine (10 ml). To this solution was added trityl chloride (2.6 g, 9.4 mmol) and the mixture stirred for 24 hours at 40° C. Acetic anhydride (2.0 ml, 21 mmol) was added and the mixture stirred for a further 18 hours whereupon it was poured into ice cold water (50 ml) and this was extracted with chloroform (3×50 ml). The combined chloroform extracts were washed with water (50 ml), dried (sodium sulfate), filtered and taken to dryness under reduced pressure. The residue was chromatographed on a silica gel (0.063–0.2 mm) column (2×40 cm), eluted with petroleum spirit (bp 60–80°): ethyl acetate (4:1) to give acetic acid 4,5-diacetoxy-6-allyl-2-trityloxymethyl-tetrahydropyran-3-yl ester (1.9 g, 70%). This compound (1.9 g, 3.32 mmol) and dry ferric chloride (1.2 g) were stirred at room temperature in dichloromethane (25 ml) for 2 hours. Water was added to the reaction mixture and this was extracted with chloroform (3×50 ml). The combined chloroform extracts were washed with water (50 ml), dried (sodium sulfate) filtered and evaporated to dryness under reduced pressure. The residue was chromatographed on a silica gel (0.063–0.2 mm) column (2×30 cm), eluted with petroleum spirit (bp 60–80°): ethyl acetate (1:1) to give acetic acid 4,5-diacetoxy-6-allyl-2-hydoxymethyl-tetrahydropyran-3-yl ester (900 mg, 82%). This compound (900 mg, 2.23 mmol) and pyridine (237 mg, 3.0 mmol) were dissolved in toluene (15 ml), to this solution under a nitrogen atmosphere at 0° C. was added phosphorus oxychloride (460 mg, 2.9 mmol) dropwise with stirring. After the addition the mixture was allowed to come to room temperature and stir for 2 hours. The reaction was filtered and evaporated to dryness under reduced pressure. The residue was dissolved in a 1:1 mixture of acetone (10 ml) and water (10 ml) and heated at 50 to 60° for 2 hours. The mixture was taken to dryness under reduced pressure and the residue evaporated once each from ethanol, methanol and acetone (25 ml) to give acetic acid 4,5-diacetoxy-6-allyl-2-phosphonooxymethyl-tetrahydro-pyran-3-yl ester (851 mg, 76%). This compound (851 mg, 2.08 mmol) was dissolved in methanol (10 ml) to this was added sodium methoxide (247 mg, 4.57 mmol) in methanol (5 ml) and the mixture stirred for 2 hours at room temperature. The mixture was taken to dryness under reduced pressure and the residue dissolved in water (10 ml) and treated with cation exchange resin (Dowex 50 H$^+$ form) to remove sodium ions. After filtration the mixture was taken to dryness to give phosphoric acid mono-(6-allyl-3,4,5-trihydroxy-tetrahydro-pyran-2-ylmethyl) ester (580 mg, 98.5%). This compound (580 mg, 2.04 mmol) was dissolved in water (1.0 ml) and sodium acetate (168 mg, 2.05 mmol) in methanol (5 ml) was added. A further amount of water (1.0 ml) was added and the resulting mixture was added dropwise with stirring to ethanol (50 ml). The resulting precipitate was isolated by centrifugation to give phosphoric acid mono-(6-allyl-3,4,5-trihydroxy-tetrahydro-pyran-2-ylmethyl) ester mono sodium salt (480 mg, 76.3%), $^1$Hnmr (500 MHz, D$_2$O): δ 2.16–2.30 (m, 1H), 2.34–2.48 (m, 1H), 3.46–3.54 (m, 1H) 3.62–3.94 (m, 6H), 4.95–5.08 (m, 2H), 5.62–5.76 (m, 1H); ESMS (−ve) 283 (M−H). This compound (284 mg, 1 mmol) was dissolved in methanol (25 ml) stirred under a hydrogen atmosphere in the presence of 10% palladium on charcoal until uptake of hydrogen ceased. The catalyst was removed by filtration and the filtrate taken to dryness under reduced pressure to give phosphoric acid mono-(6-propyl-3,4,5-trihydroxy-tetrahydro-pyran-2-ylmethyl) ester (quantitative). From this compound, in a similar manner to the allyl compound above, was prepared phosphoric acid mono-(6-propyl-3,4,5-trihydroxy-tetrahydro-pyran-2-ylmethyl) ester mono sodium salt (79%), ESMS (−ve) 285 (M−H).

Example 4

Phosphoric acid mono-(3,4,5-trihydroxy-tetrahydro-pyran-2-yl methyl) ester Formula I; R=H) mono sodium salt A stirred solution of 2,3,4,6-tetra-O-acetyl-D-mannopyranosyl bromide (3.96 g, 9.64 mmol; prepared by the method Levene and Tipson (Levene, P. A. and Tipson, R. S., (1931) *Journal of Biological Chemistry*, vol 90, p 89–98.; incorporated herein by reference) tributyltin hydride (4.32 g, 1.3 eq) and AIBN (280 mg, 0.2 eq) in dry toluene (75 ml) was heated to 80° C. for 2.5 hours. Upon cooling the reaction mixture was filtered through a plug of silica which was then washed with 20% methanol in dichloromethane (200 ml). The solvent was removed from the combined filtrate and washings to give crude product which was purified on a flash silica column (50 g, 3.5×60 cm) eluting with 100% light petroleum (500 ml) f1—5% ethyl acetate in light petroleum (500 ml) f2—10% ethyl acetate in light petroleum (500 ml) f3,4—25% ethyl acetate in light petroleum (400 ml) f5—50% ethyl acetate in light petroleum (400 ml) f6—100% ethyl acetate (400 ml) f7—10% methanol in dichloromethane (400 ml) f8—4,5-Diacetoxy-2-acetoxymethyl-tetrahydro-pyran-3-yl acetic acid ester was isolated from f6 (3.16 g, 99%). To a stirred solution of this compound (3.16 g, 9.52 mmol) in dry methanol (40 ml) was added sodium methoxide (101 mg). The reaction was monitored by tlc and upon completion the solvent was removed to give 2-hydroxymethyl-tetrahydro-pyran-3,4,5-triol (1.76 g). This compound (1.76 g, 8.54 mmol) was tritylated and acetylated in a similar manner to 2-allyl-6-hydroxymethyl-tetrahydropyran-3,4,5-triol in Example 3 above to give 4,5-diacetoxy-2-trityloxymethyl-tetrahydro-pyran-3-yl acetic acid ester (2.0 g, 35%). This compound was purified on a rapid vacuum silica column (40 g, 7×13 cm) eluted with 100% light petroleum (700 ml) f1—5% ethyl acetate in light petroleum (1000 ml) f2,3—25% ethyl acetate in light petroleum (700 ml) f4—100% ethyl acetate (500 ml) f5—10% methanol in dichloromethane (500 ml) f6. The product was isolated from f4. This compound was detritylated as before to give 4,5-diacetoxy-2-hydroxymethyl-tetrahydro-pyran-3-yl acetic acid ester (81%). Phosphorylation as before gave 4,5-diacetoxy-2-phosphonooxymethyl-tetrahydro-pyran-3-yl acetic acid ester (96%). This compound (980 mg, 2.65 mmol) was dissolved in methanol (20 ml) and stirred with sodium methoxide (364 mg, 2.5 eq.) at room temperature for 1 hour. The mixture was evaporated to dryness under reduced pressure and the residue was dissolved in water (20 ml) and this was washed through a cation exchange column to remove sodium ions. The resin was washed with additional water (2×10 ml) and the combined water washings were taken to dryness under reduced pressure. The residue was dissolve in a minimum of water and added slowly to a solution of sodium acetate (239 mg, 1.1 eq) in ethanol (100 ml). The resulting precipitate was collected by centrifugation and dried to give mono-(3,4,5-trihydroxy-tetrahydro-pyran-2-ylmethyl)phosphoric acid ester mono sodium salt (500 mg, 71%). $^1$Hnmr (500 MHz, D$_2$O): δ 3.25 (ddd, J=1.5, 5.5, 9.5 Hz, 1H), 3.47–3.54 (m, 3H), 3.78 (dd, J=2.0, 12.5 Hz, 1H), 3.81–3.85 (m, 1H), 3.86 (dd, J=5.5, 11.5 Hz, 1H), 3.95 (ddd, J=2.0, 5.5, 12.0 Hz, 1H); ESMS (−ve) 243 (M−H).

Example 5

Preparation of 6-cyano-3,4,5-trihydroxy-tetrahydro-pyran-2-ylmethyl)phosphoric acid ester (Formula I; R=CN) and its disodium salt To a stirred solution of 2,3,4,6-tetra-O-acetyl-D-mannopyranosyl bromide (9.28 g, 22.6 mmol) (prepared as described in Example 4 above) in nitromethane (50 ml) was added mercuric cyanide (5.81 g, 1.0 eq). The reaction mixture was monitored by tlc and after two days filtered through celite, the celite was washed with nitromethane (2×30 ml) and the solvent removed. The residue was taken up in chloroform (60 ml) and washed with sodium bromide solution (1M, 3×20 ml), water (30 ml), dried (sodium sulfate) and the sodium bromide solution (1M, 3×20 ml), water (30 ml), dried (sodium sulfate) and the solvent removed under reduced pressure. The residue was purified on a flash silica column (50 g, 3.5×60 cm) eluted with 100% light petroleum (300 ml)—10% ethyl acetate in light petroleum (400 ml) f1—25% ethyl acetate in light petroleum (400 ml) f2,3—50% ethyl acetate in light petroleum (400 ml) f4—100% ethyl acetate (400 ml) f5—20% methanol in dichloromethane (400 ml) f6. 4,5-Diacetoxy-2-acetoxymethyl-6-cyano-tetrahydro-pyran-3-yl acetic acid ester was isolated from f3 (2.53 g, 31%). To a stirred solution of this compound (2.17 g, 6.1 mmol) in dry methanol (35 ml) was added sodium methoxide (46 mg). The reaction was monitored by tlc and upon completion the solvent was removed to give 3,4,5-trihydroxy-6-hydroxymethyl-tetrahydro-pyran-2-carbonitrile (1.38 g, 79%). This compound (1.38 g, 6.77 mmol) was tritylated, acetylated, detritylated, phosphorylated and deacetylated as described in Example 3 above to give 6-cyano-3,4,5-trihydroxy-tetrahydro-pyran-2-ylmethyl phosphoric acid ester and this was converted to the disodium salt to give 6-cyano-3,4,5-trihydroxy-tetrahydro-pyran-2-ylmethyl phosphoric acid ester disodium salt (72%). $^1$Hnmr (500 MHz, D$_2$O): δ 3.56–3.65 (m, 1H), 3.70–3.96 (m, 3H), 4.00–4.16 (m, 2H), 4.21–4.30 (m, 1H); ESMS (−ve) 268 (M−H).

Example 6

Preparation of 6-phenyl- (Formula I; R=—C$_6$H$_5$), 6-(4'-methoxyphenyl)- (Formula I; R=—C$_6$H$_4$OCH$_3$), 6-(2'-pyridyl)- (Formula I; R=2-pyridyl), 6-pentyl- (Formula I; R=—(CH$_2$)$_4$CH$_3$) and 6-phenylethyl- (Formula I; R=—CH$_2$CH$_2$Ph) 3,4,5-trihydroxy-tetrahydro-pyran-2-ylmethyl phosphoric acid ester and their sodium salts 6-Phenyl-2-hydroxymethyl-tetrahydro-pyran-3,4,5-triol was prepared from 2,3,4,6-tetra-O-acetyl-D-mannopyranosyl bromide according to the method of Hurd and Holysz (Hurd, C. D. and Holysz, R. P., (1950). Reactions of polyacylglycosyl halides with Grignard reagents. J. Am. Chem Soc., 1950, vol 72, 1732–1738) incorporated herein by reference. This compound (2.4 g, 10 mmol) was tritylated, acetylated in the same manner as described for to 2-allyl-6-hydroxymethyl-tetrahydropyran-3,4,5-triol in Example 3 to give acetic acid 4,5-diacetoxy-6-phenyl-2-trityloxymethyl-tetrahydro-pyran-3-yl ester (3.1 g, 64%). This compound was detritylated, phosphorylated and deacetylated as described for acetic acid 4,5-diacetoxy-6-allyl-2-trityloxymethyl-tetrahydropyran-3-yl ester in Example 3 above to give 6-phenyl-3,4,5-trihydroxy-tetrahydro-pyran-2-ylmethyl phosphoric acid ester (22% overall yield) ESMS (−ve) 319 (M−H).

In a similar manner were made the following:

6-(4'-methoxyphenyl)-3,4,5-trihydroxy-tetrahydro-pyran-2-ylmethyl phosphoric acid ester (18% overall yield) ESMS (−ve) 349 (M−H).

6-(2'-pyridyl)-3,4,5-trihydroxy-tetrahydro-pyran-2-ylmethyl phosphoric acid ester (11% overall yield)

6-(2'-phenethyl)-3,4,5-trihydroxy-tetrahydro-pyran-2-ylmethyl phosphoric acid ester (19% overall yield) ESMS (−ve) 347 (M−H).

6-pentyl-3,4,5-trihydroxy-tetrahydro-pyran-2-ylmethyl phosphoric acid ester (40% overall yield) ESMS (−ve) 313 (M−H).

The monosodium salts of these esters were readily prepared by treating a concentrated ethanolic solution of the phosphate with 1.2 equivalents of anhydrous sodium acetate whereupon the desired salt precipitated, was washed with a small volume of ethanol and dried to give the following:

6-phenyl-3,4,5-trihydroxy-tetrahydro-pyran-2-ylmethyl phosphoric acid ester sodium salt (89%). $^1$Hnmr (500 MHz, D$_2$O): δ 3.42–3.50 (m, 1H), 3.58–3.61 (m, 1H), 3.77–3.80 (m, 1H) 3.89–3.94 (m, 1H), 3.97–4.01 (m, 1H), 4.43–4.44 (m, 1H), 4.91–4.92 (m, 1H), 7.23–7.30 (m, 5H); ESMS (−ve) 319 (M−H).

6-(4'-methoxyphenyl)-3,4,5-trihydroxy-tetrahydro-pyran-2-ylmethyl phosphoric acid ester sodium salt (67%). $^1$Hnmr (500 MHz, D$_2$O): δ 3.42–3.48 (m, 1H), 3.60–3.65 (m, 1H), 3.67 (s, CH$_3$), 3.77–3.80 (m, 1H), 3.85–3.88 (m, 1H), 3.97–4.05 (m, 1H), 4.38–4.42 (m, 1H), 4.85 (d, J=3.0 Hz, 1H), 6.84–6.90, (m, 2H), 7.22–7.27 (m, 2H); ESMS (−ve) 349 (M−H).

6-(2'-pyridyl)-3,4,5-trihydroxy-tetrahydro-pyran-2-ylmethyl phosphoric acid ester sodium salt (91%)

6-(2'-phenethyl)-3,4,5-trihydroxy-tetrahydro-pyran-2-ylmethyl phosphoric acid ester sodium salt (94%). $^1$Hnmr (500 MHz, D$_2$O): δ 1.58–1.67 (m, 1H), 1.77–1.85 (m, 1H), 2.45–2.60 (m, 2H) 3.16–3.26 (m, 2H), 3.34–3.38, (m, 1H), 3.52–3.55 (m, 1H), 3.64–3.77 (m, 1H), 3.90–3.94, (m, 1H), 4.02–4.06 (m, 1H), 7.07–7.20 (m, 5H); ESMS (−ve) 347 (M−H).

6-pentyl-3,4,5-trihydroxy-tetrahydro-pyran-2-ylmethyl phosphoric acid ester sodium salt (58%). $^1$Hnmr (500 MHz, D$_2$O): δ 0.71–0.73 (m, 3H), 1.10–1.25 (m, 6H), 1.26–1.50 (m, Example 7

Preparation of Phosphoric acid mono-[3-(3,4,5-trihydroxy-6-phosphonooxymethyl-tetrahydropyran-2-yl)-propyl] ester (Formula I; R=—(CH$_2$)$_3$—O—PO$_3$H$_2$)disodium salt Using a variation of the method described by by Guo et al. (Guo et al., 1997; incorporated herein by reference) to a stirred solution of methyl mannoside (52.4 g, 270 mmol) in DMF (1200 ml) was slowly added sodium hydride (58 g, ~6 eq.,). Stirring was continued and after ~1 hr tetrabutyl ammonium iodide (~0.1 eq., 10.6 g) was added followed by benzyl chloride (12 eq., 373 g, 410 ml). After stirring for 60 hours at room temperature, the reaction mixture was poured onto 25% concentrated ammonia solution in ethanol (1:3, 300 ml) and stirred for ~2 hours after which the solvent was removed under reduced pressure. The residue was extracted with diethyl ether (3×700 ml), the combined extracts were dried (sodium sulfate), filtered and evaporated under reduced pressure. The residue was taken up in light petroleum (800 ml), approximately 120 g of silica gel was added to this solution and this slurry was added to the top of a silica gel (250 g) column (90×200 mm) and eluted under vacuum as follows: 100% light petroleum (2400 ml, f1[800 ml], f2[1600 ml]), 10% ethyl acetate/light petroleum (1600 ml, f3[800 ml], f4[800 ml]), 25% ethyl acetate/light petroleum (800 ml, f5) and 100% ethyl acetate (800 ml, f6). Methyl 2,3,4,6-tetra-O-benzylmannoside was found in f3,4 (82.76 g). Impure material from f2/5 was re-chromatographed in a similar manner to give additional material (51.22 g) for a combined yield of 133.98 g, 90%. Using the method described by Wong et al., (Wong et al., 1997; incorporated herein by reference) to a solution of methyl-2,3,4,6-tetra-O-benzylmannoside (61.73 g, 111 mmol) in acetonitrile (250 ml) at 0° C. under nitrogen was added allyl trimethyl silane (2 eq., 26.4 g, 37.0 ml) followed by trimethylsilyl triflate (0.5 eq., 12.4 g, 10.1 ml). The reaction mixture was left overnight at 4° C. whereupon acetic anhydride (4 eq., 45.7 g, 42 ml) was added and after stirring for 2 hours the mixture was poured into saturated sodium bicarbonate/diethyl ether (1:1, 800 ml). The organic layer was removed and extracted with saturated sodium bicarbonate solution (400 ml). The combined aqueous layers were extracted again with diethyl ether (400 ml). The organic layers were combined washed with water (400 ml), dried (sodium sulfate), filtered and evaporated under reduced pressure. The residue was taken up in light petroleum (400 ml), to this was added approximately 80 g of silica gel and the slurry was poured onto the top of a column (90×200 mm) of silica gel (200 g). The column was then vacuum eluted with 100% light petroleum (800 ml, f1), 10% ethyl acetate/light petroleum (1600 ml, f2[800 ml], f3[800 ml]), 25% ethyl acetate/light petroleum (800 ml, f4), 100% ethyl acetate (800 ml, f5) and 10% methanol/dichloromethane (400 ml, f6). The product, acetic acid 6-allyl-3,4,5-tris-benzyloxy-tetrahydropyran-2-ylmethyl ester was found in f2,3,4 (52.10 g, 82%). To a stirred solution of this compound (83.36 g, 162 mmol) in methanol (500 ml) under a nitrogen atmosphere was added sodium methoxide (4.46 g). The reaction mixture was stirred for 3 hours, after which the solvent was removed. The residue was taken up in water:dichloromethane (300:500 ml) and acidified (1M HCl). The organic layer was removed and the aqueous layer further extracted with dichloromethane (300 ml). The combined organic layers were washed with water (300 ml), dried and the solvent removed to give (6-allyl-3,4,5-tris-benzyloxy-tetrahydro-pyran-2-yl)-methanol (73.8 g, 96%). This compound, (5.02 g, 10.5 mmol) was dissolved in dry tetrahydrofuran (50 ml) under nitrogen at 0° C. and a solution of borane in tetrahydrofuran (~1.0 M, ~4 eq, 42 ml) was added. The reaction mixture was allowed to warm to room temperature and followed by thin layer chromatography. Upon completion the reaction mixture was poured onto an aqueous sodium hydroxide solution (1 M, 50 ml) to which was added sodium percarbonate (2.99 g, ~4 eq). The reaction mixture was stirred overnight and extracted with diethyl ether (3×100 ml). The combined organic layers were washed with water (100 ml), dried (sodium sulfate), filtered and evaporated under reduced pressure. The residue was absorbed onto silica gel (40 g), added to the top of a column (70×140 mm) of silica gel (50 g). The column was then eluted under vacuum with 100% dichloromethane (800 ml, f1[400 ml], f2[400 ml]), 2% methanol/dichloromethane (800 ml, f3[400 ml], f4[400 ml]), 10% methanol/dichloromethane (800 ml, f5[400 ml], f6[400 ml]) and 100% methanol (400 ml, f7). The product 3-(3,4,5-tris-benzyloxy-6-hydroxymethyl-tetrahydropyran-2-yl)-propan-1-ol was found in f4 & 5 (4.21 g, 81%). This material (4.16 g, 8.46 mmol) was dissolved in dichloromethane (70 ml) and stirred under nitrogen and cooled to −10° C. Triethylamine (~20 eq, 17.1 g, 23.4 ml) was added followed by phosphorus oxychloride (~2.2 eq, 2.85 g, 1.70 ml). After stirring for 5 hours and allowing to warm to room temperature, water/acetone (1:1, 120 ml) was added and stirring was continued for a further 2 hours. The aqueous layer was separated, basified (pH~12) with sodium methoxide and extracted with dichloromethane (2×200 ml), then acidified with concentrated HCl (pH~2) and again extracted with dichloromethane (2×200 ml). The combined organic layers were dried (sodium sulfate), filtered and evaporated under reduced pressure to give pure phosphoric acid mono-[3-(3,4,5-tris-benzyloxy-6-phosphonooxymethyl-tetrahydro-pyran-2-yl)-propyl] ester (3.75 g, 68%). To a solution of this material (3.75 g, 5.75 mmol) in methanol (150 ml) and formic acid (1.5 ml) was added 10% palladium on charcoal (~100 mg). This solution was then placed under an atmosphere of hydrogen (55 psi) and shaken overnight. The reaction mixture was then filtered through celite, evaporated to dryness under reduced pressure and the residue dissolved in a minimum volume of water and added dropwise to a solution of sodium acetate (1.02 g, 2.2 eq) in ethanol (150 ml). The resulting precipitate was centrifuged and the ethanol decanted off, the residue was washed with diethyl ether (2×80 ml) and dried to give phosphoric acid mono-[3-(3,4,5-trihydroxy-6-phosphonooxymethyl-tetrahydro-pyran-2-yl)-propyl] ester disodium salt (1.24 g, 51%). $^1$Hnmr (500 MHz, D$_2$O): δ 1.10–1.20 (m, 2H), 1.44–1.82 (m, 2H), 3.02–3.12 (m, 1H) 3.17 (dd, J=13.0, 25.0 Hz, 2H), 3.52–3.64 (m, 1H), 3.70–3.90 (m, 2H), 3.91–4.00 (m, 1H), ESMS (−ve) 381 (M−H), 301 (M−PO$_3$H$_2$).

Example 8

Preparation of hexanoic acid 3-(3,4,5-trihydroxy-6-phosphonooxymethyl-tetrahydro-pyran-2-yl)-propyl ester monosodium salt and (Formula I; R=CH$_2$)$_3$—O—CO(CH$_2$)$_5$CH$_3$ 6-Allyl-3,4,5-tris-benzyloxy-tetrahydro-pyran-2-yl)-methanol (prepared as outlined in Example 7) (51.1 g, 108 mmol) was dissolved in dichloromethane (300 ml) and imidazole (~1.2 eq., 9.36 g) was added followed by tert-butyl-dimethylsilyl chloride (18.3 g, 121 mmol). The reaction mixture was stirred overnight and the solid was then filtered off. The filtrate was washed with water (2×250 ml), dried (sodium sulfate), filtered and evaporated under reduced pressure. The residue was taken up in 40–60 light petroleum (200 ml), this was added to ~50 g of silica gel and the slurry was added to the top of a silica gel column (90×200 mm; 150 g). The column was then vacuum eluted with 100% light petroleum (1200 ml, f1[400 ml], f2[800 ml]), 5% ethyl acetate/light petroleum (800 ml, f3), 10% ethyl acetate/light petroleum (800 ml, f4), and 100% ethyl acetate (400 ml, f5). The product (6-allyl-3,4,5-benzyloxy-tetrahydro-pyran-2-ylmethoxy)-tert-butyl-dimethyl-silane was found in f2,3,4 (52.10 g, 82%). This material (52.01 g, 88.5 mmol) was dissolved in dry tetrahydrofuran (500 ml) placed under nitrogen at 0° C., and to it was added a solution of borane in tetrahydrofuran (1.5M, ~1.2 eq, 92 ml). The reaction mixture was allowed to warm to room temperature and followed by thin layer chromatography. Upon completion the reaction mixture was poured onto an aqueous solution of sodium hydroxide (1M, 400 ml) to which was added sodium percarbonate (55.1 g, ~4 eq). The reaction mixture was stirred for 7 hours and extracted with diethyl ether (500 ml and 300 ml). The combined organic layers were washed with water (400 ml), dried (sodium sulfate), filtered and evaporated under reduced pressure. The residue was taken up in bp 40–60° light petroleum (200 ml) and added to ~50 g of silica gel, this slurry was then added to the top of a silica gel column (90×200 mm; 150 g). The column was then vacuum eluted with 100% light petroleum (1600 ml, f1), 5% ethyl acetate/light petroleum (800 ml, f2), 10% ethyl acetate/light petroleum (800 ml, f3), 25% ethyl acetate/light petroleum (800 ml, f4), 100% ethyl acetate (800 ml, f5) and 10% methanol/dichloromethane (800 ml, f6). The product 3-[3,4,5-tris-benzyloxy-6-(tert-butyl-dimethyl-silanyloxymethyl)-tetrahydro-pyran-2-yl]-propan-1-ol was isolated from f5 &6 (41.58 g, 78%). $^1$Hnmr (500 MHz, CDCl$_3$): δ 0.04 (s, 3H), 0.04 (s, 3H), 0.88 (s, 9H), 1.58–1.70 (m, 4H), 3.56 (dd, J=2.5, 5.5 Hz, 1H), 3.59–3.67 (m, 2H), 3.71 (dt, J=5.0, 5.5 Hz, 1H), 3.77–3.84 (m, 3H), 3.88 (dd, J=4.5, 10.0, 1H), 3.94–3.98 (m, 1H), 4.55–4.70 (m, 6H), 7.25–7.36 (m, 15H); ESMS (+ve) 607 (M+H), 629 (M+Na). This compound (9.3 g, 15.3 mmol) was dissolved in dichloromethane (50 ml) placed under nitrogen and was cooled to 0° C. To this was added triethylamine (1.5e q, 2.3 g, 3.2 ml), DMAP (catalytic amount) and hexanoyl chloride (1.1 eq, 2.28 g, 2.4 ml). The reaction mixture was allowed to warm to room temperature and monitored by thin layer chromatography. Upon completion the reaction mixture was poured onto water and extracted. The organic layer was then washed with saturated sodium bicarbonate (50 ml) and water (2×50 ml). The organic layer was then dried (sodium sulfate), filtered and evaporated under reduced pressure. The residue was taken up in 40–60 light petroleum (100 ml) and added to ~10 g of silica gel and the resulting slurry was added to the top of a column (70×140 mm) of silica gel (50 g). The column was then vacuum eluted with 100% light petroleum (400 ml, f1), 5% ethyl acetate/light petroleum (400 ml, f2), 10% ethyl acetate/light petroleum (400 ml, f3), 25% ethyl acetate/light petroleum (400 ml, f4), 100% ethyl acetate (400 ml, f5) and 10% methanol/dichloromethane (200 ml, f6). The product hexanoic acid 3-[3,4,5-tris-benzyloxy-6-(tert-butyl-dimethyl-silanyloxymethyl)-tetrahydro-pyran-2-yl]-propyl ester was found in f2 & 3 (9.79 g, 91%). This material (9.79 g, 13.9 mmol) was dissolved in tetrahydrofuran (150 ml), placed under nitrogen at room temperature and tetrabutylammonium fluoride (2.1 eq, 7.75 g) was added. The reaction was monitored by thin layer chromatography and after 2 hours the solvent was removed. The residue was dissolved in diethyl ether (200 ml) extracted with water (2×100 ml), dried (sodium sulfate), filtered and evaporated under reduced pressure. The residue was taken up in 40–60 light petroleum (100 ml) and added to ~15 g of silica gel and the resulting slurry was added to the top of a column (70×140 mm) of silica gel (50 g). The column was then vacuum eluted with 100% light petroleum (400 ml, f1), 10% ethyl acetate/light petroleum (400 ml, f2), 25% ethyl acetate/light petroleum (400 ml, f3), 50% ethyl acetate/light petroleum (400 ml, f4), 100% ethyl acetate (400 ml, f5) and 10% methanol/dichloromethane (200 ml, f6). The product hexanoic acid 3-(3,4,5-tris-benzyloxy-6-hydroxymethyl-tetrahydro-pyran-2-yl)-propyl ester was found in f3 & 4 (7.70 g, 94%). This material (7.70 g, 13.1 mmol) was dissolved in dichloromethane (50 ml) placed under nitrogen and cooled to 0° C., whereupon triethylamine (~2.2 eq, 2.66 g, 3.70 ml) was added followed by phosphorus oxychloride (1.3 eq, 2.60 g, 1.55 ml). The reaction mixture was allowed to warm to room temperature while stirring overnight after which the solid was filtered off. The filtered material was washed with dichloromethane (5×10 ml) and the filtrate and washings were combined and taken to dryness and the residue was dissolved in water:acetone (1:1, 100 ml) and stirred for 3 hours at 45° C. The majority of the acetone was removed from the mixture under reduced pressure and dichloromethane (150 ml) added. The aqueous layer was further extracted with dichloromethane (150 ml) and the organic extracts combined and washed with water (100 ml), dried (sodium sulfate), filtered and evaporated under reduced pressure to give the required product hexanoic acid 3-(3,4,5-tris-benzyloxy-6-phosphonooxymethyl-tetrahydro-pyran-2-yl)-propyl ester (8.61 g, 98%). To a solution of this material (3.75 mmol) in methanol (135 ml), water (15 ml) and formic acid (1.5 ml) was added 10% palladium on charcoal (~1.3 mg). This solution was then placed under an atmosphere of hydrogen (55 psi) and shaken overnight. The reaction mixture was then filtered through celite, the solvent removed, the residue dissolved in a minimum of water and added dropwise to a solution of sodium acetate (1.2 eq, 1.27 g) in ethanol 150 ml). The resulting precipitate was centrifuged and the ethanol decanted off, the residue was washed with diethyl ether (2×100 ml) and dried to give hexanoic acid 3-(3,4,5-trihydroxy-6-phosphonooxymethyl-tetrahydro-pyran-2-yl)-propyl ester monosodium salt (4.76 g, 87%). $^1$Hnmr (500 MHz, $D_2O$): δ 0.66–0.78 (m, 2H), 0.98–1.08 (m, 2H), 1.08–1.22 (m, 3H), 1.36–1.61 (m, 2H) 2.18–2.30 (m, 1H), 3.40–3.55 (m, 3H), 3.57–3.95 (m, 5H), 3.95–4.06 (m, 1H); ESMS (−ve) 399 (M−H), 301 (M−$C_6H_{10}O$).

Example 9

Preparation of phosphoric acid mono-[3,4,5-trihydroxy-6-(3-hydroxy-propyl)-tetrahydro-pyran-2-ylmethyl] ester monosodium salt Hexanoic acid 3-(3,4,5-trihydroxy-6-phosphonooxymethyl-tetrahydro-pyran-2-yl)-propyl ester (2.1 g, 5.25 mmol) (prepared in Example 8) was dissolved in water (50 ml) and aqueous sodium hydroxide (1M, 4 eq, 12 ml) was added and stirred for 40 minutes at room temperature after which the solution was acidified (pH~2) with Dowex 50W X8 $H^+$ form. The solution was washed with dichloromethane (2×100 ml) and the solvent was removed. The residue was then dissolved in a minimum of water and added dropwise to a solution of sodium acetate (1.2 eq, 0.34 g) in ethanol (150 ml) and diethyl ether (50 ml). The resulting precipitate was centrifuged and the ethanol decanted off, the residue was washed with diethyl ether (2×100 ml) and dried to give phosphoric acid mono-[3,4,5-trihydroxy-6-(3-hydroxy-propyl)-tetrahydro-pyran-2-ylmethyl] ester monosodium salt (1.01 g, 63%). $^1$Hnmr (500 MHz, $D_2O$): δ 1.35–1.46 (m, 2H), 1.46–1.58 (m, 1H), 1.62–1.72 (m, 1H), 3.41–3.50 (m, 3H) 3.56 (t, J=9.0 Hz, 1H), 3.65–3.70 (m, 1H), 3.71–3.79 (m, 2H), 3.83–3.96 (m, 2H); ESMS (−ve) 301 (M−H).

Example 10

Preparation of 3-phenyl-2-[2-(3,4,5-trihydroxy-6-phosphonooxymethyl-tetrahydro-pyran-2-yl)-acetylamino]-propionic acid monosodium salt.
(Formula I; R=—$CH_2$—CO—NH—CH($CO_2H$) $CH_2Ph$)

In a similar method to that described by Khan et al., (Khan, et al., 1996; incorporated herein by reference), to a stirred solution of penta-O-acetyl mannose (30.13 g, 77.3 mmol) in acetonitrile (300 ml) at 4° C. was added hydrazine monohydrate (1.2 eq, 4.65 g, 4.51 ml). The reaction mixture was maintained at 4° C. in a refrigerator for ~16 hours whereupon it was filtered through a column (40×90 mm) of celite (25 g) atop flash silica gel (20 g) which was then washed with dichloromethane (300 ml). The filtrates were combined and the solvent removed under reduced pressure and the residue adsorbed onto flash silica (~30 g). This was placed on a column (70×140) of flash silica (50 g) and eluted with 10% ethyl acetate/light petroleum (400 ml, f1), 50% ethyl acetate/light petroleum (2×600 ml f2 & 3), 100% ethyl acetate (400 ml, f4) and 25% methanol/dichloromethane (400 ml, f5). Most the required product, acetic acid 3,5-diacetoxy-2-acetoxymethyl-6-hydroxy-tetrahydro-pyran-4-yl ester (26.89 g, 77.1 mmol was found in f2. This compound (26.83 g, 77.1 mmol), in accordance with the method described by Mata et al. (Mata et al., 1992; incorporated herein by reference), was stirred with Meldrum's Acid (2.1 eq, 23.9 g) and triethylamine (2 eq, 15.6 g, 22.0 ml) in acetonitrile (200 ml) at 40–50° C. for ~60 hours. The solvent was then removed, acetic acid/water (9:1, 300 ml) was added to the residue and then heated at 100° C. for ~3 hr. After the solvent was removed the residue was dissolved in dichloromethane (300 ml) and washed with water (2×300 ml) and extracted with saturated sodium bicarbonate solution (2×200 ml). The combined bicarbonate layer was carefully acidified with HCl (5M, ~pH=3), upon standing a solid formed and was filtered off to give the required compound (3,4,5-triacetoxy-6-acetoxymethyl-tetrahydropyran-2-yl)-acetic acid (10.73, 36%). $^1$Hnmr (500 MHz, $CDCl_3$): δ 1.99 (s, 3H), 2.05 (s, 3H), 2.09 (s, 3H), 2.20 (s, 3H), 2.51 (dd, J=5.0, 16.0 Hz, 1H), 2.69 (dd, J=8.0, 16.5 Hz, 1H), 3.70 (ddd, J=2.0, 5.5, 9.5 Hz, 1H), 4.11, (dd, J=2.5, 12.5 Hz, 1H), 4.13 (dd, J=5.5, 7.5 Hz, 1H), 4.26 (dd, J=5.5, 12.0 Hz, 1H), 5.11 (dd, J=3.5, 10.0 Hz, 1H), 5.23 (t, J=10.0 Hz, 1H), 5.40 (d, J=3.5 Hz, 1H); ESMS (+ve) 413 (M+Na). This compound (5.15 g, 13.3 mmol) was dissolved in dichloromethane (200 ml) to this was added phenylalanine methyl ester hydrochloride (1.1 eq, 3.15 g), triethylamine (2.3 eq, 3.2 g, 4.3 ml), hydroxy succinimide (1.1 eq, 1.69 g) and dicyclohexylcarbodiimide (1.6 eq, 4.72 g). The reaction was stirred overnight, filtered and then extracted with water (2×200 ml), hydrochloric acid (1M, 2×200 ml), and water (2×200 ml). The organic layer was dried (sodium sulfate), filtered and evaporated under reduced pressure. The residue was adsorbed on ~10 g silica gel, placed on a column (70 140 mm) of silica gel (50 g) and eluted with 25% light petroleum/dichloromethane (400 ml, f1), 50% light petroleum/dichloromethane (800 ml, f2[400 ml] & f3[400 ml]), 100% dichloromethane (800 ml, f4[400 ml, f5[400 ml]), 5% methanol/dichloromethane (400 ml, f6), 10% methanol/dichloromethane (400 ml, f7) and 100% methanol (400 ml, f8). The product was found in f6 and was dissolved in diethyl ether (2×200 ml), the insoluble reaction by-product was filtered off and the solvent was removed to give 3-phenyl-2-[2-(3,4,5-triacetoxy-6-acetoxymethyl-tetrahydro-pyran-2-yl)-acetylamino]-propionic acid methyl ester (7.09 g, 97%). This compound (7.87 g, 14.3 mmol) was dissolved in dry methanol (50 ml) and sodium methoxide (550 mg) was added. The reaction was followed by thin layer chromatography and after 1 hour Dowex 50W X8 $H^+$ form ion exchange resin was added and after a further 30 min the reaction mixture was filtered and the solvent removed to give 3-phenyl-2-[2-(3,4,5-trihydroxy-6-hydroxymethyl-tetrahydro-pyran-2-yl)-acetylamino]-propionic acid methyl ester (4.80 g, 88%). To this material (4.80 mg, 12.5 mmol) in pyridine (50 ml) was added trityl chloride (2.5 eq, 8.63 g) and the mixture stirred at 50° C. overnight. After cooling to room temperature acetic anhydride (8 eq, 10.5 g) was added and the mixture stirred 3 hours, whereupon it was added to ice cold water (200 ml) and extracted with dichloromethane (3×200 ml). The organic phase was dried (sodium sulfate), filtered and evaporated under reduced pressure to give impure 3-phenyl-2-[2-(3,4,5-triacetoxy-6-trityloxymethyl-tetrahydro-pyran-2-yl)-acetylamino]-propionic acid. The entire amount of this material was stirred at room temperature with anhydrous ferric chloride (8.89 g) in dichloromethane (100 ml) for 1.5 hours, whereupon water (100 ml) was added and the mixture extracted with chloroform (3×200 ml). The organic extracts were combined and dried (sodium sulfate), filtered and the filtrate evaporated under reduced pressure. The residue was vacuum chromatographed on a silica gel (0.063–0.2 mm) column (2×30 cm), eluted with 10% ethyl acetate/light petroleum (300 ml, f1), 100% dichloromethane (350 ml, f2), 10% methanol/dichloromethane (350 ml, f3) and 100% methanol (150 ml, f4) to give 3-phenyl-2-[2-(3,4,5-triacetoxy-6-hydroxymethyl-tetrahydro-pyran-2-yl)-acetylamino]-propionic acid methyl ester (5.24 g, 82%). This compound (5.02 g, 9.86 mmol) was dissolved in dichloromethane (75 ml) and pyridine (0.86 g) and the mixture cooled to 0° whereupon phosphorus oxychloride (2.2 eq, 3.2 g) was added dropwise with stirring under a dry nitrogen atmosphere. The mixture was allowed to warm to room temperature and stirred overnight. The mixture was filtered and evaporated to dryness under reduced pressure. The residue was dissolved in a 1:1 mixture of acetone and water (80 ml) and kept at 45–50° for 2 hours. After evaporation to dryness the residue was evaporated from 50 ml of ethanol. This material was stirred at room temperature overnight in methanol (100 ml) that contained sodium methoxide (4 eq, 2.18 g) and water (2 ml), after which it was treated with a strong cationic exchange resin (Dowex 50W H$^+$ form) to remove sodium ions. The ion exchange resin was filtered off and the filtrate taken to dryness under reduced pressure and the residue evaporated from ethanol (50 ml) to give methyl 3-phenyl-2-[2-(3,4,5-trihydroxy-6-phosphonooxymethyl-tetrahydro-pyran-2-yl)-acetylamino]-propionic acid. This material was then dissolved in a minimum of water and added dropwise to a solution of sodium acetate (7.4 g) in ethanol (500 ml). The resulting precipitate was pelleted by centrifugation and the ethanol decanted off, the solid was washed with diethyl ether (2×100 ml) and dried to give 3-phenyl-2-[2-(3,4,5-trihydroxy-6-phosphonooxymethyl-tetrahydro-pyran-2-yl)-acetylamino]-propionic acid monosodium salt (2.19 g, 47%). $^1$Hnmr (500 MHz, D$_2$O): δ 2.44–2.66 (m, 2H), 2.86 (dd, J=4.0, 18.0 Hz, 2H), 3.06–3.15 (m, 1H), 3.40–3.46 (m, 1H) 3.48–3.55 (m, 1H), 3.80–3.92 (m, 3H), 3.94–4.02 (m, 1H), 4.47 (dd, J=1.5, 4.0 Hz, 1H), 7.11–7.31 (m, 5H); ESMS (–ve) 448 (M–H).

Example 11

Preparation of phosphoric acid mono-[6-(3-hexyloxy-propyl)-3,4,5-trihydroxy-tetrahydro-pyran-2-ylmethyl] ester (Formula I; R=—(CH$_2$)$_3$—O—(CH$_2$)$_5$CH$_3$ sodium salt To a suspension of 60% sodium hydride (320 mg, 8 mmol) in DMF (10 ml) at 0° C. under an atmosphere of nitrogen was added 3-[3,4,5-tris-benzyloxy-6-(tert-butyl-dimethyl-silanyloxymethyl)-tetrahydro-pyran-2-yl]-propan-1-ol (Example 8) (4 g, 6.6 mmol). After 10 min iodohexane (1.2 ml, 8 mmol) was added and the resultant solution stirred for 2 hours. The solvent was removed under reduced pressure and ethyl acetate (100 ml) added to the oily residue which was subsequently washed with 1M hydrochloric acid (2×100 ml), saturated sodium bicarbonate (2×100 ml) and brine (100 ml), dried over anhydrous sodium sulfate, and evaporated to dryness. The residue was purified on a rapid vacuum silica gel (0.040–0.063 mm) column eluted with light petroleum (200 ml), 5% ethyl acetate in light petroleum (200 ml), 10% ethyl acetate in light petroleum (200 ml), 25% ethyl acetate in light petroleum (4×200 ml) and 50% ethyl acetate in light petroleum (200 ml) to give tert-butyl-dimethyl-[3,4,5-tris-benzyloxy-6-(3-hexyloxy-propyl)-tetrahydro-pyran-2-ylmethoxy]-silane (silica tlc, Rf 0.68 in 25% EtOAc/Light Petroleum, ESMS (+ve) 713 (M+Na)) as an oil (3.5 g, 77% yield). This material (3.1 g, 4.5 mmol) was dissolved in THF (20 ml) and tetrabutyl ammonium fluoride (2.3 g, 9 mmol) added. The resulting solution was stirred overnight, the solvent removed under reduced pressure and ethyl acetate (100 ml) added to the oily residue which was subsequently washed with 1M hydrochloric acid (2×100 ml) and brine (100 ml), dried over anhydrous sodium sulfate, and evaporated to dryness. The residue was purified on a rapid vacuum silica gel (0.040–0.063 mm) column eluted with light petroleum (200 ml), 5% ethyl acetate in light petroleum (200 ml), 10% ethyl acetate in light petroleum (200 ml), 25% ethyl acetate in light petroleum (200 ml), 50% ethyl acetate in light petroleum (2×200 ml) and 100% ethyl acetate (200 ml) to give [3,4,5-tris-benzyloxy-6-(3-hexyloxy-propyl)-tetrahydro-pyran-2-yl]-methanol (tlc silica gel, Rf 0.31 in 25% EtOAc/Light Petroleum, ESMS (+ve) 577 (M+H), 599 (M+Na)) as an oil (2.2 g, 85%). This material (2.1 g, 3.65 mmol) was dissolved in dry dichloromethane (10 ml) and triethylamine (1 ml, 7.29 mmol) and the mixture cooled to 0° C. whereupon phosphorous oxychloride (0.424 ml, 4.56 mmol) was added dropwise with stirring under an atmosphere of nitrogen. The mixture was allowed to warm to room temperature and stirred for 2 hours. The solvent was evaporated and the residue diluted with ether and centrifuged to remove insoluble salts. The supernatant was then evaporated and redissolved in a 1:1 mixture of acetone and water (20 ml) and kept at 45–50° C. for 2 hours. The solvent was removed under reduced pressure to give phosphoric acid mono-[3,4,5-tris-benzyloxy-6-(3-hexyloxy-propyl)-tetrahydro-pyran-2-ylmethyl] ester, ESMS (+ve) 679 (M+Na), (–ve) 655 (M–H), 691 (M+Cl). This compound was dissolved with 1% formic acid in methanol (100 ml), 10% palladium on carbon (100 mg) added and hydrogenated at 40 psi overnight. The mixture was filtered through celite and the filtrate evaporated to dryness to give phosphoric acid mono-[6-(3-hexyloxy-propyl)-3,4,5-trihydroxy-tetrahydro-pyran-2-ylmethyl] ester, ESMS (+ve) 387 (M+H), 409 (M+Na), (–ve) 385 (M–H)). From this was prepared the mono sodium salt by dissolving this compound in a 1:1 solution of water and ethanol (2 ml) and dropwise addition of this solution to sodium acetate (263 mg, 3.2 mmol) dissolved in ethanol (50 ml). The resulting precipitate was isolated by centrifugation to give phosphoric acid mono-[6-(3-hexyloxy-propyl)-3,4,5-trihydroxy-tetrahydro-pyran-2-ylmethyl] ester, monosodium salt as a white solid (997 mg, 71%). $^1$Hnmr (500 MHz, D$_2$O): δ 0.72 (t, J=6.5 Hz, 3H), 1.11–1.20 (m, 6H), 1.38–1.48 (m, 4H), 1.57 (m, 1H), 1.69 (m, 1H), 3.35–3.42 (m, 4H), 3.49 (m, 1H), 3.59 (t, J=9.5 Hz, 1H), 3.68 (dd, J=3.5, 9.5 Hz, 1H), 3.74 (m, 1H), 3.78 (dd, J=4.0, 10.5 Hz, 1H), 3.89–3.93 (m, 2H).

Example 12

Preparation of phosphoric acid mono-[6-(3-butyrylamino-propyl)-3,4,5-trihydroxy-tetrahydro-pyran-2-ylmethyl] ester (Formula I; R=—(CH$_2$)$_3$—NH—CO(CH$_2$)$_2$CH$_3$ monosodium salt 3-[3,4,5-Tris-benzyloxy-6-(tert-butyl-dimethyl-silanyloxymethyl)-tetrahydro-pyran-2-yl]-propan-1-ol (from Example 8) (2.2 g, 3.6 mmol) and triethylamine (0.56 ml, 4 mmol) were dissolved in dry dichloromethane (10 ml) and cooled to 0° C. under an atmosphere of nitrogen. To this solution was added methanesulfonylchloride (0.29 ml, 3.8 mmol) and the resultant mixture stirred for 2 hours before diluting with ether (40 ml). The precipitate was removed by centrifugation and the supernatant evaporated under reduced pressure. The crude mesylate was dissolved in dimethylformamide (10 ml), sodium azide (1.17 g, 18 mmol) added and the mixture heated at 70° C. overnight. The mixture was cooled, diluted with ethyl acetate (100 ml) and washed with 1M hydrochloric acid (2×100 ml), saturated sodium bicarbonate (2×100 ml) and brine (100 ml), dried over anhydrous sodium sulfate, and evaporated to dryness. The residue was purified on a rapid vacuum silica gel (0.040–0.063 mm) column eluted with light petroleum (200 ml), 5% ethyl acetate in light petroleum (200 ml), 10% ethyl acetate in light petroleum (200 ml), 25% ethyl acetate in light petroleum (200 ml), 50% ethyl acetate in light petroleum (2×200 ml) and 100% ethyl acetate (200 ml) to give 3-[3,4,5-tris-benzyloxy-6-(tert-butyl-dimethyl-silanyloxymethyl)-tetrahydro-pyran-2-yl]-propylazide (tlc silica gel, Rf 0.80 in 25% EtOAc/Light petroleum) as an oil (2.05 g, 90%). This compound (3.4 g, 5.4 mmol) dissolved in dry ether (10 ml) was added to a suspension of lithium aluminium hydride (614 mg, 16.1 mmol) in ether (50 ml) at 0° C. under an atmosphere of nitrogen. The resulting solution was allowed to warm to room temperature and stirred for 2 hours. During this reaction the silyl protecting group was also removed. The reaction was quenched with 2M sodium hydroxide (5 ml), diluted with water (50 ml) and extracted with ether (4×50 ml). The combined ethereal extracts were washed with brine, dried over sodium sulfate and evaporated to give crude [6-(3-amino-propyl)-3,4,5-tris-benzyloxy-tetrahydro-pyran-2-yl]-methanol, ESMS (+ve) 606 (M+H). This crude compound was reacted with butyric acid (486 mg, 5.4 mmol) activated with BOP reagent (2.4 g, 5.4 mmol) and diisopropylethylamine (1.7 ml, 10 mmol) in tetrahydrofuran (20 ml). After 2 hours the solvent was removed under reduced pressure and ethyl acetate (100 ml) added to the oily residue which was subsequently washed with 1M hydrochloric acid (2×100 ml), saturated sodium bicarbonate (2×100 ml) and brine (100 ml), dried over anhydrous sodium sulfate, and evaporated to dryness. The residue was purified on a rapid vacuum silica gel (0.040–0.063 mm) column eluted with light petroleum (200 ml), 5% ethyl acetate in light petroleum (200 ml), 10% ethyl acetate in light petroleum (200 ml), 25% ethyl acetate in light petroleum (200 ml), 50% ethyl acetate in light petroleum (200 ml) and 100% ethyl acetate (3×100 ml) to give N-[3-(3,4,5-tris-benzyloxy-6-hydroxymethyl-tetrahydro-pyran-2-yl)-propyl]-butyramide (tlc silica gel, Rf 0.38 in 100% EtOAc, ESMS (+) 562 (M+H), 584 (M+Na)) as an oil (1.9 g, 62%). This compound (1.85 g, 3.3 mmol) was dissolved in dry dichloromethane (10 ml) and triethylamine (585 μl, 4.2 mmol) and the mixture cooled to 0° C. whereupon phosphorous oxychloride (585 μl, 3.9 mmol) was added dropwise with stirring under an atmosphere of nitrogen. The mixture was allowed to warm to room temperature and stirred for 2 hours. The solvent was evaporated and the residue diluted with ether and centrifuged to remove insoluble salts. The supernatant was then evaporated and redissolved in a 1:1 mixture of acetone and water (20 ml) and kept at 45–50° C. for 2 hours. The solvent was removed under reduced pressure to give phosphoric acid mono-[3,4,5-tris-benzyloxy-6-(3-butyrylamino-propyl)-tetrahydro-pyran-2-ylmethyl] ester, ESMS (+ve) 642 (M+H), (–ve) 640 (M–H). This compound was dissolved with 1% formic acid in methanol (100 ml), 10% palladium on carbon (100 mg) added and hydrogenated at 40 psi overnight. The mixture was filtered through celite and the filtrate evaporated to dryness to give phosphoric acid mono-[6-(3-butyrylamino-propyl)-3,4,5-trihydroxy-tetrahydro-pyran-2-ylmethyl] ester, ESMS (–ve) 370 (M–H). From this was prepared the mono sodium salt by dissolving this compound in a 1:1 solution of water and ethanol (2 ml) and dropwise addition of this solution to sodium acetate (270 mg, 3.3 mmol) dissolved in ethanol (50 ml). The resulting precipitate was isolated by centrifugation to give phosphoric acid mono-[6-(3-hexyloxy-propyl)-3,4, 5-trihydroxy-tetrahydro-pyran-2-ylmethyl] ester, monosodium salt as a white solid (850 mg, 69%). $^1$Hnmr (500 MHz, D$_2$O): δ 0.74 (t, J=7.5 Hz, 3H), 1.32–1.54 (m, 4H), 1.66 (m, 2H), 2.06 (t, J=7.5 Hz, 2H), 3.08 (t, J=5.8 Hz, 2H), 3.32–3.92 (m, 7H).

Example 13

Preparation of 2-[2-(3,4,5-trihydroxy-6-phosphonooxymethyl-tetrahydro-pyran-2-yl)-acetylamino]-pentanedioic acid (Formula I; R= CH$_2$—CO—NH—CH(CO$_2$H)CH$_2$CH$_2$CO$_2$H)

Acetic acid 6-allyl-3,4,5-tris-benzyloxy-tetrahydro-pyran-2-ylmethyl ester (from Example 7) (5 g, 9.7 mmol) was dissolved in dichloromethane (50 ml), water (50 ml), acetic acid (5 ml) and aliquat336 (1 ml) and cooled to 0° C. To this solution was added potassium permanganate (6.1 g, 38.7 mmol) portionwise with vigorous stirring, the resultant mixture allowed to warm to room temperature and stirring continued overnight. The reaction mixture was cooled to 0° C. and quenched with sodium sulfite (10 g), 5M hydrochloric acid (50 ml) was added and the mixture extracted with dichloromethane (4×50 ml). The combined organic extracts were washed with brine (100 ml), dried over sodium sulfate and evaporated. The residue was purified on a rapid vacuum silica gel (0.040–0.063 mm; 100 g) column (70×200 mm) eluted with dichloromethane (200 ml), 2.5% methanol dichloromethane (2×200 ml), 5% methanol in dichloromethane (2×200 ml), 10% methanol in dichloromethane (2×200 ml), 20% methanol in dichloromethane (2×200 ml) to give (6-acetoxymethyl-3,4,5-tris-benzyloxy-tetrahydro-pyran-2-yl)-acetic acid (tlc silica gel, Rf 0.6 in 10% MeOH/DCM, ESMS (–ve) 533 (M–H), 569 (M+Cl). This compound was reacted with sodium methoxide (1.3 g, 24 mmol) in methanol (10 ml) to give (3,4,5-tris-benzyloxy-6-hydroxymethyl-tetrahydro-pyran-2-yl)-acetic acid (tlc silica gel, Rf 0.5 in 10% MeOH/DCM, ESMS (–ve) 491 (M–H), 527 (M+Cl)) as an oil (3.1 g, 65%). This compound (3 g, 6 mmol), BOP reagent (2.87 g, 6.5 mmol) and the tosyl salt of glutamic acid, dibenzyl ester (4 g, 8 mmol) were combined in tetrahydrofuran (20 ml) and diisopropylethylamine (3.5 ml, 20 mmol) added. After 4 hours the solvent was removed under reduced pressure and ethyl acetate (100 ml) added to the oily residue this mixture was subsequently washed with 1M hydrochloric acid (2×100 ml), saturated sodium bicarbonate (2×100 ml) and brine (100 ml), dried over anhydrous sodium sulfate, and evaporated to dryness. The residue was purified on a rapid vacuum silica gel (0.040–0.063 mm; 100 g) column (70×200 mm) eluted with light petroleum (200 ml), 10% ethyl acetate in light petroleum (200 ml), 20% ethyl acetate in light petroleum (200 ml), 30% ethyl acetate in light petroleum (200 ml), 40% ethyl acetate in light petroleum (200 ml), 50% ethyl acetate in light petroleum (4×200 ml) and 100% ethyl acetate (2×100 ml) to give 2-[2-(3,4,5-tris-benzyloxy-6-hydroxymethyl-tetrahydro-pyran-2-yl)-acetylamino]-pentanedioic acid dibenzyl ester (tlc silica gel, Rf 0.34 in 50% EtOAc/Light petroleum, ESMS (+ve) 802 (M+H), 824 (M+Na)) as an oil (1.4 g, 29%). This compound (2.4 g, 3.0 mmol) was dissolved in dry dichloromethane (10 ml) and triethylamine (557 μl, 4 mmol) and the mixture cooled to 0° C. whereupon phosphorous oxychloride (307 µl, 3.3 mmol) was added dropwise with stirring under an atmosphere of nitrogen. The mixture was allowed to warm to room temperature and stirred for 2 hours. The solvent was evaporated and the residue diluted with ether and centrifuged to remove insoluble salts. The supernatant was then evaporated and redissolved in a 1:1 mixture of acetone and water (20 ml) and kept at 45–50° C. for 2 hours. The solvent was removed under reduced pressure to give 2-[2-(3,4,5-tris-benzyloxy-6-phosphonooxymethyl-tetrahydro-pyran-2-yl)-acetylamino]-pentanedioic acid dibenzyl ester, ESMS (+ve) 882 (M+H). This compound was dissolved with 1% formic acid in 1:1 methanol and water (100 ml), 10% paladium on carbon (100 mg) added and hydrogenated at 40 psi overnight. The mixture was filtered through celite and the filtrate evaporated to dryness to give 2-[2-(3,4,5-trihydroxy-6-phosphonooxymethyl-tetrahydro-pyran-2-yl)-acetylamino]-pentanedioic acid, ESMS (–ve) 430 (M–H). From this was prepared the di sodium salt by dissolving this compound in a 1:1 solution of water and ethanol (2 ml) and dropwise addition of this solution to sodium acetate (541 mg, 6.6 mmol) dissolved in ethanol (50 ml). The resulting precipitate was isolated by centrifugation to give 2-[2-(3,4,5-trihydroxy-6-phosphonooxymethyl-tetrahydro-pyran-2-yl)-acetylamino]-pentanedioic acid, disodium salt as a white solid (732 mg, 51%). $^1$Hnmr (500 MHz, D$_2$O): δ 1.75 (m, 1H), 1.94 (m, 1H), 2.13 (t, J=8.0 Hz, 2H), 2.52 (dd, J=6.5, 15.0 Hz, 1H), 2.64 (dd, J=8.5, 15.0 Hz, 1H), 3.54 (m, 1H), 3.64–3.73 (m, 2H), 3.76 (m, 1H), 3.85–3.97 (m, 2H), 4.03 (m, 1H), 4.21 (m, 1H).

In a Similar Manner was made the Following:

Phosphoric acid mono-[3,4,5-trihydroxy-6-(phenethylcarbamoyl-methyl)-tetrahydro-pyran-2-ylmethyl] ester (Formula I; R=—CH$_2$—CO—NH—CH$_2$CH$_2$Ph) in an overall yield from (3,4,5-tris-benzyloxy-6-hydroxymethyl-tetrahydro-pyran-2-yl)-acetic acid (2 g, 4.06 mmol) of 300 mg (18%). ESMS (–ve) 404 (M–H). $^1$Hnmr (500 MHz, D$_2$O): δ 2.28 (dd, J=5.5, 14.5 Hz, 1H), 2.53 (dd, J=10.0, 14.5 Hz, 1H), 2.68 (t, J=7.0 Hz), 3.33 (m, 2H), 3.42 (m, 1H), 3.58–3.67 (m, 3H), 3.77 (m, 1H), 3.86 (m, 1H), 4.11 (m, 1H), 7.13–7.16 (m, 3H), 7.21–7.25 (m, 2H).

Example 14

Preparation of phosphoric acid mono-[3,4,5-trihydroxy-6-(3-{3-[3-(3,4,5-trihydroxy-6-phosphonooxymethyl-tetrahydro-pyran-2-yl)-propoxy]-phenoxy}-propyl)-tetrahydro-pyran-2-ylmethyl] ester (Formula I; R=—(CH$_2$)$_3$—O—C$_6$H$_4$—O—(CH$_2$)$_3$-Z, where Z is pyran moiety of Formula I)

3-[3,4,5-Tris-benzyloxy-6-(tert-butyl-dimethyl-silanyloxymethyl)-tetrahydro-pyran-2-yl]-propan-1-ol (prepared in Example 8) (5 g, 8.25 mmol) and carbon tetrabromide (3.4 g, 10.3 mmol) were dissolved in dry dichloromethane and cooled to 0° C. under an atmosphere of nitrogen. To this solution was added triphenylphoshine (3.25 g 12.3 mmol) in approximately equal portions over 10 min. The reaction mixture was warmed to room temperature and stirring continued for 1 hour before removing the solvent under reduced pressure. The crude residue was diluted with ether (50 ml) which was subsequently decanted to leave precipitated triphenylphosphine oxide. This was repeated twice and the combined ethereal washings combined, evaporated and the residue purified on a rapid vacuum silica gel (0.040–0.063 mm; 100 g) column (70×200 mm) eluted with light petroleum (200 ml), 2.5% ethyl acetate in light petroleum (200 ml), 5% ethyl acetate in light petroleum (2×200 ml), 10% ethyl acetate in light petroleum (3×200 ml) and 20% ethyl acetate in light petroleum (200 ml) to give tert-butyl-dimethyl-[3,4,5-tris-benzyloxy-6-(3-bromo-propyl)-tetrahydropyran-2-ylmethoxy]-silane (tlc silica gel, Rf 0.42 in 10% EtOAc/Light petroleum) as an oil (4.3 g, 78%). This compound (1 g, 1.49 mmol) was combined with resorcinol (78 mg, 0.71 mmol) and potassium carbonate (823 mg, 6 mmol) in dimethylformamide (5 ml) and heated to 70° C. for 36 h. The reaction mixture was diluted with ethyl acetate (100 ml) and washed with 1M hydrochloric acid (3×100 ml) and brine (100 ml), dried over anhydrous sodium sulfate, filtered and evaporated. The residue was purified on a rapid vacuum silica gel (0.040–0.063 m; 100 g) column (70×200 mm) eluted with light petroleum (200 ml), 5% ethyl acetate in light petroleum (200 ml), 10% ethyl acetate in light petroleum (2×200ml), 25% ethyl acetate in light petroleum (2×200 ml), 50% ethyl acetate in light petroleum (200 ml) and 100% ethyl acetate in light petroleum (200 ml) to give the desired di-addition product (tlc silica gel, Rf 0.78 in 25% EtOAc/Light Petroleum, ESMS (+ve) 1309 (M+Na)) as an oil (830 mg, 91%). This compound was dissolved in tetrahydrofuran (5 ml) and tetrabutyl ammoniumfluoride (666 mg, 2.55 mmol) added. The resulting mixture was stirred overnight at room temperature, the solvent removed under reduced pressure and ethyl acetate (100 ml) added to the oily residue which was subsequently washed with 1M hydrochloric acid (2×100 ml), saturated sodium bicarbonate (2×100 ml) and brine (100 ml), dried over anhydrous sodium sulfate, filtered and evaporated to dryness. The residue was purified on a rapid vacuum silica gel (0.040–0.063 mm; 100 g) column (70×200 mm) eluted with light petroleum (200 ml), 10% ethyl acetate in light petroleum (200 ml), 20% ethyl acetate in light petroleum (200 ml), 30% ethyl acetate in light petroleum (200 ml), 40% ethyl acetate in light petroleum (200 ml), 50% ethyl acetate in light petroleum (4×200 ml) and 100% ethyl acetate (2×100 ml) to give [3,4,5-tris-benzyloxy-6-(3-{3-[3-(3,4,5-tris-benzyloxy-6-hydroxymethyl-tetrahydro-pyran-2-yl)-propoxy]-phenoxy}-propyl)-tetrahydro-pyran-2-yl]-methanol (tlc silica gel, Rf 0.44 in 50% EtOAc/LightPetroleum, ESMS (+ve) 1081 (M+Na)) as an oil (634 mg, 94%). This compound (1.6 g, 1.51 mmol) was dissolved in dry dichloromethane (25 ml) and triethylamine (589 µl, 4.23 mmol) and the mixture cooled to 0° C. whereupon phosphorous oxychloride (351 µl, 3.78 mmol) was added dropwise with stirring under an atmosphere of nitrogen. The mixture was allowed to warm to room temperature and stirred for 2 hours. The solvent was evaporated and the residue diluted with ether and centrifuged to remove insoluble salts. The supernatant was then evaporated and redissolved in a 1:1 mixture of acetone and water (20 ml) and kept at 45–50° C. for 2 hours. The solvent was removed under reduced pressure to give phosphoric acid mono-[3,4,5-tris-benzyloxy-6-(3-{3-[3-(3,4,5-tris-benzyloxy-6-phosphonooxymethyl-tetrahydro-pyran-2-yl)-propoxy]-phenoxy}-propyl)-tetrahydro-pyran-2-ylmethyl] ester, ESMS (+ve) 1219 (M+H), 1241 (M+Na). This compound was dissolved with 1% formic acid in 1:1 tetrahydrofuran and water (100 ml), 10% palladium on carbon (100 mg) added and hydrogenated at 40 psi overnight. The mixture was filtered through celite and the filtrate evaporated to dryness to give phosphoric acid mono-[3,4,5-trihydroxy-6-(3-{3-[3-(3,4,5-trihydroxy-6-phosphonooxymethyl-tetrahydro-pyran-2-yl)-propoxy]-phenoxy}-propyl)- tetrahydro-pyran-2-ylmethyl] ester, ESMS (−ve) 677 (M−H). From this was prepared the di sodium salt by dissolving this compound in a 1:1 solution of water and ethanol (2 ml) and dropwise addition of this solution to sodium acetate (269 mg, 3.28 mmol) dissolved in ethanol (50 ml). The resulting precipitate was isolated by centrifugation to give phosphoric acid mono-[3,4,5-trihydroxy-6-(3-{3-[3-(3,4,5-trihydroxy-6-phosphonooxymethyl-tetrahydro-pyran-2-yl)-propoxy]-phenoxy}-propyl)-tetrahydro-pyran-2-ylmethyl] ester, disodium salt as a white solid (850 mg, 83%). $^1$Hnmr (500 MHz, D$_2$O): δ 1.35–1.90 (m, 8H), 3.42–4.12 (m, 18H), 6.48 (s, 1H), 6.52 (d, J=8.0 Hz, 2H), 7.15 (t, J=8.0 Hz, 1H).

Example 15

Preparation of phosphoric acid mono-(6-{3-[3,4-dihydroxy-6-hydroxymethyl-5-(3,4,5-trihydroxy-6-hydroxymethyl-tetrahydro-pyran-2-yloxy)-tetrahydro-pyran-2-yloxy]-propyl}-3,4,5-trihydroxy-tetrahydro-pyran-2-ylmethyl) ester (Formula I; R=—(CH$_2$)$_3$—O-(1'-maltosyl)

To a stirred solution of (6-allyl-3,4,5-tris-benzyloxy-tetrahydro-pyran-2-yl)-methanol (prepared in Example 7) (22.7 g, 47.90 mmol) in dry pyridine (400 ml) at 0° C. was added diphenylphosphorylchloride (20 ml, 95.78 mmol) and the stirring was continued for 1 hour at 0° C. The mixture was allowed to gradually warm to room temperature, and stirring was continued for additional 1 hour. Water (150 ml) was then added and the mixture evaporated under reduced pressure. The residue was dissolved in chloroform (250 ml) and the solution was successively washed with water (100 ml), 5% hydrochloric acid (2×100 ml), saturated sodium bicarbonate (2×100 ml), water (100 ml), dried (sodium sulfate), filtered and evaporated under reduced pressure. The residue was chromatographed on a silica gel (0.040–0.063 mm) column (4×30 cm), eluted with petroleum spirit (bp 60–80°):ethyl acetate (3:2) to give phosphoric acid 6-allyl-3,4,5-tris-benzyloxy-tetrahydro-pyran-2-ylmethyl ester diphenyl ester (19.5 g, 60%), tlc silica gel Rf=0.75 (ethyl acetate/hexane=2:3); $^1$Hnmr (300 MHz, CDCl$_3$): δ 2.29 (m, 3H), 3.62 (m, 1H), 3.77 (m, 2H), 3.88 (m, 1H), 4.04 (m, 1H), 4.41–4.63 (m, 8H), 5.00 (m, 2H), 5.72 (m, 1H), 7.12–7.15 (m, 25H). This compound (10.02 g, 15.8 mmol) was dissolved in dry tetrahydrofuran (~100 ml) placed under nitrogen at 0° C. and to this was added a solution of borane in tetrahydrofuran (10M, ~1.5 eq, 33 ml). The reaction mixture was allowed to warm to room temperature and followed by thin layer chromatography. Upon completion the reaction mixture was poured onto an aqueous solution of sodium hydroxide (1M, 50 ml) to which was added sodium percarbonate (12.4 g, ~4 eq). The reaction mixture was stirred overnight and extracted with diethyl ether (2×100 ml). The combined organic layers were washed with water (150 ml), dried (sodium sulfate), filtered and evaporated under reduced pressure. The residue was chromatographed on silica gel (0.040–0.063 mm) column (4×30 cm), eluted with ethyl acetate to give phosphoric acid diphenyl ester 3,4,5-tris-benzyloxy-6-(3-hydroxy-propyl)-tetrahydro-pyran-2-ylmethyl ester (5.8 g, 56%). This compound (4.55 g, 6.35 mmol), tetramethylurea (733 mg, 6.31 mmol) and silver trifluoromethanesulfonate (1.62 g, 6.31 mmol) were stirred in dichloromethane (150 ml) under nitrogen over molecular sieves (4A°, 5 g) for 1 hour at room temperature, and then cooled to −20° C. A solution of hepta-O-acetylmaltosyl bromide (4.01 g, 5.73 mmol), (prepared in a similar manner to the general method of Malet et al., 1995, incorporated herein by reference) in dichloromethane (150 ml) was added dropwise. The mixture was stirred at −20° C. for 4 hours, then left overnight to reach room temperature, and filtered through celite. The filtrate was poured into ice-cold water and washed sequentially with saturated sodium bicarbonate (100 ml), water (50 ml), hydrochloric acid (100 ml), water (50 ml), saturated sodium bicarbonate (100 ml), and water (50 ml). The organic phase was dried (sodium sulfate), filtered and evaporated under reduced pressure to give crude phosphoric acid diphenyl ester 3,4,5-tris-benzyloxy-6-{2-[3,4-diacetoxy-6-acetoxymethyl-5-(3,4,5-triacetxy-6-acetoxymethyl-tetrahydro-pyran-2-yloxy)-tetrahydro-pyran-2-yloxy]-propyl}-tetrahydro-pyran-2-ylmethyl ester. This material was dissolved in methanol (150 ml), water (5 ml) and formic acid (5 ml) to which was added 10% palladium on charcoal. The resulting solution was shaken under hydrogen (55 psi) for 48 hours. The catalyst was removed by filtration and the solvent evaporated under reduced pressure. The residue was chromatographed on a silica gel (0.040–0.063 mm) column (4×20 cm), eluted with 10% methanol in ethyl acetate to give phosphoric acid diphenyl ester mono-(6-{2-[3,4-diacetoxy-6-acetoxymethyl-5-(3,4,5-triacetoxyroxy-6-acetoxymethyl-tetrahydro-pyran-2-yloxy)-tetrahydro-pyran-2-yloxy]-propyl}-3,4,5-trihydroxy-tetrahydro-pyran-2-ylmethyl) ester (1.6 g, 26% overall). Rf=0.5 (10% methanol in ethyl acetate); ESMS (+ve) 1095 (M+Na). A solution of this material (1.6 g, 1.49 mmol) in a 1:1 mixture of trifluoro acetic acid and acetic acid (30 ml) was shaken under a hydrogen atmosphere (40 psi) in the presence of activated Adams catalyst (PtO$_2$ (83%); 750 mg, 2.2 mmol) for 3 hours. The catalyst was filtered off and the solvent evaporated to dryness under reduced pressure to give phosphoric acid mono-(6-{2-[3,4-diacetoxy-6-acetoxymethyl-5-(3,4,5-triacetoxy-6-acetoxymethyl-tetrahydro-pyran-2-yloxy)-tetrahydro-pyran-2-yloxy]-propyl}-3,4,5-trihydroxy-tetrahydro-pyran-2-ylmethyl) ester (1.24 g, 90.5%), ESMS (−ve) 919 (M−H). This material was stirred with sodium methoxide (9 eq) in methanol (50 ml) and water (5 ml) for 8 hours. Sodium ions were removed by Dowex 50 X8 H+ form ion exchange resin. The ion exchange resin was filtered off and the filtrate taken to dryness under reduced pressure. The residue was dissolved in water (3 ml) and this was added, dropwise with stirring, to a solution of sodium acetate (1.1 eq) in ethanol (50 ml). The precipitate was filtered off to give phosphoric acid mono-(6-{3-[3,4-dihydroxy-6-hydroxymethyl-5-(3,4,5-trihydroxy-6-hydroxymethyl-tetrahydro-pyran-2-yloxy)-tetrahydro-pyran-2-yloxy]-propyl}-3,4,5-trihydroxy-tetrahydro-pyran-2-ylmethyl) ester monosodium salt (675 mg, 80%), $^1$Hnmr (300 MHz, D$_2$O) ∂ 1.40–1.80 (m, 4H), 3.10 (m, 1H), 3.23 (m, 1H), 3.37–4.10 (m, 19H), 4.29 (m, 1H), 5.20 (m, 1H); ESMS (−ve) 625 (M−H).

Example 16

Preparation of phosphoric acid mono-(6-{2-[3,4-dihydroxy-6-hydroxymethyl-5-(3,4,5-trihydroxy-6-hydroxymethyl-tetrahydro-pyran-2-yloxy)-tetrahydro-pyran-2-yloxy]-ethyl}-3,4,5-trihydroxy-tetrahydro-pyran-2-ylmethyl) ester monosodium salt. (Formula I; R=—(CH$_2$)$_2$—O-(1'-maltosyl).

Phosphoric acid 6-allyl-3,4,5-tris-benzyloxy-tetrahydro-pyran-2-ylmethyl ester diphenyl ester (prepared in Example 15) (10 g, 14.16 mmol) in dichloromethane (75 ml) water (75 ml) and acetic acid (15.6 ml) was added Aliquat 336 (0.93 g) and the reaction vessel was cooled to 0° C. and potassium permanganate (8.3 g, 52.7 mmol) was added in two portions. The ice bath was removed, and the reaction was stirred for 24 hours at room temperature. Sodium sulfite (9.31 g, 57.4 mmol) was added and the mixture was partitioned between water (150 ml) and dichloromethane (200 ml). The aqueous layer was extracted with dichloromethane (150 ml), and the combined organic extracts were washed with brine (200 ml), dried (sodium sulfate), filtered and evaporated under reduced pressure. The residue was chromatographed on a silica gel (0.040–0.063 mm) column (4×20 cm), eluted with ethylacetate:methanol (19:1) to give [3,4,5-tris-benzyloxy-6-(bis-phenoxy-phosphoryloxymethyl)-tetrahydro-pyran-2-yl]-acetic acid (9.6 g, 93.8%). To a stirred solution of this compound (9.0 g, 12.45 mmol) and BOP reagent (5.84 g, 13.16 mmol) in tetrahydrofuran (50 ml) at room temperature was added diisopropylethylamine (2.62 ml, 15.03 mmol). The resulting solution was stirred for 5 minutes, then sodium borohydride (490 mg, 12.9 mmol) was added. After stirring for 20 minutes, the solvent was evaporated and the residue was taken up in ethylacetate (300 ml) and washed with 5% hydrochloric acid (2×100 ml), saturated sodium bicarbonate (2×100 ml) and brine (100 ml), dried (sodium sulfate), filtered and evaporated. The residue was chromatographed on a silica gel (0.040–0.063 mm) column (4×20 cm), eluted with petroleum spirit (bp 60–80°): ethyl acetate (1:1) to give phosphoric acid diphenyl ester 3,4,5-tris-benzyloxy-6-(2-hydroxy-ethyl)-tetrahydro-pyran-2-ylmethyl ester (4.9 g, 56%), tlc silica gel, $R_f$ 0.42 (ethyl acetate/petroleum spirit bp 60–80 1:1). $^1$Hnmr (300 MHz, CDCl$_3$): δ 1.65 (m, 1H), 1.98 (m, 1H), 3.50–3.80 (m, 5H), 4.00–4.30 (m, 3H), 4.45–4.68 (m, 6H), 4.85 (m, 1H), 7.00–7.70 (m, 25H); ESMS (+ve) 711 (M+H), 733 (M+Na). This compound (3.64 g, 5.13 mmol), tetramethylurea (600 mg, 5.17 mmol) and silver trifluoromethanesulfonate (1.32 g, 5.14 mmol) were dissolved in dichloromethane (100 ml) and stirred under nitrogen over molecular sieves (4A°, 5 g) for 1 hour at room temperature, and then cooled to −20° C. To this solution was added hepta-O-acetylmaltosyl bromide (prepared in Example 15) (5.82 g, 5.14 mmol) in dichloromethane (100 ml) dropwise. The mixture was stirred at −20° C. for 4 hours, then left overnight to reach room temperature, and filtered through celite. The filtrate was poured into ice-cold water and washed sequentially with saturated sodium bicarbonate (100 ml), water (50 ml), hydrochloric acid (100 ml), water (50 ml), saturated sodium bicarbonate (100 ml), and water (50 ml). The resulting solution was dried (sodium sulfate), filtered and evaporated under reduced pressure. The residue was chromatographed on a silica gel (0.040–0.063 mm) column (4×50 cm), eluted with petroleum spirit (bp 60–80°): ethyl acetate (3:2) to give phosphoric acid diphenyl ester 3,4,5-tris-benzyloxy-6-{2-[3,4-diacetoxy-6-bacetoxymethyl-5-(3,4,5-triacetoxy-6-acetoxymethyl-tetrahydro-pyran-2-yloxy)-tetrahydro-pyran-2-yloxy]-ethyl}-tetrahydro-pyran-2-ylmethyl ester (3.07 g, 34%). Treatment of this compound in a similar manner to that for phosphoric acid diphenyl ester mono-(6-{2-[3,4-diacetoxy-6-acetoxymethyl-5-(3,4,5-triacetoxyroxy-6-acetoxymethyl-tetrahydro-pyran-2-yloxy)-tetrahydro-pyran-2-yloxy]-propyl}-3,4,5-trihydroxy-tetrahydro-pyran-2-ylmethyl) ester in Example 15 gave phosphoric acid mono-(6-{2-[3,4-dihydroxy-6-hydroxymethyl-5-(3,4,5-trihydroxy-6-hydroxymethyl-tetrahydro-pyran-2-yloxy)-tetrahydro-pyran-2-yloxy]-ethyl}-3,4,5-trihydroxy-tetrahydro-pyran-2-ylmethyl) ester monosodium salt. (72% overall). $^1$Hnmr (300 MHz, D$_2$O) ∂ 1.64–2.10 (m, 2H), 3.14 (m, 1H), 3.23 (m, 1H), 3.40–4.20 (m, 19H), 4.30 (m, 1H), 5.25 (m, 1H); ESMS (−ve) 611 (M−H).

Example 17

Preparation of 3-(2-tert-Butoxycarbonylamino-4-methyl-pentanoylamino)-N-{2-methyl-1-[3-(3,4,5-trihydroxy-6-phosphonooxymethyl-tetrahydro-pyran-2-yl)-propylcarbamoyl]-propyl}-succinamic acid, mono sodium salt

[6-(3-Amino-propyl)-3,4,5-tris-benzyloxy-tetrahydro-pyran-2-yl]-methanol (from Example 12) (3.8 g, 6.3 mmol) was reacted with Boc-valine (1.37 g, 6.3 mmol) activated with BOP reagent (2.8 g, 6.3 mmol) and diisopropylethylamine (1.7 ml, 10 mmol) in tetrahydrofuran (10 ml). After 2 hours the solvent was removed under reduced pressure and ethyl acetate (100 ml) added to the oily residue which was subsequently washed with 1M hydrochloric acid (2×100 ml), saturated sodium bicarbonate (2×100 ml) and brine (100 ml), dried over anhydrous sodium sulfate, and evaporated to dryness. The residue was purified on a rapid vacuum silica gel (0.040–0.063 mm; 100 g) column (70×200 mm) eluted with light petroleum (200 ml), 25% ethyl acetate in light petroleum (200 ml), 50% ethyl acetate in light petroleum (2×200 ml), 75% ethyl acetate in light petroleum (2×200 ml), and 100% ethyl acetate (2×100 ml) to give {2-methyl-1-[3-(3,4,5-tris-benzyloxy-6-hydroxymethyl-tetrahydro-pyran-2-yl)-propylcarbamoyl]-propyl}-carbamic acid tert-butyl ester (tlc silica gel, Rf 0.13 in 50% EtOAc/Light Petroleum, ESMS (+ve) 713 (M+Na)) as an oil (2.4 g, 54%). This compound (1.2 g, 1.7 mmol) was reacted with a 1:1 mixture of trifluoroacetic acid and dichloromethane (10 ml) for 1 hour to remove the Boc protecting group. The reaction mixture was evaporated to dryness, diluted with dichloromethane (20 ml) and evaporated to remove all traces of trifluoroacetic acid. The crude product was reacted with Boc-aspartic acid, gamma-benzyl ester (581 mg, 1.8 mmol) activated with BOP reagent (79 6mg, 1.8 mmol) and diisopropylamine (0.869 ml, 5 mmol) in tetrahydrofuran (20 ml). After 2 hours the solvent was removed under reduced pressure and ethyl acetate (100 ml) added to the oily residue which was subsequently washed with 1M hydrochloric acid (2×100 ml), saturated sodium bicarbonate (2×100 ml) and brine (100 ml), dried over anhydrous sodium sulfate, and evaporated to dryness to give 3-tert-butoxycarbonylamino-N-{2-methyl-1-[3-(3,4,5-tris-benzyloxy-6-hydroxymethyl-tetrahydro-pyran-2-yl)-propylcarbamoyl]-propyl}-succinamic acid benzyl ester, ESMS (+ve) 896 (M+H). This compound (approx. 1.7 mmol) was reacted with a 1:1 mixture of trifluoroacetic acid and dichloromethane (10 ml) for 1 hour to remove the Boc protecting group. The reaction mixture was evaporated to dryness, diluted with dichloromethane (20 ml) and evaporated to remove all traces of trifluoroacetic acid. The crude product was reacted with Boc-leucine (448 mg, 1.8 mmol) activated with BOP reagent (796 mg, 1.8 mmol) and diisopropylamine (0.869 ml, 5 mmol) in tetrahydrofuran (20 ml). After 2 hours the solvent was removed under reduced pressure and ethyl acetate (100 ml) added to the oily residue which was subsequently washed with 1M hydrochloric acid (2×100 ml), saturated sodium bicarbonate (2×100 ml) and brine (100 ml), dried over anhydrous sodium sulfate, and evaporated to dryness. The residue was purified on a rapid vacuum silica gel (0.040–0.063 mm; 100 g) column (70×200 mm) eluted with light petroleum (200 ml), 25% ethyl acetate in light petroleum (200 ml), 50% ethyl acetate in light petroleum (2×200 ml), 75% ethyl acetate in light petroleum (2×200 ml), and 100% ethyl acetate (2×100 ml) to give 3-(2-tert-butoxycarbonylamino-4-methyl-pentanoylamino)-N-{2-methyl-1-[3-(3,4,5-tris-benzyloxy-6-hydroxymethyltetrahydro-pyran-2-yl)-propylcarbamoyl]-propyl}-succinamic acid benzyl ester (tlc silica gel, Rf 0.42 in EtOAc, ESMS (+ve) 1009 (M+H), 1031 (M+Na)) as a white solid (850 mg, 48% combined for 2 deprotection and coupling steps). This compound (850 mg, 0.84 mmol) was dissolved in dry dichloromethane (10 ml) and triethylamine (0.557 ml, 4 mmol) and the mixture cooled to 0° C. whereupon phosphorous oxychloride (0.102 ml, 1.1 mmol) was added dropwise with stirring under an atmosphere of nitrogen. The mixture was allowed to warm to room temperature and stirred for 2 hours. The solvent was evaporated and the residue diluted with ether and centrifuged to remove insoluble salts. The supernatant was then evaporated and redissolved in a 1:1 mixture of acetone and water (20 ml) and kept at 45–50° C. for 2 hours. The solvent was removed under reduced pressure to give 3-(2-tert-butoxycarbonylamino-4-methyl-pentanoylamino)-N-{2-methyl-1-[3-(3,4,5-tris-benzyloxy-6-phosphonooxymethyl-tetrahydro-pyran-2-yl)-propylcarbamoyl]-propyl}-succinamic acid benzyl ester, ESMS (−ve) 1088 (M−H). This compound was dissolved with 1% formic acid in a 1:1 mixture of tetrahydrofuran and water (100 ml), 10% palladium on carbon (100 mg) added and hydrogenated at 40 psi overnight. The mixture was filtered through celite and the filtrate evaporated to dryness to give 3-(2-tert-butoxycarbonylamino-4-methyl-pentanoylamino)-N-{2-methyl-1-[3-(3,4,5-trihydroxy-6-phosphonooxymethyl-tetrahydro-pyran-2-yl)-propylcarbamoyl]-propyl}-succinamic acid, ESMS (−ve) 728 (M−H). From this was prepared the mono sodium salt by dissolving this compound in a 1:1 solution of water and ethanol (2 ml) and dropwise addition of this solution to sodium acetate (270 mg, 3.3 mmol) dissolved in ethanol (50 ml). The resulting solution was evaporated to dryness to give 3-(2-tert-butoxycarbonylamino-4-methyl-pentanoylamino)-N-{2-methyl-1-[3-(3,4,5-trihydroxy-6-phosphonooxymethyl-tetrahydro-pyran-2-yl)-propylcarbamoyl]-propyl}-succinamic acid, monosodium salt as a white solid (490 mg, 80%). $^1$Hnmr (500 MHz, D$_2$O): δ 0.73–0.84 (m, 12H), 1.28 (s, 9H), 1.35–1.70 (m, 7H), 1.97 (m, 1H), 2.45 2.69 (m, 2H), 3.00–3.19 (m, 2H), 3.45–3.98 (m, 9H), 4.53 (m, 1H).

Example 18

Preparation of Phosphoric acid mono-[3,4,5-trihydroxy-6-(2-oxo-propyl)-tetrahydro-pyran-2-yl methyl] ester (Formula I; R=CH$_2$COCH$_3$)

Using a variation of the method described by (Rodrigues et al, 2000) to a solution of D-Mannose (18 g, 100 mmol), dissolved in distilled water (400 ml), was added sodium bicarbonate (12.6 g; 150 mmol). 2,4-Pentanedione (12.32 ml, 120 mmol) was added to the solution and the mixture allowed to stir at 90° C. for 12 hours. Afterwards the solution was washed with dichloromethane (2 ×250 ml) and the aqueous phase treated with Dowex ion exchange resin (50W-X8, H$^+$ form) until the pH was stable at ~4. The resin was filtered off through a sintered glass funnel and washed with distilled water (2×500 ml). The combined filtrate and washings were evaporated under reduced pressure to give crude 1-(3,4,5-trihydroxy-6-hydroxymethyl-tetrahydro-pyran-2-yl)-propan-2-one, ESMS (−ve) 219 (M−H). This material (10.9 g, 49.5 mmol), was dissolved in pyridine (200 ml), the mixture cooled to 0° C. and with stirring, under dry nitrogen, triphenylmethyl chloride (2.5 eq., 34.4 g) was added slowly. The reaction mixture was warmed to 50° C. and stirred for 16 hours After cooling, acetic anhydride (47 ml) was added and the solution stirred for a further 60 minutes at 50° C. The mixture was then poured into iced water (200 ml) and the solution was extracted with dichloromethane (3×200 ml). The combined organic layers were successively washed with water (200 ml), saturated sodium bicarbonate (200 ml) and water (200 ml). The organic phase was dried (sodium sulfate), filtered and the filtrate evaporated under reduced pressure to give acetic acetic acid-4,5-diacetoxy-6-(2-oxo-propyl)-2-trityloxymethyl-tetrahydro-pyran-3-yl ester, ESMS (+ve) 611 (M+Na). The residue was dissolved in dichloromethane (300 ml) and anhydrous ferric chloride (7.8 g) was added. After stirring at room temperature for 2 hours, the organic solution was washed with water (3×200 ml). The organic layer was dried (sodium sulfate), filtered and the filtrate evaporated under reduced pressure. The residue was taken up in 40–60 petroleum spirits (xx ml), and silica gel (0.040–0.063 mm; 20 g) was added. The slurry was added to the top of a silica gel (0.040–0.063 mm; 100 g) column (70×200 mm) and eluted by vacuum as follows: petroleum spirits (bp 40–60° C.) (400 ml, f1), 5% ethyl acetate/petroleum spirits (400 ml, f2), 10% ethyl acetate/pet spirit (400 ml, f3), 25% ethyl acetate/pet spirit (400 ml, f4), 50% ethyl acetate/pet spirit (800 ml, f5[400 ml], f6[400 ml]), 100% ethyl acetate (800 ml, f7[400 ml], f8[400 ml], 5% methanol/dichloromethane (400 ml, f9), and 10% methanol/dichloromethane (400 ml, f10). Acetic acid-4,5-diaectoxy-2-hydroxymethyl-6-(2-oxo-propyl)-tetrahydro-pyran-3-yl ester was found in f6–f8 (3.1 g, 18% overall), ESMS (+ve) 369 (M+Na). This compound (630 mg 1.82 mmol) was dissolved in dichloromethane (20 ml) and triethylamine (2 eq, 0.5 ml) and the mixture cooled to 0° whereupon phosphorus oxychloride (0.7 ml) was added dropwise with stirring under a dry nitrogen atmosphere. The mixture was allowed to warm to room temperature and stirred overnight. The mixture was filtered and evaporated to dryness under reduced pressure. The residue was dissolved in a 1:1 mixture of acetone and water (10 ml) and kept at 45–50° for 2 hours. After evaporation to dryness the residue was evaporated from 40 ml of ethanol. The residue was stirred at room temperature for 1 hour in water (5 ml) that contained sodium methoxide (around 5 eq, 0.5 g), after which it was treated with Dowex ion exchange (50W-X8, H$_+$form) to remove sodium ions. The resin was filtered through a sintered glass funnel and washed with distilled water (2×5 ml). The combined filtrate and washings were evaporated under reduced pressure and the residue evaporated from ethanol (50 ml). This material was then dissolved in a minimum of water and added dropwise to a solution of sodium acetate (1.1 eq, 164 mg) in ethanol (40 ml). The resulting precipitate was pelleted by centrifugation and the ethanol decanted off, the solid was washed with diethyl ether (2×50 ml) and dried to give phosphoric acid mono-[3,4,5-trihydroxy-6-(2-oxo-propyl)-tetrahydro-pyran-2-yl methyl] ester monosodium salt (291 mg, 50%).

Example 19

Inhibition of T-Lymphocyte Migration Across Rat Brain Endothelial Cell Layer

Vascular endothelial cells were isolated from rat brain capillaries taken from 6 to 8 week old Lewis rats according to the method of Risau et al. (Risau, W., Engelhardt, B., and Wekerle, H., (1990). *Journal of Cell Biology*, vol 110, p 1757–1766, which is incorporated herein by reference). Colonies of endothelial cells were purified from astroglial cells and pericytes by a Thy1.1-mediated complement lysis also after the method of Risau et al. (vide supra). The endothelial colonies, according to methods known in the art, were grown in Dulbecco's minimum essential medium (DMEM) high glucose supplemented, with 20% fetal calf serum (FCS), glutamine, pyruvate, nonessential amino acids, 4-(2-hydroxyethyl)-1-piperazine ethane sulfonic acid buffer (HEPES), kanamycin, amphotericin, heparin (all from Gibco) and 150 micrograms/ml endothelial growth supplement (Collaborative Biomedical Products). Upon reaching confluence, the endothelial cultures were washed with 0.2% EDTA in phosphate buffered saline (PBS), trypsinized (Trypsin-EDTA, 0.1% final concentration, Gibco), washed and again incubated with anti-Thy1.1 antibody for 40 minutes, washed and incubated with complement sufficient to lyse all Thy1.1+ cells (Behringwerke, AG, Marburg, Germany) at room temperature, washed and plated on matrigel-coated 6.5 mm Transwells, 5 mm pore size (Corning Costar Corporation, Cambridge, Mass.). The endothelial cell characteristics and confluence of the monolayer were checked by measuring the electrical resistance (World Precision Instruments, New Haven, U.S.A., model EVOM-G) and by staining with FITC-labeled phalloidin (Sigma). In order to study the effect of the agents of the present invention on T lymphocyte migration, myelin basic protein (MBP)-specific T lymphocyte cell lines were generated according to the method of Ben-Nun et al. (Ben-Nun, A., Wekerle, H. and Cohen, I. R., 1981). The rapid isolation of clonable antigen-specific T lymphocyte lines capable of mediating autoimmune encephalomyelitis. European Journal of Immunology. 1981, 11(3), 195–199; incorporated herein by reference) from the lymph nodes of Lewis rats that had been immunised with MBP in Freund's complete adjuvant. These cells were used for migration studies during the first 4 days of their propagation in IL-2 containing medium, following antigen (MBP) restimulation in the presence of antigen-presenting cells from irradiated spleen cells or thymocytes taken from normal Lewis rats. The antigen-activated T lymphocytes were radio-labelled with sodium chromate ($^{51}$Cr, 37 MBq/ml, Amersham, UK) for 30 minutes at 37° C. with occasional agitation, they were then washed three times with the DMEM culture medium and placed into the upper chamber of the Transwells at $5\times10^5$ cells in 100 microliters of migration medium. Test and control substance were included in the upper wells at final concentrations of 0.1, 1 and 10 mM. Cell migration was monitored by light microscopy in order to gauge progress of the experiment. The experiment was terminated after 6 hours in culture, whereupon the undersurface of the membrane filters were rinsed twice with 100 microliters of ice-cold 0.2% EDTA in PBS and added to the contents of the lower chamber of the well. The combined material was transferred into scintillation vials and the radioactivity of each tube determined by counting for 1 minute in a Packard Auto-Gamma 5650 (IL, USA) gamma counter. Each test and the control substance (glucose 6-phosphate) and no treatment were assessed in triplicate.

The results from a typical experiment are shown in Table 1. The value for the negative control (glucose 6-phosphate) was not statistically different from no treatment. Inhibition values are in comparison with the negative control.

TABLE 1

| Test substance [10 mmolar] | % inhibition ± SEM |
| --- | --- |
| Ethyl (3,4,5-trihydroxy-6-phosphonooxymethyl-tetrahydro-pyran-2-yl)-acetic acid ester | 70 ± 4 |
| Pentyl (3,4,5-trihydroxy-6-phosphonooxymethyl-tetrahydro-pyran-2-yl)-acetic acid ester | 80 ± 4 |
| Phosphoric acid mono-(6-propyl-3,4,5-trihydroxy-tetrahydro-pyran-2-ylmethyl) ester | 64 ± 4 |
| (3,4,5-Trihydroxy-6-phosphonooxymethyl-tetrahydro-pyran-2-yl)-acetic acid | 32 ± 2 |
| negative control - glucose 6-phosphate | 0 ± 5 |

Example 20

Inhibition of Lymphocyte Migration into Lymphoid Tissue

In the present example, spleens from specific pathogen free 6–8 week old female Balb/C mice [19–21 g] were used to prepare a single cell suspension in the usual manner in mixed lymphocyte culture medium (DMEM plus glucose, folic acid, L-asparagine, sodium bicarbonate, L-glutamine, sodium pyruvate, HEPES, 2-mercaptoethanol, penicillin, streptomycin, neomycin, and 2% fetal calf serum) by pushing through a stainless steel screen. Following cell collection the red blood cells were lysed in the usual manner by treating with a solution of ammonium chloride, EDTA and sodium hydrogen carbonate (pH 7.3) and the preparation strained (Falcon 2350 cell strainer). All cell preparative steps were performed on ice.

In order to deplete the preparation of B lymphocytes, the cells were suspended in purified rat anti-mouse CD45/B220 antibody (RA3-6B2 clone; PharMingen, USA) at a concentration of $4\times10^7$ cells per ml and incubated on ice for 20 minutes. An equal volume of mixed lymphocyte culture medium (as above) was then added and the cells centrifuged (200× g) and resuspended at a concentration of $1\times10^7$ cells per ml in BioMag goat ant-rat IgG (H&L) linked to magnetic beads (Bio Mag; Perseptive Diagnostics, Polysciences Inc, USA). Following a 20 minute incubation on ice, with agitation every 5 minutes, the goat anti-rat IgG/antibody complex was removed using magnetic separation (Dynal MPC-6, Dynal, USA). The magnetic separation procedure was repeated 4 times giving a cell population containing approximately 80–90% T lymphocytes (determined by FACS analysis).

The cells were then washed in Hanks media, resuspended in 5 ml of Hanks, and radio-labelled for 30 minutes at 37° C. with sodium chromate solution ($^{51}$Cr, 34 MBq/ml, Amersham, UK). The labelled cells were washed in PBS centrifuged (200×g) and a portion were resuspended at a concentration of $3\times10^7$ cells/ml in either PBS (negative control), or PBS containing the test compound (25 mg/ml), and stored on ice. Balb/C mice in the negative control and treatment groups received a volume of 0.2 ml of the labelled cell preparation by a lateral tail vein injection. Negative control mice received 0.2 ml of PBS together with $6\times10^6$ $^{51}$chromium-labelled lymphocytes, and mice from the treated groups received an intravenous dose of 5 mg of the test compound together with 6 million $^{51}$chromium-labelled lymphocytes. Cell viability was confirmed throughout the procedures by trypan blue exclusion assay. All groups of mice were weight matched (±0.5 g).

Spleens from the recipient mice were removed 1.5 hours after injection and the cell-associated radioactivity (CPM)

determined using a gamma counter (Packard Auto-Gamma 5650. IL, USA). Results (inhibition of lymphocyte migration into the spleen) were expressed as a percentage reduction in the CPM of the spleens from treated animals compared with negative controls.

The compounds tested, and the degree of inhibition of lymphocyte migration into the spleen is shown in Table 2.

TABLE 2

Percent inhibition (relative to negative controls) of lymphocyte migration into spleens.

| Compound | Percent Inhibition |
|---|---|
| ethyl (3,4,5-trihydroxy-6-phosphonooxymethyl-tetrahydro-pyran-2-yl) acetate sodium salt | 32.4 |
| (3,4,5-trihydroxy-6-phosphonooxymethyl-tetrahydro-pyran-2-yl) acetic acid disodium salt | 85.5 |
| 6-cyano-3,4,5-trihydroxy-tetrahydro-pyran-2-ylmethyl) phosphoric acid ester disodium salt | 45.0 |
| mono-(3,4,5-trihydroxy-tetrahydro-pyran-2-ylmethyl) phosphoric acid ester mono sodium salt | 68.0 |

Example 21

Inhibiton of in vivo Migration of T Lymphocytes into Extra Lymphatic Tissues

In the present example spleens from specific pathogen-free 6–8 week old female Balb/C mice [19–21 g] which had been sensitised one week earlier with picryl chloride (1% in ethanol applied onto a 1 cm$^2$ shaved area of the abdomen) were used to prepare a single cell suspension in the usual manner in mixed lymphocyte culture medium (DMEM plus glucose, folic acid, L-asparagine, sodium bicarbonate, L-glutamine, sodium pyruvate, HEPES, 2-mercaptoethanol, penicillin, streptomycin, neomycin, and 2% fetal calf serum) by pushing through a stainless steel screen. Following cell collection the red blood cells were lysed by treating with a solution of ammonium chloride, EDTA and sodium hydrogen carbonate (pH 7.3) at 4° C. for 2 minutes and the preparation strained (Falcon 2350 cell strainer). All cell preparative steps were performed on ice.

In order to deplete the preparation of B lymphocytes, the cells were suspended in purified rat anti-mouse CD45/B220 antibody (RA3-6B2 clone; PharMingen, USA) at a concentration of $4 \times 10^7$ cells per ml and incubated on ice for 20 minutes. An equal volume of mixed lymphocyte culture medium (as above) was then added and the cells centrifuged (200×g) and resuspended at a concentration of $1 \times 10^7$ cells per ml in BioMag goat ant-rat IgG (H&L) linked to magnetic beads (Bio Mag; Perseptive Diagnostics, Polysciences Inc, USA). Following a 20 minute incubation on ice, with agitation every 5 minutes, the goat anti-rat IgG/antibody complex was removed using magnetic separation (Dynal MPC-6, Dynal, USA). The magnetic separation procedure was repeated 4 times giving a cell population containing approximately 85–90% T lymphocytes and less than 1% B cells (determined by FACS analysis).

The cells were then washed in Hanks medium, resuspended in 5 ml of Hanks, and radio-labelled for 30 minutes at 37° C. with sodium chromate solution ($^{51}$Cr, 34 MBq/ml, Amersham, UK). The labelled cells were washed in PBS centrifuged (200×g) and resuspended at a concentration of $3 \times 10^7$ cells/ml in PBS. Recipient mice (specific pathogen-free 6–8 week old female Balb/C mice [19–21 g]) were divided into two groups of four mice each that were weight matched (±0.5 g). One group was injected with the test compound dissolved in 0.2 ml of normal saline, one was injected with 0.2 ml of normal saline by intravenous injection immediately prior to receiving a suspension of the chromium labelled T lymphocytes, $6 \times 10^6$ cells suspended in 0.2 ml of PBS intravenously. Viability of the injected cells was confirmed throughout the procedures by trypan blue exclusion assay. One hour prior to this procedure the mice in each group had their right ears treated with picryl chloride (0.1% in ethanol) in order to induce the injected cells to migrate there. It is understood that further injections of the test agent, the positive control and saline can be given at later time points, depending upon the duration of the experiment.

Between 9 and 10 hours after passaging the labelled T cells, the recipient mice were euthanased by lethal carbon dioxide inhalation, their right and left ears were removed and the cell-associated radioactivity (CPM) in each of the ears determined using a gamma counter (Packard Auto-Gamma 5650. IL, USA). Results (inhibition of lymphocyte migration into the right ear) were expressed as a percentage reduction in the CPM of the right ears from treated animals compared with the right ears of the negative controls. In order to control for non-specific migration of cells, the radioactivity values from the left ears were subtracted from the counts obtained in the right ear of the same animal prior to determining the mean for each group.

Results from a typical experiment are shown in Table 3.

TABLE 3

| Test substance 5 mg per mouse | Route of delivery | Percent inhibition of T cell migration |
|---|---|---|
| Phenylethyl (3,4,5-trihydroxy-6-phosphonooxy-methyl-tetrahydro-pyran-2-yl)-acetic acid es | IV | 26.1 |

Example 22

Blocking the Clinical Effects of in vivo Migration of T Lymphocytes into Extra Lymphatic Tissues Inhibition of T lymphocyte migration into extra lymphoid tissue, such as that demonstrated in Example 19, can alter the clinical manifestations associated with such cell migration. The clinical signs associated with such cell migration include tissue swelling. Thus, when inflammatory cells migrate into extra lymphatic tissues these tissues undergo swelling and induration and such changes are directly due, to a large extent, to the rapid accumulation of newly arrived cells in the affected tissue.

In the present Example, a murine model of Type IV hypersensitivity or delayed-type hypersensitivity (DTH) response to cutaneous contact with the chemical hapten 2,4-dinitrofluorobenzene (DNFB) (Aldrich Chemical Company Inc, USA) was used as a model to measure the anti-inflammatory effects of compounds of the present invention. Specific pathogen-free 8–12 week old female Balb/C mice, weighing 19–21 g, were sensitised in a similar manner to that described by Klimuk et al., (Klimuk et al., 1999) by applying a solution of DNFB (0.5% in acetone:olive oil (4:1, v/v); 30 microliters,) onto a 2 cm$^2$ shaved area of the abdomen. After 7 days, the animals were anesthetised with diethyl ether and 8 microliters of DNFB (0.35% in acetone:olive oil (4:1, v/v) was applied to the dorsal and ventral surfaces of the right pinna. Prior to regaining consciousness, the mice were implanted intraperitoneally with Alzet 2001 mini-osmotic pumps (Alza Corp., Palo Alto Calif., USA) containing phosphoric acid mono-[6-(3-hexyloxy-propyl)-3,4,5-trihydroxy-tetrahydro-pyran-2-ylmethyl] ester, sodium salt in normal saline. The dose delivered was 50 mg/kg/day. Control animals for this group received saline delivered in identical mini-osmotic pumps. A second experimental group of mice received phosphoric acid mono-[3-(3,4,5-trihydroxy-6-phosphonooxymethyl-tetrahydro-pyran-2-yl)-propyl] ester disodium salt via one-week delivery Alzet 2001 mini-osmotic pumps implanted intraperitoneally. This compound was delivered at a dose of 40 mg/kg/day. Control animals for this group received saline delivered in identical mini-osmotic pumps. In a third experiment a separate group of mice received (3,4,5-trihydroxy-6-phosphonooxymethyl-tetrahydro-pyran-2-yl)-acetic acid disodium salt via one-week delivery Alzet 2001 mini-osmotic pumps that were placed intraperitoneally. This compound was delivered at 45 mg/kg/day. The control group for this experiment received identical mini-osmotic pumps containing normal saline. In a fourth experiment a group of mice received 3-phenyl-2-[2-(3,4,5-trihydroxy-6-phosphonooxymethyl-tetrahydro-pyran-2-yl)-acetylamino]-propionic acid monosodium salt via one-week delivery Alzet 2001 mini-osmotic pumps that were placed subcutaneously. This compound was delivered at 62 mg/kg/day. The control group for this experiment received identical mini-osmotic pumps containing normal saline. In a fifth experiment a group of mice received hexanoic acid 3-(3,4,5-trihydroxy-6-phosphonooxymethyl-tetrahydro-pyran-2-yl)-propyl ester sodium salt via one-week delivery Alzet 2001 mini-osmotic pumps that were placed subcutaneously. This compound was delivered at 40 mg/kg/day. The control group for this experiment received identical mini-osmotic pumps containing normal saline.

Twenty-four hours after challenge the mice were lightly anesthetised with diethyl ether and the thickness of the left and right pinnae measured (in millimeters) using a dial gauge micrometer (Interapid, Switzerland). Care was taken to measure only the outer two thirds of the ear. The increase in ear thickness initiated by the DTH response was determined by subtracting the measurement of the left ear (untreated) from the right ear (challenged).

The results obtained from this experiment are outlined in Table 4. In Table 4, values in the columns labeled Left and Right are measurements of ear thickness in millimeters of the control and challenged ears respectively.

TABLE 4

| Control | Left | Right | Difference | Treated | Left | Right | Difference |
|---|---|---|---|---|---|---|---|
| Effect of treatment with phosphoric acid mono-[6-(3-hexyloxy-propyl)-3,4,5-trihydroxy-tetrahydro-pyran-2-ylmethyl] ester sodium salt on DTH. | | | | | | | |
| 1 | 0.22 | 0.37 | 0.15 | 1 | 0.22 | 0.3 | 0.08 |
| 2 | 0.2 | 0.27 | 0.07 | 2 | 0.22 | 0.32 | 0.1 |
| 3 | 0.2 | 0.3 | 0.1 | 3 | 0.2 | 0.25 | 0.05 |
| 4 | 0.21 | 0.34 | 0.13 | 4 | 0.22 | 0.25 | 0.03 |
| 5 | 0.22 | 0.26 | 0.04 | 5 | 0.21 | 0.26 | 0.05 |
| Mean | | | 0.098 | | | | 0.062 |

Mean percentage decrease in ear swelling in treated animals: 36.7%
Effect of treatment with phosphoric acid mono-[3-(3,4,5-trihydroxy-6-phosphonooxymethyl-tetrahydro-pyran-2-yl)propyl] ester disodium salt on DTH.

| 1 | 0.22 | 0.31 | 0.09 | 1 | 0.21 | 0.28 | 0.07 |
| 2 | 0.21 | 0.31 | 0.10 | 2 | 0.22 | 0.25 | 0.03 |

TABLE 4-continued

| Control | Left | Right | Difference | Treated | Left | Right | Difference |
|---|---|---|---|---|---|---|---|
| 3 | 0.21 | 0.30 | 0.09 | 3 | 0.21 | 0.23 | 0.02 |
| 4 | 0.21 | 0.24 | 0.03 | 4 | 0.22 | 0.28 | 0.06 |
| 5 | 0.21 | 0.33 | 0.12 | 5 | 0.21 | 0.33 | 0.12 |
| Mean | | | 0.086 | | | | 0.060 |

Mean percentage decrease in ear swelling in treated animals: 30%
Effect of treatment with (3,4,5-trihydroxy-6-phosphonooxymethyltetrahydro-pyran-2-yl)-acetic acid disodium salt on DTH.

| 1 | 0.2 | 0.29 | 0.09 | 1 | 0.21 | 0.27 | 0.06 |
| 2 | 0.21 | 0.29 | 0.08 | 2 | 0.22 | 0.27 | 0.05 |
| 3 | 0.22 | 0.3 | 0.08 | 3 | 0.21 | 0.24 | 0.03 |
| 4 | 0.22 | 0.29 | 0.07 | 4 | 0.22 | 0.29 | 0.07 |
| 5 | 0.21 | 0.25 | 0.04 | 5 | 0.21 | 0.26 | 0.05 |
| 6 | 0.22 | 0.29 | 0.07 | 6 | 0.23 | 0.26 | 0.03 |
| 7 | 0.21 | 0.23 | 0.02 | 7 | 0.21 | 0.26 | 0.05 |
| 8 | 0.21 | 0.28 | 0.07 | 8 | 0.21 | 0.27 | 0.06 |
| 9 | 0.22 | 0.32 | 0.1 | 9 | 0.21 | 0.24 | 0.03 |
| 10 | 0.22 | 0.28 | 0.06 | | | | |
| Mean | | | 0.068 | | | | 0.048 |

Mean percentage decrease in ear swelling intreated animals: 29.4%
Effect of treatment with 3-phenyl-2-[2-(3,4,5-trihydroxy-6-phosphonooxymethyl-tetrahydropyran-2-yl)-acetylamino]-propionic acid monosodium salt on DTH.

| 1 | 0.22 | 0.35 | 0.13 | 1 | 0.22 | 0.33 | 0.11 |
| 2 | 0.22 | 0.38 | 0.16 | 2 | 0.22 | 0.31 | 0.09 |
| 3 | 0.22 | 0.39 | 0.17 | 3 | 0.23 | 0.29 | 0.06 |
| 4 | 0.21 | 0.34 | 0.13 | 4 | 0.21 | 0.25 | 0.04 |
| 5 | 0.22 | 0.3 | 0.08 | 5 | 0.21 | 0.25 | 0.04 |
| Mean | | | 0.134 | | | | 0.068 |

Mean percentage decrease in ear swelling in treated animals: 49.3%
Effect of treatment with hexanoic acid 3-(3,4,5-trihydroxy-6-phosphonooxymethyl-tetrahydro-pyran-2-yl)-propyl ester sodium salt on DTH.

| 1 | 0.23 | 0.32 | 0.09 | 1 | 0.22 | 0.29 | 0.07 |
| 2 | 0.21 | 0.39 | 0.18 | 2 | 0.21 | 0.29 | 0.08 |
| 3 | 0.22 | 0.37 | 0.15 | 3 | 0.23 | 0.28 | 0.05 |
| 4 | 0.23 | 0.36 | 0.13 | 4 | 0.21 | 0.27 | 0.06 |
| 5 | 0.23 | 0.31 | 0.08 | 5 | 0.22 | 0.29 | 0.07 |
| Mean | | | 0.126 | | | | 0.066 |

Mean percentage decrease in ear swelling in treated animals: 47.6%

Example 23

Inhibition of Cell-mediated Disease of the Central Nervous System

Experimental autoimmune encephalomyelitis (EAE) is an inflammatory disease of the central nervous system that has similarities to multiple sclerosis (MS) and therefore, EAE is often used as an animal model of that disease and many references to this are to be found in the medical and scientific literature, included among these are Paterson, 1976; Alvord 1984 and Steinman, 1983; incorporated herein by reference. The pathology of EAE is characterised by an influx of lymphocytes and monocytes into the brain and spinal cord with an associated demyelination of the central nervous system neurones (Raine et al., 1980 and Paterson et al., 1981; incorporated herein by reference) resulting in partial or complete paralysis and in severe cases death. It is known that neural antigen-specific $CD4^+$ T lymphocytes are the initiators of the response since in vivo depletion of $CD4^+$ T lymphocytes inhibits induction of EAE (Waldor et al, 1985; incorporated herein by reference) and only $CD4^+$ T cell lines or clones can passively transfer the disease (Holda and Swanborg, 1982 and Ben-Nun and Cohen, 1982; incorporated herein by reference). Thus, the disease is characterised by its T lymphocyte mediated and tissue-specific nature.

Compounds of the present invention exhibit activity in the EAE assay and accordingly, one or more compounds of the invention may be useful in the treatment of multiple sclerosis or other cell-mediated diseases of the central nervous system.

In order to study the effect of the agents of the present invention in vivo on a disease caused by T lymphocyte migration into a specific tissue, experiments were performed in the Lewis rat model of passively transferred EAE. Here, myelin basic protein (MBP)-specific T lymphocyte cell lines were generated from the draining lymph nodes of Lewis rats that had been immunised with MBP in Freund's complete adjuvant essentially according to the method of Ben-Nun et al. (1981) as described in Example 8. Thus, in this manner, donor T lymphocytes were generated from female 10 to 12 week old Lewis rats weighing 150 to 200 g. These rats were injected intradermally in a footpad of each hind foot with an emulsion of Guinea pig myelin basic protein (MBP; prepared according to the method of Deibler et al., 1972; incorporated herein by reference) in Freund's complete adjuvant (0.05 ml). The adjuvant emulsion was prepared by emulsifying equal volumes of a mixture of light mineral oil (Sigma) and normal saline containing Guinea pig myelin basic protein (0.5 mg/ml) and *Mycobacterium butyricum* (4 mg/ml; Difco). Thus, the total dose per rat was 50 micrograms of MBP and 400 micrograms of *M. butyricum*. Approximately 11 days following injection, the rats were euthanased and the draining lymph nodes (popliteal and inguinal) removed aseptically by blunt dissection and placed into mixed lymphocyte culture medium. This medium was prepared in the normal fashion from Dulbecco's Modified Eagle's Medium (DMEM; GIBCO, Grand Island, N.Y.) supplemented with glucose, folic acid, L-asparagine, sodium bicarbonate, L-glutamine, sodium pyruvate, HEPES, 2-mercaptoethanol ($5 \times 10^{-5}$ M), penicillin, streptomycin, neomycin, and 2% fetal calf serum. A single cell suspension was prepared from the lymph nodes in the usual manner by gently pushing the nodes through a stainless steel screen. The cells were washed twice in the culture medium and following this procedure, any red blood cells were lysed in the usual manner by treating with a solution of ammonium chloride, EDTA and sodium hydrogen carbonate (pH 7.3) and the preparation strained (Falcon 2350 cell strainer). The cells were washed again in the lymphocyte culture medium. All cell preparative steps were performed on ice. These cells were cultured asceptically for 72 hours at 37° C. in a humidified atmosphere containing 7.5% carbon dioxide at a concentration of 5 million cells per milliliter in the presence of MBP (0.06 mg/ml). The cells were collected and the lymphoblasts were isolated by centrifugation on a Ficoll (Pharmacia, Uppsala, Sweden) gradient in an identical manner to that described by Ben Nun et al. (1981). The fraction containing $\geq 90\%$ lymphoblasts was cultured and propagated in Eagle's medium supplemented with 15% of a concanavalin A-stimulated lymphocyte supernatant to provide growth factors, 10% fetal calf serum, nonessential amino acids (Bio-Lab, Jerusalem, Israel); sodium pyruvate, 2-mercapto ethanol and antibiotics without added antigen. The cells were plated in 100 mm petri dishes at a concentration of 0.2 million cells/ml and replated every 3 or 4 days. Prior to transfer into Lewis recipients, the cells were restimulated in the presence of MBP (0.01 mg/ml) and irradiated syngeneic thymocytes for 4 days.

These cells were highly encephalitogenic sine as few as 500,000 cells were capable of inducing disease when injected into naïve Lewis rats. Thus, in a typical experiment a group of 5 female Lewis rats, approximately 9 weeks old, weighing 110±15 grams were anesthetised with diethyl ether and implanted with mini-osmotic pumps (Alzet 2002, Alza Corp., Palo Alto Calif., USA) containing phosphoric acid mono-(6-propyl-3,4,5-trihydroxy-tetrahydro-pyran-2-ylmethyl) ester mono sodium salt dissolved in normal saline at a concentration that delivered the drug at a rate of 45 mg/kg/rat/day. A second group of 5 animals, the control group, under ether anesthesia, were implanted with an Alzet 2002 pump containing normal saline. Just prior to recovering from the anesthetic, each animal received 500,000 cells of the encephalitogenic T cell line by lateral tail vein injection in a volume of 0.2 ml of normal saline.

The results of this experiment are outlined in Table 5. Thus, all of the animals (5/5) in the control group developed clinical disease while only 3/5 of the drug-treated animals developed disease and in these the severity was less than that found in the controls and disease onset was delayed. Thus, all of the rats in the control group developed clinical symptoms of disease on day 4 and none of the drug treated rats had symptoms at this time. Disease severity was scored on an arbitrary scale of severity ranging from 0 to 5 as follows: 0, asymptomatic; 1, flaccid distal half of tail; 2, entire tail flaccid; 3, ataxia, difficulty in righting reflex; 4, hind limb weakness; 5, hind limb paralysis. All of the animals in the saline treated control group had maximum clinical scores for two consecutive days while none of the 3 drug treated animals that developed symptoms had maximum clinical scores for more than one day. The severity of EAE for each group of rats was calculated as a disease index (DI) which is (the mean of the daily clinical score for all rats in the group divided by the mean day of onset, for those animals developing disease, multiplied by 100. This calculation allows a more complete assessment of the disease by incorporating the day of onset as well as the clinical severity and length of disease. Using this calculation, the control group had a disease index of 160 while the treated group had a disease index of 40. The mean maximum clinical score for the control group was 2.0 while that for the treated group was 1.0.

TABLE 5

Effect of treatment with phosphoric acid mono-(6-propyl-3,4,5-trihydroxy-tetrahydro-pyran-2-ylmethyl) ester on passively transferred EAE in Lewis rats.

| day | clinical scores saline | | | | | mean | clinical scores treated | | | | | mean |
|---|---|---|---|---|---|---|---|---|---|---|---|---|
| 4 | 1.5 | 1.5 | 1.5 | 1.5 | 2 | 1.6 | 0 | 0 | 0 | 0 | 0 | 0 |
| 5 | 2 | 2 | 2 | 2 | 2 | 2 | 0 | 0 | 1 | 1 | 1 | 0.6 |
| 6 | 2 | 2 | 2 | 2 | 2 | 2 | 0 | 0 | 1 | 2 | 2 | 1 |
| 7 | 2 | 0 | 0 | 1 | 1 | 0.8 | 0 | 0 | 1 | 0 | 1 | 0.4 |
| | DI 160 | | | | | | DI 40 | | | | | |
| | Mean maximum clinical score 2.0 | | | | | | Mean maximum clinical score 1.0 | | | | | |

In an identical experiment, rats were sacrificed on day 6 post lymphocyte transfer and their spinal cords taken for histological assessment. In this manner, rats were deeply anaesthetised (nembutal) and perfused with 30 ml saline followed by 60 ml 10% neutral buffered formalin. Spinal cords were removed, fixed for 7 days in 10% formalin and embedded for sectioning. The lumbar-sacral spinal cord was trans-sected and the halves embedded side by side for longitudinal sectioning. Six 5 micron sections were cut at various levels through the cord with 50 microns between levels. Sections were stained with hematoxylin and eosin and a minimum of 30 sections were counted at different levels in order to quantify the number of lesions.

The control group showed an extremely heavy lesion burden, on average approximately 15 lesions/section. While animals from the drug treated group had an average of 3.5 lesions and no more than 8 lesions per section in the most affected animal.

Example 24

Inhibition of Cell-Mediated Disease of the Central Nervous System

In a similar type of experiment outlined in Example 20, and in order to study the effect of the agents of the present invention in vivo on a disease caused by T lymphocyte migration into a specific tissue, further experiments were performed in a Lewis rat model of passively transferred EAE. Here, myelin basic protein (MBP)-specific T lymphocytes were generated in spleens of Lewis rats that had been immunised with guinea pig MBP in Freund's complete adjuvant. Thus, in this manner donor T lymphocytes were generated from male 12–20 week old Lewis rats weighing 200 to 250 g. These rats were injected intradermally in a footpad of each hind foot with an emulsion of guinea pig myelin basic protein (MBP; prepared according to the method of Deibler et al., 1972; incorporated herein by reference) in Freund's complete adjuvant (0.1 ml). The adjuvant emulsion was prepared by emulsifying equal volumes of a mixture of 85% light mineral oil (0.8417 g/mL (Sigma)) plus 15% mannide monooleate (Sigma) containing *Mycobacterium butyricum* (4 mg/ml; Difco) and normal saline containing guinea pig myelin basic protein (0.25 mg/ml). Thus, the total dose per rat was 25 micrograms of MBP and 400 micrograms of *M. butyricum*. Ten days following injection, the rats were euthanased and the spleens removed aseptically by blunt dissection and placed into mixed lymphocyte culture medium. This medium was prepared in the normal fashion from Dulbecco's Modified Eagle's Medium (DMEM; GIBCO, Grand Island, N.Y.) supplemented with glucose (4 g/L), folic acid (6 mg/L), L-asparagine (36 mg/L), sodium bicarbonate (2 g/L), L-arginine (116 mg/L), L-glutamine (2 mM), sodium pyruvate (1 mM), HEPES (10 mM), 2-mercaptoethanol ($5 \times 10^{-5}$ M), penicillin, streptomycin, neomycin, and 10% fetal calf serum. A single cell suspension was prepared from the spleens in the usual manner by gently pushing them through a stainless steel screen. The cells were washed twice and cultured aseptically for 72 hours at 37° C. in a humidified atmosphere containing 5% carbon dioxide at a concentration of 2 million cells per milliliter in the presence of concanavalin A (2 microgram/mL). The cells were collected and washed twice in Hanks balanced salt solution. Cells were resuspended in Hanks balanced salt solution and each recipient animal (10–12 weeks old female Lewis rats; 160–180 g) received 40–42.5 million lymphoblasts by lateral tail vein injection in a volume of 0.5 ml.

In a typical experiment 4–5 recipient rats were anesthetised with diethyl ether and implanted with mini-osmotic pumps (Alzet 2001, Alza Corp., Palo Alto Calif., USA) containing the test compound. A second group of 4 animals, the control group, under ether anesthesia, were implanted with Alzet 2001 pumps containing normal saline. Mini-osmotic pumps were implanted three days after cell transfer. Disease severity (clinical score) was scored on an arbitrary scale of severity ranging from 0 to 5 as follows: 0, asymptomatic; 1, flaccid distal half of tail; 2, entire tail flaccid; 3, ataxia, difficulty in righting reflex; 4, hind limb weakness; 5, hind limb paralysis. Mean maximum clinical scores were calculated and the disease index (DI) for each group was calculated as described in Example 20. The results of these experiments are outlined in Tables 6, 7 and 8.

TABLE 6

Effect of treatment with phosphoric acid mono-[6-(3-hexyloxypropyl)-3,4,5-trihydroxy-tetrahydro-pyran-2-ylmethyl] ester, sodium salt at a dose of 50 mg/kg/day, subcutaneously, on passively transferred EAE in Lewis rats.

| Rat | Clinical score - Control | | | | | Clinical score - Treated | | | | |
|---|---|---|---|---|---|---|---|---|---|---|
| Day | 1 | 2 | 3 | 4 | Mean | 1 | 2 | 3 | 4 | Mean |
| 5 | 3 | 5 | 3 | 3 | 3.5 | 0.5 | 0.5 | 1 | 2 | 1 |
| 6 | 4 | 5 | 5 | 4 | 4.5 | 3 | 2 | 2 | 4 | 2.75 |
| 7 | 4 | 4 | 5 | 3 | 4 | 2 | 2 | 2 | 4 | 2.5 |
| 8 | 3 | 3 | 4 | 2 | 3 | 2 | 3 | 2 | 2 | 2.25 |
| 9 | 1 | 0.5 | 1 | 1 | 0.875 | 1 | 1 | 1.5 | 1.5 | 1.25 |
| 10 | 1 | 0 | 0 | 0 | 0.25 | 0 | 0 | 1 | 1 | 0.5 |
| DI - 67.2 Mean maximum clinical score 4.5 | | | | | | DI - 34.1 Mean maximum clinical score 3 | | | | |

TABLE 7

Effect of treatment with 3-phenyl-2-[2-(3,4,5-trihydroxy-6-phosphonooxymethyl-tetrahydro-pyran-2-yl)-acetylamino]-propionic acid monosodium salt at a dose of 62 mg/kg/day subcutaneously, on passively transferred EAE in Lewis rats.

| Rat | Clinical score - Control | | | | | Clinical score - Treated | | | | | |
|---|---|---|---|---|---|---|---|---|---|---|---|
| Day | 1 | 2 | 3 | 4 | Mean | 1 | 2 | 3 | 4 | 5 | Mean |
| 4 | 0 | 0 | 0 | 1 | 0.3 | 0 | 0 | 0 | 0 | 0 | 0 |
| 5 | 2 | 0 | 1 | 2 | 1.3 | 0 | 1 | 1 | 2 | 0 | 0.8 |
| 6 | 2 | 1 | 1 | 2 | 1.5 | 0.5 | 1 | 1 | 2 | 0 | 0.9 |
| 7 | 2 | 0.5 | 0.5 | 1 | 1.0 | 0.5 | 1 | 0 | 2 | 0 | 0.7 |
| 8 | 1.5 | 0 | 0 | 0.5 | 0.5 | 0 | 1 | 1 | 1.5 | 0 | 0.7 |
| 9 | 0.5 | 0 | 0 | 0 | 0.1 | 0 | 0.5 | 0 | 1 | 0 | 0.4 |
| 10 | 0 | 0 | 0 | 0 | 0.0 | 0 | 0.5 | 0.5 | 0 | 0 | 0.2 |
| DI - 14.1 Mean maximum clinical score 1.5 | | | | | | DI - 8.13 Mean maximum clinical score 1.0 | | | | | |

TABLE 8

Effect of treatment with phosphoric acid mono-[3-(3,4,5-trihydroxy-6-phosphonooxymethyl-tetrahydro-pyran-2-yl)-propyl] ester disodium salt at a dose of 40 mg/kg/day intraperitoneally on passively transferred EAE in Lewis rats.

| Rat | Clinical score - Control | | | | | Clinical score - Treated | | | | |
|---|---|---|---|---|---|---|---|---|---|---|
| Day | 1 | 2 | 3 | 4 | Mean | 1 | 2 | 3 | 4 | Mean |
| 4 | 1 | 2 | 1.5 | 0 | 1.7 | 0 | 0 | 0 | 0 | 0 |
| 5 | 4 | 4 | 2 | 1 | 3.2 | 2 | 0 | 2 | 1.5 | 1.375 |
| 7 | 2 | 4 | 2.5 | 1.5 | 3.4 | 2.5 | 1 | 3 | 2 | 2.125 |
| 8 | 0.5 | 1 | 2 | 0 | 2.3 | 2 | 0.5 | 2.5 | 2 | 1.75 |
| 9 | 0 | 0.5 | 2 | 0 | 0.625 | 1 | 0 | 1 | 1 | 0.75 |
| 10 | 0 | 0 | 1 | 0 | 0.25 | 0 | 0 | 0 | 0.5 | 0.125 |
| DI - 45.0 Mean maxinium clinical score 3.0 | | | | | | DI - 18.6 Mean maximum clinical score 2.3 | | | | |

Example 25

Inhibition of Cell-mediated Disease of Synovial Tissue, Passively-transferred Adjuvant Induced Arthritis Passively transferred adjuvant arthritis is a T lymphocyte mediated disease in which T cells from an animal that has active arthritis are transferred into a naïve syngeneic recipient. The naïve recipient subsequently develops clinical signs of disease, including lymphocyte migration into the synovium with subsequent swelling of the affected joints. The immunological nature of this disease and the dependence upon T lymphocytes has been well established for many years in the medical and scientific literature and the following publications delineating these are included herein by reference: Kayashima et al., 1978; Waksman and Wennersten, 1963; Pearson and Wood, 1964 and Whitehouse et al, 1969.

The experiment in this example was set up in order to study the effect of the agents of the present invention in vivo on a disease directly caused by T lymphocyte migration into a specific tissue (synovium). Male DA rats 8 to 10 week old were immunised with three 100 microliter injections of Complete Freund's Adjuvant (CFA) intradermally at the base of the tail. The CFA was prepared by mixing 8 mg/ml of *Mycobacterium butyricum* (Difco Laboratories, USA) that had been ground to a fine powder using a mortar and pestle, in 85% light mineral oil (Sigma, USA) and 15% mannide monooleate (Sigma) and emulsifying this suspension, one part in one part saline. Thus, the final emulsion contained 4 mg/ml of *M. butyricum*.

Ten days after immunisation the rats were euthanased and the spleens removed aseptically. A single cell suspension was prepared in the usual manner in mixed lymphocyte culture medium (MLC) (Dulbecco's Modified Eagle's Medium (DMEM) plus glucose, folic acid, L-asparagine, sodium pyruvate, HEPES, 2-mercapto ethanol, penicillin, streptomycin, neomycin and 10% fetal calf serum) by pushing the spleens through a stainless steel sieve. The cells were placed in culture in MLC medium with 2 micrograms/ml concanavalin A added such that the lymphocyte concentration was 2 million cells per milliliter. These cells were cultured aseptically at 37° C. in an atmosphere containing 5% carbon dioxide for 72 hours.

Groups of 4 or 5 DA rats, 6 to 8 weeks of age were anesthetised with diethyl ether and implanted subcutaneously on the flank with Alzet 2002 (2 week delivery) or 2001 (1 week delivery) mini-osmotic pumps (Alza Corp., Palo Alto Calif., USA). One treatment group received phosphoric acid mono-(6-propyl-3,4,5-trihydroxy-tetrahydro-pyran-2-ylmethyl) ester in the one week delivery Alzet 2001 mini-osmotic pumps. The drug was delivered at a dose of 25 mg/kg/day. The control group for this experiment received identical mini-osmotic pumps containing normal saline. In a second experiment another group of DA rats received ethyl (3,4,5-trihydroxy-6-phosphonooxymethyl-tetrahydro-pyran-2-yl)-acetic acid ester in the two week delivery Alzet 2002 mini-osmotic pumps. This drug was delivered at a dose of 37 mg/kg/day. Control animals for this group received saline delivered in identical mini-osmotic pumps. The pumps in each case were implanted subcutaneously on the flank of each animal. During the period of recovery from the anesthetic, the lymphocytes from above which had been harvested and washed twice with Hanks' balanced salt solution were resuspended in normal saline and transferred into the recipient rats by injecting 75 to 90 million cells in a volume of 0.5 ml into a lateral tail vein.

After 5 to 8 days, a characteristic thickening and cutaneous hyperemia of the distal joints of the hind legs became clinically apparent in the saline control animals. Disease severity was evaluated and graded in each group by taking daily measurements of the mediolateral widths of both ankle joints. The data were expressed as the mean of the change (compared with width prior to cell injection) in mediolateral ankle width expressed in millimeters (±standard error of the mean).

FIG. 1 shows the results obtained from a typical experiment in which phosphoric acid mono-(6-propyl-3,4,5-trihydroxy-tetrahydro-pyran-2-ylmethyl) ester was delivered in the one week delivery Alzet 2001 mini-osmotic pumps at a dose of 25 mg/kg/day. At the end of the one week treatment period, there was a highly statistically significant difference in the disease status of the treated versus the control animals. The control animals had severe swelling in the affected joints while the treated animals showed little swelling at the end of the treatment period.

Figure 2:
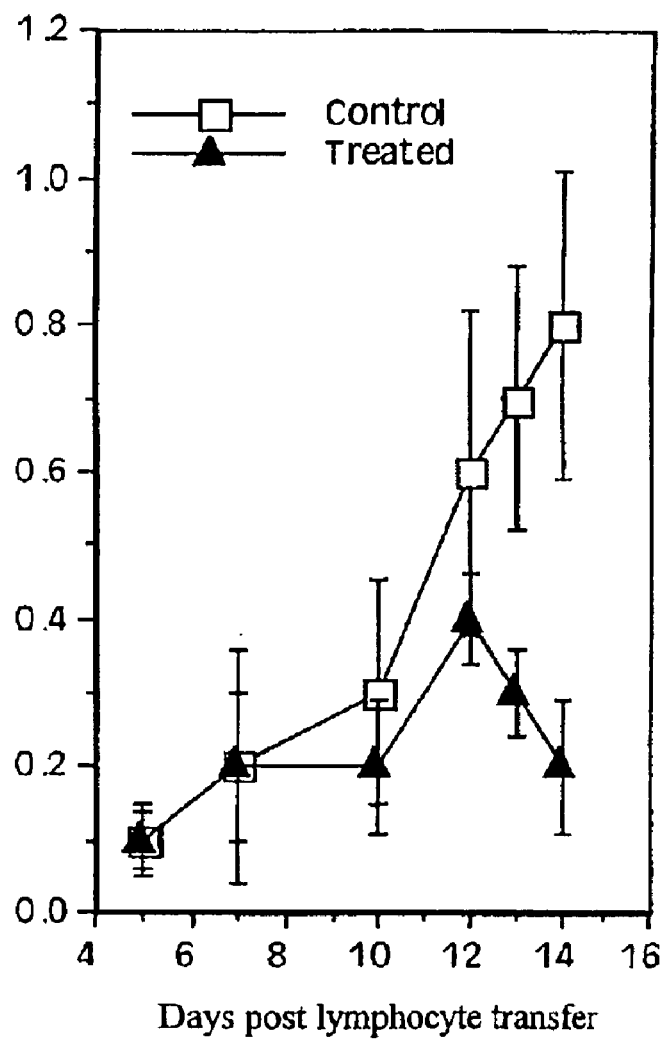
FIG. 2 graphically depicts the effect of ethyl (3,4,5-trihydroxy-6-phosphonooxymethyl-tetrahydropyran-2-yl acetic acid ester delivered at a dose of 37 mg/kg/day on passively transferred induced arthritis

FIG. 2 shows the results obtained from a typical experiment in which ethyl (3,4,5-trihydroxy-6-phosphonooxymethyl-tetrahydro-pyran-2-yl)-acetic acid ester was delivered in the two week delivery Alzet 2002 mini-osmotic pumps at a dose of 37 mg/kg/day. At the end of the two week treatment period there was a highly statistically significant difference in the disease status of the treated versus the control animals. The control animals had severe swelling in the affected joints while the treated animals showed little swelling at the end of the treatment period.

References

*Immmunology* 5$^{th}$ Edition 1998; Ivan M. Roitt Ed, Blackwell Scientific Publications, Boston.

*Immunobiology: the Immune System in health and disease* 4$^{th}$ Edition 1999, C. A. Janeway P. Travers, M. Walport and J. D. Capra, Eds. Elsevier Science/Garland Publishing New York.

*The Pathogenesis of Infectious Disease* 1982, C. A. Mims Ed; Academic Press, New York, 1982

Klein, J. and Horejsi, Vaclav 1997. *Autoimmunity and autoimmune diseases*, pp 656–657. In: Immunology (Second Edition), Blackwell Science Ltd., Oxford.

Bos, J. D. and De Rie M. A., (1999). The pathogenesis of psoriasis: immunological facts and speculations. *Immunology Today*, 1999, vol. 20: 40–46.

*Comprehensive Organic Transformations*, R. Larock, VCH Publishers, 1989.

*Advanced Organic Chemistry*, J. March, Third Edition, Wiley InterScience.

*Protective Groups in Organic Synthesis*, T. W. Greene and P. Wutz, John Wiley and Son, (1991).

Paterson, P. Y. (1976). In *Textbook of Immunopathology* (eds Miescher, P. A. and Mueller-Eberhard, H. J.) 179–213 (Grune & Stratton, New York, 1976).

Alvord, E. C. Jr. (1984). In Experimental Allergic Encephalomyelitis: *A Useful Model for Multiple Sclerosis* (ed Alvord, E. C.), 1–511 (Liss, New York, 1984).

Steinman, L. (1993). Autoimmune Disease. *Scientific American*, vol 269: 106–114.

Raine, C. S., Barnett, L. B., Brown, A. and McFarlin, D. E. (1980). Neuropathology of experimental allergic encephalomyelitis in inbred strains of mice. *Lab. Invest.*, vol 43: 150–157.

Paterson, P. Y., Day, E. D. and Whitacre, C. C. (1981). Neuroimmunologic diseases: Effector cell responses and immunoregulatory mechanisms. *Immunol. Rev.*, vol 55: 89–120.

Waldor, M. K., Sriram, S., Hardy, R., Herzenberg, L. A., Herzenberg, L. A., Lanier, L., Lim, M. and Steinman, L. (1985). Reversal of experimental allergic encephalomyelitis with monoclonal antibody to a T-cell subset marker. *Science*, vol 227: 415–417.

Holda, J. A. and Swanborg, R. H. Autoimmune effector cells. (1982). II. Transfer of experimental allergic encephalomyelitis with a subset of T-lymphocytes. *European Journal of Immunology*, vol 12: 453–455.

Ben-Nun, A. and Cohen, I. R. (1982). Experimental autoimmune encephalomyelitis (EAE) mediated by T-cell lines: Process of selection of lines and characterization of the cells. *Journal of Immunology* Vol 129: 303–308.

Deibler, G. E., Martenson, B. L. and Kies, M. W., (1972). Large scale preparation of myelin basic protein from central nervous tissue of several mammalian species. *Preparative Biochemistry*, vol 2: 139–165.

von Isler, O., Gutmann, H., Montavon, M., Ruegg, R., Ryser, G. and Zeller, P., (1957). Synthesen in der carotinoid-Reihe. Anwendung der Wittig-reaktion zur synthese von estern des bixins and crocetins. *Helvetica Chimica Acta*, vol 15: 1242–1249

Giannis, A. and Sandhoff, K., (1985). Stereoselective synthesis of α-C-allylglycopyranosides. *Tetrahedron Letters*, vol 26(12): 1479–1482.

Levene, P. A. and Tipson, R. S., (1931). The ring structure of the mannose pentaacetates. *Journal of Biological Chemistry*, vol 90: p 89–98.

Hurd, C. D. and Holysz, R. P. (1950). Reactions of polyacylglycosyl halides with Grignard reagents. *Journal of the American Chemical Society*, 1950, vol 72: 1732–1738.

Finan, P. A. and Warren C. D., (1962), The purification of acetylglucosyl bromides. *Journal of the Chemical Society*, 2823–2824.

Poggi, A., Costa, P., Socchi, M. R. and Moretta, L., (1997). Phenotypic and functional analysis of CD4+ NKRP1A+ human lymphocytes. Direct evidence that the NKRP1A molecule is involved in transendothelial migration. *European Journal of Immunology*, vol 27: 2345–2350.

Hauzenberger, E., Hauzenberger, D., Hultenby, K. and Holgersson, J., (2000). Porcine endothelium supports transendothelial migration of human leukocyte subpopulations: anti-porcine vascular cell adhesion molecule antibodies as species-specific blockers of transendothelial monocyte and natural killer cell migration. *Transplantation*. Vol 69(9): 1837–1849.

Borthwick, N. J., Akbar, A. N., MacCormac, L. P., Lowdell, M., Craigen, J. L., Hassan, I., Grundy, J. E., Salmon, M. and Yong K. L., (1997). Selective migration of highly differentiated primed T cells, defined by low expression of CD45RB, across human umbilical vein endothelial cells: effects of viral infection on transmigration. *Immunology*. Vol 90(2): 272–280.

Mohle, R., Moore, M. A., Nachman, R. L. and Rafii, S., (1997). Transendothelial migration of CD34+ and mature hematopoietic cells: an in vitro study using a human bone marrow endothelial cell line. *Blood*. Vol 89(1): 72–80.

Lou, J., Gasche, Y., Zheng, L., Giroud, C., Morel, P., Clements, J., Ythier, A. and Grau, G. E., (1999). Interferon-beta inhibits activated leukocyte migration through human brain microvascular endothelial cell monolayer. *Laboratory Investigation* vol 79(8): 1015–1025.

Jaffe, E. A., Nachman, R. L., Becker, C. G. and Minick, C. R., (1973). Culture of human endothelial cells derived from umbilical veins. Identification by morphologic and immunologic criteria. *Journal of Clinical Investigation*, vol 52(11): 2745–2756.

Risau, W., Engelhardt, B., and Wekerle, H., (1990). Immune function of the blood-brain barrier: Incomplete presentation of protein (auto-)antigens by rat brain microvascular endothelium in vitro. *Journal of Cell Biology*, vol 110: p 1757–1766

Ben-Nun, A., Wekerle, H. and Cohen, I. R., (1981). The rapid isolation of clonable antigen-specific T lymphocyte lines capable of mediating autoimmune encephalomyelitis. *European Journal of Immunology*. 1981, 11(3): 195–199.

Kayashima, K., Koga, T. and Onoue, K., 1978. Role of T lymphocytes in adjuvant arthritis II. Different subpopulations of T lymphocytes functioning in the development of disease. *Journal of Immunology*, vol 120: 1127–1131.

Waksman, B. H. and Wennersten, C., 1963. Passive transfer of adjuvant arthritis in rats with living lymphoid cells of sensitized donors. *International Archives of Allergy*, vol 23: 129–139.

Pearson, C. M. and Wood, F. D., 1964. Passive transfer of adjuvant arthritis by lymph node or spleen cells. *Journal of Experimental Medicine*, vol 120: 547–560.

Whitehouse, D. J., Whitehouse, M. W. and Pearson, C. M., 1969. Passive transfer of adjuvant-induced arthritis and allergic encephalomyelitis in rats using thoracic duct lymphocytes. *Nature*, vol 224: 1322.

Malet, C., Viladot, J. L, Ochoa, A., Gallego, B., Brosa, C. and Planas, A., 1995. Synthesis of 4-methyllumbelliferyl-b-D-glucan oligosaccharides as specific chromophoric substrates of (1-3), (1-4)-b-D-glucan 4-glucanohydrolases. *Carbohydrate Res.*, 274: 285–301.

Guo, Z., Zhang, G. and Hui, Y., 1997. A facile regioselective 1,6-O-diacetylation method of methyl-gylcopyranosides and their dimethyl phosphonates, *Synthetic Communcations*, vol 27, 1907–1917.

Wong, C. H., Hung, S. C. and Lin, C. C., 1997. One-pot synthesis of 1-allyl and 1-allenyl-6-O-acetyl-2,3,4-tri-O-benzyl-α-D-glycosides from methyl tetra-O-benzyl-α-D-glycosides, *Tetrahedron Letters*, vol 38, 5419–5422.

Khan, R., Konowicz, P. A., Gardossi. L., Matulova, M. and Gennaro, S., 1996. Regioselective deacetylation of fully acetylated mono- and di-saccharides with hydrazine hydrate, *Australian Journal of Chemistry*, vol 49, 293–298.

Mata, F. Z., Martinez, M. B. and Perez, J. A. G., 1992. Reaction of Meldrum's acid with D-mannose and L-arabinose, Carbohydrate Research, vol 225, 159–161.

Klimuk, S. K., Semple, S. C., Scherrer, P. and Hope, M. J., 1999. contact hypersensitivity: a simple model for the characterization of disease-site targeting by liposomes. Biochemica et Biophysica Acta, vol 1417, 191–201.

Rodrigues, F., Canac, Y., and Lubineau, A., 2000. A convenient, one-step, synthesis of β-C-glycosidic ketones in aqueous media. Chemical Communications, 2049–2050.

We claim:

1. A compound of Formula (I), or a salt, solvate, hydrate, amide or ester thereof, in the configuration depicted (2RS):

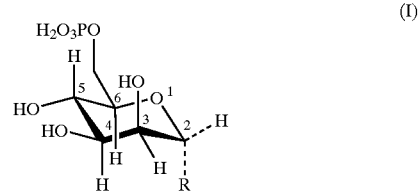

wherein R is axial or equatorial and is selected from the group consistin of:
alkyl, alkenyl, alkynyl, aryl, heteroaryl, aralkyl, heteroaralkyl, cyano, hydroxy-tetrahydro-pyranyloxyalkyl, —(CH$_2$)$_n$CH$_2$OR", —(CH$_2$)$_n$CONHR",
—(CH$_2$)$_n$CH$_2$NHR" and (CH$_2$)$_n$COX,
  wherein n represents an integer from 0 to 20 inclusive;
  R" is selected from the group consisting of H, alkyl, aryl and acyl; and
  X is selected from the group consisting of Y, OY' and NY"Y'"
    wherein Y is selected from the group consisting of H, alkyl, alkenyl, alkynyl, aryl, heteroaryl, aralkyl, heteroaralkyl and carbohydrate; Y' is selected from the group consisting of H, alkyl, alkenyl, alkynyl, aryl, heteroaryl, aralkyl, heteroaralkyl and carbohydrate; and
    Y" and Y'" are independently selected from the group consisting of H, alkyl, alkenyl, alkynyl, aryl, heteroaryl, aralkyl, heteroaralkyl and acyl;
wherein each of alkyl, alkenyl, alkynyl, aryl, heteroaryl, aralkyl, heteroaralkyl and acyl may be optionally substituted;
provided that R is not methyl.

2. A compound according to claim 1 wherein is selected from the group consisting of cyano, optionally substituted phenyl and optionally substituted alkyl.

3. A compound according to claim 2 wherein R is an alkyl group substituted by OC(O)alkyl, NHC(O)alkyl, OPO$_3$H$_2$, alkoxy or O-carbohydrate.

4. A compound according to claim 1 wherein R is selected from the group consisting of cyano, —(CH$_2$)$_n$CO$_2$R', —(CH$_2$)$_n$CHO, —(CH$_2$)$_n$CH$_2$OR", —(CH$_2$)$_n$CONHR", —(CH$_2$)$_n$CH$_2$NHR", and —(CH$_2$)$_n$CONR"R'"
  wherein n is selected from 0–20, R' is H, alkyl or aryl, R" is H, alkyl, aryl or acyl and R'" is H, alkyl, aryl or acyl.

5. A compound according to claim 1 wherein n is 0–12.

6. A compound according to claim 1 wherein R is selected from the group consisting of cyano; hydroxyalkyl; alkoxyalkyl; aryloxyalkyl; hydroxy-tetrahydro-pyranyloxyalkyl; aminoakyl; benzyl; phenylethyl; phenyl; 2-, 3- or 4-methoxyphenyl; 2-, 3- or 4-methylphenyl; 2, 3 or 4-pyridyl; 2-, 4- or 5-pyrimidinyl; 2- or 3-thiophenyl; 2-, 4-, or 5-(1,3)oxazolyl; 2-, 4- or 5-(1,3)thiazolyl; 2- or 4-imidazolyl; 3- or 5-symtriazolyl; (CH$_2$)$_n$C(O)C$_{1-6}$alkyl; —(CH$_2$)$_n$C(O)aryl; —(CH$_2$)$_n$CO$_2$C$_{1-10}$ alkyl; —(CH$_2$)$_n$CO$_2$aryl; —(CH$_2$)$_n$CONHC$_{1-10}$alkyl; —(CH$_2$)$_n$CONHaryl and —(CH$_2$)$_n$CON(C$_{1-10}$alkyl)$_2$.

7. A compound of Formula (I) or a salt, solvate, hydrate, amide or ester thereof, in the configuration depicted (2RS):

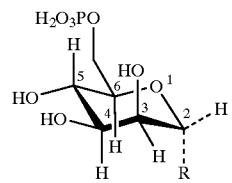

wherein R is axial or equitorial and is selected from the group consisting of:
—CH$_2$CO$_2$CH$_3$, —CH$_2$CO$_2$CH$_2$CH$_3$, —CH$_2$CO$_2$(CH$_2$)$_4$CH$_3$, —CH$_2$CO$_2$(CH$_2$)$_2$Ph, CH$_2$CO$_2$H, —CH$_2$CH=CH$_2$, —(CH$_2$)$_2$CH$_3$, —CN, —C$_6$H$_5$, —C$_6$H$_4$OCH$_3$, -2-pyridyl, —(CH$_2$)$_4$CH$_3$, —(CH$_2$)$_2$Ph, —(CH$_2$)$_3$—O—PO$_3$H$_2$, —(CH$_2$)$_3$—O—CO(CH$_2$)$_5$CH$_3$, —(CH$_2$)$_3$OH, —CH$_2$CONHCH(CO$_2$H)CH$_2$Ph, —(CH$_2$)$_3$—O—(CH$_2$)$_5$CH$_3$, —(CH$_2$)$_3$NHCO(CH$_2$)$_2$CH$_3$, —CH$_2$CONHCH(CO$_2$H)CH$_2$CH$_2$CO$_2$H, —CH$_2$CONH(CH$_2$)$_2$Ph, —(CH$_2$)$_3$—O-(1'-maltosyl), —(CH$_2$)$_2$—O-(1'-maltosyl), —(CH$_2$)$_3$—NH-Val-Asp-BocLeu, —CH$_2$COCH$_3$ and —(CH$_2$)$_3$—O—C$_6$H$_4$—O—(CH$_2$)$_3$-Z,
wherein Z is

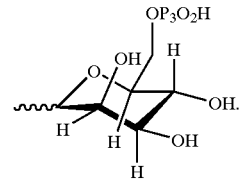

8. A method of treating rheumatoid arthritis, multiple sclerosis or acute disseminated encaphalomyelitis, comprising administering a treatment effective amount of a compound of Formula(I), or a salt, solvate, hydrate, amide or ester thereof, in the configuration depicted (2RS):

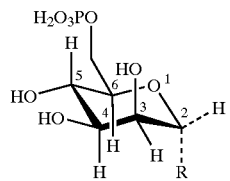

wherein R is axial or equatorial and is selected from the group consistin of:
H, alkyl, alkenyl, alkynyl, aryl, heteroaryl, aralkyl, heteroaralkyl, cyano, hydroxy-tetrahydro-pyranyloxyalkyl, —(CH$_2$)$_n$CH$_2$OR", —(CH$_2$)$_n$CONHR", —(CH$_2$)$_n$CH$_2$NHR" and (CH$_2$)$_n$COX,
  wherein n represents an integer from 0 to 20 inclusive;
  R" is selected from the group consisting of H, alkyl, aryl and acyl; and
  X is selected from the group consisting of Y, OY' and NY"Y'"
    wherein Y is selected from the group consisting of H, alkyl, alkenyl, alkynyl, aryl, heteroaryl, aralkyl, heteroaralkyl and carbohydrate; Y' is selected from the group consisting of H, alkyl, alkenyl, alkynyl, aryl, heteroaryl, aralkyl, heteroaralkyl and carbohydrate; and
    Y" and Y'" are independently selected from the group consisting of H, alkyl, alkenyl, alkynyl, aryl, heteroaryl, aralkyl, heteroaralkyl and acyl;
wherein each of alkyl, alkenyl, alkynyl, aryl, heteroaryl, aralkyl, heteroaralkyl and acyl may be optionally substituted.

9. A method according to claim 8 wherein wherein R is selected from the group consisting of cyano, optionally substituted phenyl or optionally substituted alkyl.

10. A method according to claim 9 wherein R is an alkyl group substituted by OC(O)alkyl, NHC(O)alkyl, OPO$_3$H$_2$, alkoxy or O-carbohydrate.

11. A method according to claim 8 wherein R is selected from the group consisting of cyano, —(CH$_2$)$_n$CO$_2$R', —(CH$_2$)$_n$CHO, —(CH$_2$)$_n$CH$_2$OR", —(CH$_2$)$_n$CONHR", —(CH$_2$)$_n$CH$_2$NHR", and —(CH$_2$)$_n$CONR"R'"
wherein n is selected from 0–20, R' is H, alkyl or aryl, R" is H, alkyl, aryl or acyl and R'" is H, alkyl, aryl or or acyl.

12. A method according to claim 11 wherein n is 0–12.

13. A method according to claim 8 wherein is selected from the group consisting of cyano, hydroxyalkyl, alkoxyalkyl; aryloxyalkyl, hydroxy-tetrahydro-pyranyloxyalkyl, aminoalkyl, benzyl, phenylethyl, phenyl, 2-, 3- or 4-methoxyphenyl, 2-, 3- or 4-methylphenyl, 2, 3 or 4-pyridyl, 2-, 4- or 5-pyrimidinyl, 2- or 3-thiophenyl, 2-, 4-, or 5-(1,3)oxazolyl, 2-, 4- or 5-(1,3)thiazolyl, 2- or 4-imidazolyl, 3- or 5-symtriazolyl, $(CH_2)_nC(O)C_{1-6}$alkyl, $-(CH_2)_nC(O)$aryl, $-(CH_2)_nCO_2C_{1-10}$ alkyl, $-(CH_2)_nCO_2$aryl, $-(CH_2)_nCONHC_{1-10}$alkyl, $-(CH_2)_nCONH$aryl and $-(CH_2)_nCON(C_{1-10}$alkyl$)_2$.

14. A method of treating rheumatoid arthritis, multiple sclerosis or acute disseminated encaohalomyelitis comprising administering a treatment effective amount of a compound of Formula (I), or a salt, solvate, hydrate, amide or ester thereof, in the configuration depicted (2RS):

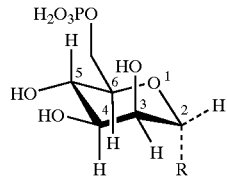

wherein R is axial or equitorial and is selected from the group consisting of:
H, $-CH_2CO_2CH_3$, $-CH_2CO_2CH_2CH_3$, $-CH_2CO_2(CH_2)_4CH_3$, $-CH_2CO_2(CH_2)_2Ph$, $CH_2CO_2H$, $-CH_2CH=CH_2$, $-(CH_2)_2CH_3$, $-CN$, $-C_6H_5$, $-C_6H_4OCH_3$, -2-pyridyl, $-(CH_2)_4CH_3$, $-(CH_2)_2Ph$, $-(CH_2)_3-O-PO_3H_2$, $-(CH_2)_3-O-CO(CH_2)_5CH_3$, $-(CH_2)_3OH$, $-CH_2CONHCH(CO_2H)CH_2Ph$, $-(CH_2)_3-O-(CH_2)_5CH_3$, $-(CH_2)_3NHCO(CH_2)_2CH_3$, $-CH_2CONHCH(CO_2H)CH_2CH_2CO_2H$, $-CH_2CONH(CH_2)_2Ph$, $-(CH_2)_3-O-(1'-maltosyl)$, $-(CH_2)_2-O-(1'-maltosyl)$, $-(CH_2)_3-NH-Val-Asp-BocLeu$, $-CH_2COCH_3$ and $-(CH_2)_3-O-CoH_4-O-(CH_2)_3-Z$, wherein Z is

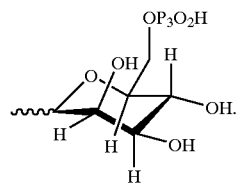

15. A composition for treating rheumatoid arthritis, multiple sclerosis or acute disseminated encephalomyelitis comprising a compound as defined in claim 1 together with a pharmaceutically acceptable carrier, diluent or excipient.

16. A compound according to claim 5 wherein n is 1–6.

17. A method according to claim 12 wherein n is 1–6.

18. A composition for treating rheumatoid arthritis, multiple sclerosis or acute disseminated encephalomyelitis comprising a compound as defined in claim 7 together with a pharmaceutically acceptable carrier, diluent or excipient.

* * * * *